US012492243B2

(12) United States Patent
Weiner et al.

(10) Patent No.: US 12,492,243 B2
(45) Date of Patent: Dec. 9, 2025

(54) DNA ANTIBODY CONSTRUCTS FOR USE AGAINST *Pseudomonas aeruginosa*

(71) Applicants: The Trustees of the University of Pennsylvania, Philadelphia, PA (US); THE WISTAR INSTITUTE OF ANATOMY AND BIOLOGY, Philadelphia, PA (US); Inovio Pharmaceuticals, Inc., Plymouth Meeting, PA (US)

(72) Inventors: David Weiner, Merion, PA (US); Ami Patel, Philadelphia, PA (US); Jian Yan, Wallingford, PA (US)

(73) Assignees: The Trustees of the University of Pennsylvania, Philadelphia, PA (US); The Wistar Institute of Anatomy and Biology, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 1228 days.

(21) Appl. No.: 16/098,908

(22) PCT Filed: May 5, 2017

(86) PCT No.: PCT/US2017/031449

§ 371 (c)(1),
(2) Date: Nov. 5, 2018

(87) PCT Pub. No.: WO2017/193101

PCT Pub. Date: Nov. 9, 2017

(65) Prior Publication Data

US 2019/0153076 A1 May 23, 2019

Related U.S. Application Data

(60) Provisional application No. 62/332,363, filed on May 5, 2016.

(51) Int. Cl.

| | |
|---|---|
| ***C07K 16/12*** | (2006.01) |
| ***A61K 31/407*** | (2006.01) |
| ***A61K 39/40*** | (2006.01) |
| ***A61P 31/04*** | (2006.01) |
| ***C07K 16/00*** | (2006.01) |
| ***C07K 16/46*** | (2006.01) |
| *A61K 39/00* | (2006.01) |

(52) U.S. Cl.

CPC ........ *C07K 16/1214* (2013.01); *A61K 31/407* (2013.01); *A61K 39/40* (2013.01); *A61P 31/04* (2018.01); *C07K 16/00* (2013.01); *C07K 16/12* (2013.01); *C07K 16/468* (2013.01); *A61K 2039/505* (2013.01); *A61K 2039/53* (2013.01); *C07K 2317/31* (2013.01)

(58) Field of Classification Search

CPC .. C07K 16/1214; C07K 16/00; C07K 16/468; A61P 31/04; A61K 39/40; A61K 2039/505

See application file for complete search history.

(56) References Cited

U.S. PATENT DOCUMENTS

| | | |
|---|---|---|
| 9,403,901 B2 | 8/2016 | Digiandomenico |
| 2015/0274845 A1 | 10/2015 | Bruenker |
| 2015/0284448 A1 | 10/2015 | Weiner |

FOREIGN PATENT DOCUMENTS

| | | | |
|---|---|---|---|
| AU | 2012304313 A1 | 3/2014 | |
| CN | 101910197 B | 9/2014 | |
| EP | 2747781 B1 | 11/2017 | |
| JP | 2014526472 | 10/2014 | |
| JP | 2014533249 | 12/2014 | |
| JP | 2015504421 | 2/2015 | |
| TW | I719938 B | 3/2021 | |
| WO | WO-2013070615 A1 * | 5/2013 | ............. A61K 39/40 |
| WO | 2014093894 A2 | 6/2014 | |
| WO | 2015089492 A2 | 6/2015 | |
| WO | WO-2015171504 A1 * | 11/2015 | ............. A61K 39/40 |
| WO | 2015196011 A1 | 12/2015 | |

OTHER PUBLICATIONS

Edelman et al. 2001 (Degeneracy and complexity in biological systems; PNAS 98(24): 13763-13768). (Year: 2001).*

Allison, T. L. "Immunosuppressive Therapy in Transplantation". Nurs Clin North Am 51, 107-120, (2016).

Andre, S. et al. "Increased immune response elicited by DNA vaccination with a synthetic gp120 sequence with optimized codon usage". J Virol 72, 1497-1503 (1998).

Breidenstein, E. B., de la Fuente-Nunez, C. & Hancock, R. E. "Pseudomonas aeruginosa: all roads lead to resistance". Trends Microbiol 19, 419-426, (2011).

Byrd, M. S. et al. "Genetic and biochemical analyses of the Pseudomonas aeruginosa Psl exopolysaccharide reveal overlapping roles for polysaccharide synthesis enzymes in Psl and LPS production". Mol Microbiol 73, 622-638, (2009).

CDC. "Antibiotic Resistance Threats in the United States", 2013. (2013).

Cemazar, M. et al. "Hyaluronidase and collagenase increase the transfection efficiency of gene electrotransfer in various murine tumors". Human gene therapy 23, 128-137, (2012).

Chan, A. C. & Carter, P. J. "Therapeutic antibodies for autoimmunity and inflammation". Nat Rev Immunol 10, 301-316, (2010).

(Continued)

*Primary Examiner* — Mary Maille Lyons

(74) *Attorney, Agent, or Firm* — Riverside Law LLP

(57) ABSTRACT

Disclosed herein are mono and bispecific DNA antibodies (DMAbs) targeting *Pseudomonas aeruginosa*. Also disclosed herein is a method of generating a synthetic antibody in a subject by administering the DMAbs to the subject. The disclosure also provides a method of preventing and/or treating *Pseudomonas aeruginosa* infection in a subject using said composition and method of generation.

15 Claims, 10 Drawing Sheets

Specification includes a Sequence Listing.

(56) References Cited

OTHER PUBLICATIONS

Collignon, P. C. et al. "World Health Organization Ranking of Antimicrobials According to Their Importance in Human Medicine: A Critical Step for Developing Risk Management Strategies to Control Antimicrobial Resistance From Food Animal Production". Clin Infect Dis, (2016).
Deml, L. et al. "Multiple effects of codon usage optimization on expression and immunogenicity of DNA candidate vaccines encoding the human immunodeficiency virus type 1 Gag protein". J Virol 75, 10991-11001, (2001).
Digiandomenico Antonio et al: "A multifunctional bispecific antibody protects against Pseudomonas aeruginosa", Science Translational Medicine, vol. 6, No. 262, Nov. 12, 2014 (2014-11-12), pp. 262ra155-1.
Digiandomenico, A. et al. "Identification of broadly protective human antibodies to Pseudomonas aeruginosa exopolysaccharide Psl by phenotypic screening". J Exp Med 209, 1273-1287, (2012).
Falagas, M. E. et al. "Toxicity after prolonged (more than four weeks) administration of intravenous colistin". BMC Infect Dis 5, 1, (2005).
Fath, S. et al. "Multiparameter RNA and codon optimization: a standardized tool to assess and enhance autologous mammalian gene expression". PLoS One 6, e17596, (2011).
Ferraro, B. et al. "Clinical applications of DNA vaccines: current progress". Clin Infect Dis 53, 296-302, (2011).
Flingai, S. et al. "Protection against dengue disease by synthetic nucleic acid antibody prophylaxis/immunotherapy". Sci Rep 5, 12616, (2015).
Graf, M., Deml, L. & Wagner, R. "Codon-optimized genes that enable increased heterologous expression in mammalian cells and elicit efficient immune responses in mice after vaccination of naked DNA". Methods Mol Med 94, 197-210 (2004).
Hauser, A. R. "The type III secretion system of Pseudomonas aeruginosa: infection by injection". Nat Rev Microbiol 7, 654-665, (2009).
Hirao, L. A. et al. "Comparative analysis of immune responses induced by vaccination with SIV antigens by recombinant Ad5 vector or plasmid DNA in rhesus macaques". Molecular therapy : the journal of the American Society of Gene Therapy 18, 1568-1576, (2010).
Hirsch, E. B. & Tam, V. H. "Impact of multidrug-resistant Pseudomonas aeruginosa infection on patient outcomes". Expert Rev Pharmacoecon Outcomes Res 10, 441-451, (2010).
Jackson, K. D., Starkey, M., Kremer, S., Parsek, M. R. & Wozniak, D. J. "Identification of psl, a locus encoding a potential exopolysaccharide that is essential for Pseudomonas aeruginosa PAO1 biofilm formation". J Bacteriol 186, 4466-4475, (2004).
Kim, H. et al. "Gene therapy using plasmid DNA-encoded anti-HER2 antibody for cancers that overexpress HER2" Cancer Gene Ther 23, 341-347, (2016).
Lim, L. M. et al. "Resurgence of colistin: a review of resistance, toxicity, pharmacodynamics, and dosing". Pharmacotherapy 30, 1279-1291, (2010).
Lister, P. D., Wolter, D. J. & Hanson, N. D. "Antibacterial-resistant Pseudomonas aeruginosa: clinical impact and complex regulation of chromosomally encoded resistance mechanisms". Clin Microbiol Rev 22, 582-610, (2009).
Matera, M. G., Page, C., Rogliani, P., Calzetta, L. & Cazzola, M. "Therapeutic Monoclonal Antibodies for the Treatment of Chronic Obstructive Pulmonary Disease. Drugs", (2016).
Mishra, M. et al. "Pseudomonas aeruginosa Psl polysaccharide reduces neutrophil phagocytosis and the oxidative response by limiting complement-mediated opsonization". Cell Microbiol 14, 95-106, (2012).
Muthumani, K. et al. "Rapid and Long-Term Immunity Elicited by DNA-Encoded Antibody Prophylaxis and DNA Vaccination Against Chikungunya Virus". J Infect Dis 214, 369-378, (2016).
Nelson, A. L., Dhimolea, E. & Reichert, J. M. "Development trends for human monoclonal antibody therapeutics". Nat Rev Drug Discov 9, 767-774, (2010).
O'Neill, J. "Tackling Drug-Resistant Infections Globally: Final Report and Recommendations" (2016).
Patel Ami et al: "An engineered bispecific DNA-encoded IgG antibody protects against Pseudomonas aeruginosa in a pneumonia challenge model", Sep. 21, 2017 (Sep. 21, 2017), Nature Communications, vol. 8, Page(s) Article No. 637, XP002795431, ISSN: 2041-1723.
Perez, N. et al. "Regulatable systemic production of monoclonal antibodies by in vivo muscle electroporation". Genet Vaccines Ther 2, 2, (2004).
Rice, L. B. "Federal funding for the study of antimicrobial resistance in nosocomial pathogens: no Eskape". J Infect Dis 197, 1079-1081, (2008).
Sardesai, N. Y. & Weiner, D. B. "Electroporation delivery of DNA vaccines: prospects for success". Curr Opin Immunol 23, 421-429, (2011).
Schmaljohn, C. S., Spik, K. W. & Hooper, J. W. "DNA vaccines for HFRS: laboratory and clinical studies". Virus research 187, 91-96, (2014).
Schneider, R., Campbell, M., Nasioulas, G., Felber, B. K. & Pavlakis, G. N. "Inactivation of the human immunodeficiency virus type 1 inhibitory elements allows Rev-independent expression of Gag and Gag/protease and particle formation". J Virol 71, 4892-4903 (1997).
Scott, A. M., Wolchok, J. D. & Old, L. J. "Antibody therapy of cancer". Nat Rev Cancer 12, 278-287, (2012).
Ter Meulen, J. "Monoclonal antibodies in infectious diseases: clinical pipeline in 2011". Infect Dis Clin North Am 25, 789-802, (2011).
Thaden, J. T. et al. "Pseudomonas aeruginosa Bacteremic Patients Exhibit Nonprotective Antibody Titers Against Therapeutic Antibody Targets PcrV and Psl Exopolysaccharide". J Infect Dis 213, 640-648, (2016).
Tjelle, T. E. et al. "Monoclonal antibodies produced by muscle after plasmid injection and electroporation". Molecular therapy : the journal of the American Society of Gene Therapy 9, 328-336, (2004).
Warrener Paul et al: "A novel anti-PcrV antibody providing enhanced protection against Pseudomonas aeruginosa in multiple animal infection models.", Aug. 2014 (Aug. 2014), Antimicrobial Agents and Chemotherapy Aug. 2014, vol. 58, NR. 8, pp. 4384-4391, XP002795430, ISSN: 1098-6596.
Weiner, L. M., Surana, R. & Wang, S. "Monoclonal antibodies: versatile platforms for cancer immunotherapy". Nat Rev Immunol 10, 317-327, (2010).
Williams, J. A. "Vector Design for Improved DNA Vaccine Efficacy, Safety and Production". Vaccines 1, 225-249, (2013).
Zegans, M. E. et al. "Association of Biofilm Formation, Psl Exopolysaccharide Expression, and Clinical Outcomes in Pseudomonas aeruginosa Keratitis: Analysis of Isolates in the Steroids for Corneal Ulcers Trial". JAMA Ophthalmol 134, 383-389, (2016).
Zumla, A. et al. "Host-directed therapies for infectious diseases: current status, recent progress, and future prospects". Lancet Infect Dis 16, e47-63, (16)00078-5 (2016).

* cited by examiner

A

DNA ANTIBODY CONSTRUCTS FOR USE AGAINST *Pseudomonas aeruginosa*

CROSS REFERENCE TO RELATED APPLICATIONS

This application is the U.S. national stage application filed under 35 U.S.C. § 371 claiming benefit to International Patent Application No. PCT/US17/31449, filed May 5, 2017, which claims priority to U.S. Provisional Application No. 62/332,363, filed May 5, 2016, each of which is incorporated by reference herein in its entirety.

TECHNICAL FIELD

The present invention relates to a composition comprising a recombinant nucleic acid sequence for generating one or more synthetic antibodies, including anti-PcrV and bispecific anti-PcrV anti-Psl antibodies, and functional fragments thereof, in vivo, and a method of preventing and/or treating bacterial infection in a subject by administering said composition.

BACKGROUND

Multidrug-resistant (MDR) *Pseudomonas* spp. are among the most difficult pathogens to treat. Infections by *Pseudomonas* spp. are a leading cause of acute pneumonia and chronic lung infections in individuals with cystic fibrosis, and are the most common source of infections of burn wounds or other injuries where they can lead to septic mortality. *Pseudomonas* spp. are able to attach to the surfaces of medical devices such as medical implants, catheters, and artificial joints and cause multiple problems, for example clogging a catheter or physically damaging an implant. *Pseudomonas*, as biofilm forming bacteria, are highly resistant to high levels of antibiotics. Currently, therapeutic antibodies are approved for treatment of multiple diseases. Unfortunately, manufacture and delivery of purified antibodies is cost-prohibitive. Furthermore, these antibody therapies must be re-administered weekly-to-monthly—a challenging consideration in treatment of chronic conditions such as prevention or treatment of biofilm formation on a medical implant.

Thus there is need in the art for improved therapeutics that prevent and/or treat *Pseudomonas aeruginosa* infection and biofilm formation. The current invention satisfies this need.

SUMMARY

In one embodiment, the present invention is directed to a nucleic acid molecule encoding one or more DNA monoclonal antibody (DMAb), wherein the nucleic acid molecule comprises one or more of a) a nucleotide sequence encoding one or more of a variable heavy chain region and a variable light chain region of an anti-PcrV DMAb (DMAb-αPcrV), or a fragment or homolog thereof; b) a nucleotide sequence encoding one or more of a variable heavy chain region and a variable light chain region of an anti-Psl DMAb (DMAb-αPsl), or a fragment or homolog thereof; and c) a nucleotide sequence encoding one or more of a variable heavy chain region and a variable light chain region of a bispecific anti-PcrV anti-Psl DMAb (DMAb-BiSPA), or a fragment or homolog thereof.

In one embodiment, the nucleic acid molecule further comprises a nucleotide sequence encoding a cleavage domain.

In one embodiment, the nucleic acid molecule encoding one or more of a variable heavy chain region and a variable light chain region of a DMAb-αPcrV, or a fragment or homolog thereof, is one or more of a) a nucleotide sequence encoding an amino acid sequence having at least about 95% identity over an entire length of the amino acid sequence to an amino acid sequence selected from the group consisting of SEQ ID NO:2, SEQ ID NO: 4, SEQ ID NO:6, SEQ ID NO:8; SEQ ID NO:10; SEQ ID NO:12; SEQ ID NO:14 and SEQ ID NO:16; b) a nucleotide sequence encoding an amino acid sequence selected from the group consisting of SEQ ID NO:2, SEQ ID NO: 4, SEQ ID NO:6, SEQ ID NO:8; SEQ ID NO:10; SEQ ID NO:12; SEQ ID NO:14 and SEQ ID NO:16; c) a nucleotide sequence encoding a fragment of an amino acid sequence having at least about 95% identity over an entire length of the amino acid sequence to an amino acid sequence selected from the group consisting of SEQ ID NO:2, SEQ ID NO: 4, SEQ ID NO:6, SEQ ID NO:8; SEQ ID NO:10; SEQ ID NO:12; SEQ ID NO:14 and SEQ ID NO:16; d) a nucleotide sequence encoding a fragment of an amino acid sequence selected from the group consisting of SEQ ID NO:2, SEQ ID NO: 4, SEQ ID NO:6, SEQ ID NO:8; SEQ ID NO:10; SEQ ID NO:12; SEQ ID NO:14 and SEQ ID NO:16; e) a nucleotide sequence having at least about 95% identity over an entire length of the nucleotide sequence to a nucleotide sequence selected from the group consisting of SEQ ID NO:1, SEQ ID NO: 3, SEQ ID NO:5, SEQ ID NO:7; SEQ ID NO:9; SEQ ID NO:11; SEQ ID NO:13 and SEQ ID NO:15; f) a fragment of a nucleotide sequence having at least about 95% identity over an entire length of the nucleotide sequence to a nucleotide sequence selected from the group consisting of SEQ ID NO:1, SEQ ID NO: 3, SEQ ID NO:5, SEQ ID NO:7; SEQ ID NO:9; SEQ ID NO:11; SEQ ID NO:13 and SEQ ID NO:15; g) a nucleotide sequence selected from the group consisting of SEQ ID NO:1, SEQ ID NO: 3, SEQ ID NO:5, SEQ ID NO:7; SEQ ID NO:9; SEQ ID NO:11; SEQ ID NO:13 and SEQ ID NO:15; and h) a fragment of a nucleotide sequence selected from the group consisting of SEQ ID NO:1, SEQ ID NO: 3, SEQ ID NO:5, SEQ ID NO:7; SEQ ID NO:9; SEQ ID NO:11; SEQ ID NO:13 and SEQ ID NO:15.

In one embodiment, the nucleic acid molecule encoding one or more of a variable heavy chain region and a variable light chain region of a DMAb-αPsl, or a fragment or homolog thereof, is one or more of a) a nucleotide sequence encoding an amino acid sequence having at least about 95% identity over an entire length of the amino acid sequence to an amino acid of SEQ ID NO:20; b) a nucleotide sequence encoding an amino acid sequence of SEQ ID NO:20; c) a nucleotide sequence encoding a fragment of an amino acid sequence having at least about 95% identity over an entire length of the amino acid sequence to an amino acid sequence of SEQ ID NO:20; d) a nucleotide sequence encoding a fragment of an amino acid sequence of SEQ ID NO:20; e) a nucleotide sequence having at least about 95% identity over an entire length of the nucleotide sequence to SEQ ID NO:19; e) a fragment of a nucleotide sequence having at least about 95% identity over an entire length of the nucleotide sequence to SEQ ID NO:19; f) a nucleotide sequence of SEQ ID NO:19; and g) a fragment of a nucleotide sequence of SEQ ID NO:19.

In one embodiment, the nucleic acid molecule encoding one or more of a variable heavy chain region and a variable light chain region of a DMAb-BiSPA, or a fragment or homolog thereof, is one or more of a) a nucleotide sequence encoding an amino acid sequence having at least about 95% identity over an entire length of the amino acid sequence to an amino acid sequence selected from the group consisting of SEQ ID NO:18 and SEQ ID NO:22; b) a nucleotide sequence encoding an amino acid sequence selected from the group consisting of SEQ ID NO:18 and SEQ ID NO:22; c) a nucleotide sequence encoding a fragment of an amino acid sequence having at least about 95% identity over an entire length of the amino acid sequence to an amino acid sequence selected from the group consisting of SEQ ID NO:18 and SEQ ID NO:22; d) a nucleotide sequence encoding a fragment of an amino acid sequence selected from the group consisting of SEQ ID NO:18 and SEQ ID NO:22; e) a nucleotide sequence having at least about 95% identity over an entire length of the nucleotide sequence to a nucleotide sequence selected from the group consisting of SEQ ID NO:17 and SEQ ID NO:19; f) a fragment of a nucleotide sequence having at least about 95% identity over an entire length of the nucleotide sequence to a nucleotide sequence selected from the group consisting of SEQ ID NO:17 and SEQ ID NO:19; g) a nucleotide sequence selected from the group consisting of SEQ ID NO:17 and SEQ ID NO:19; and h) a fragment of a nucleotide sequence selected from the group consisting of SEQ ID NO:17 and SEQ ID NO:19.

In one embodiment, the nucleic acid molecule further comprises a nucleotide sequence encoding an IRES element. In one embodiment, the IRES element is selected from the group consisting of a viral IRES and an eukaryotic IRES.

In one embodiment, the nucleic acid molecule further comprises a nucleotide sequence encoding a leader sequence.

In one embodiment, the nucleic acid molecule comprises an expression vector.

In one embodiment, the present invention is directed to a composition comprising a nucleic acid molecule encoding one or more DNA monoclonal antibody selected from DMAb-αPcrV, DMAb-αPsl, DMAb-BiSPA, or a fragment, or a homolog thereof.

In one embodiment, the composition further comprises a pharmaceutically acceptable excipient.

In one embodiment, the present invention is directed to a method of preventing or treating a disease in a subject, the method comprising administering to the subject a nucleic acid molecule or composition comprising one or more DNA monoclonal antibody selected from DMAb-αPcrV, DMAb-αPsl, DMAb-BiSPA, or a fragment, or a homolog thereof.

In one embodiment, the disease is a *Pseudomonas aeruginosa* infection.

In one embodiment, the method, further comprises administering an antibiotic agent to the subject. In one embodiment, an antibiotic is administered less than 10 days after administration of the nucleic acid molecule or composition.

In one embodiment, the present invention is directed to a method of preventing or treating a biofilm formation in a subject, the method comprising administering to the subject a nucleic acid molecule or composition comprising one or more DNA monoclonal antibody selected from DMAb-αPcrV, DMAb-αPsl, DMAb-BiSPA, or a fragment, or a homolog thereof.

In one embodiment, the biofilm is a *Pseudomonas aeruginosa* biofilm.

In one embodiment, the method further comprises administering an antibiotic agent to the subject. In one embodiment, an antibiotic is administered less than 10 days after administration of the nucleic acid molecule or composition.

In one embodiment, the present invention relates to a composition comprising a nucleic acid molecule encoding one or more DNA monoclonal antibody that is bispecific for generating one or more antibodies in vivo, wherein the nucleic acid molecule comprises one or more of a) a nucleotide sequence encoding one or more of a variable heavy chain region and a variable light chain region of a first antigen, or a fragment or homolog thereof; and b) a nucleotide sequence encoding one or more of a variable heavy chain region and a variable light chain region of a second antigen, or a fragment or homolog thereof.

In one embodiment, the bispecific antibody molecule according to the invention may have two binding sites of any desired specificity. In some embodiments one of the binding sites is capable of binding a tumor associated antigen. In some embodiment, one of the binding sites is capable of binding a cell surface marker on an immune cell.

In one embodiment, the bispecific antibody of the invention targets CD19/CD3, HER3/EGFR, TNF/IL-17, IL-1a/IL1β, IL-4/IL-13, HER2/HER3, GP100/CD3, ANG2/VEGFA, CD19/CD32B, TNF/IL17A, IL-17A/IL17E, CD30/CD16A, CD19/CD3, CEA/CD3, HER2/CD3, CD123/CD3, GPA33/CD3, EGRF/CD3, PSMA/CD3, CD28/NG2, CD28/CD20, EpCAM/CD3, or MET/EGFR, among others.

BRIEF DESCRIPTION OF THE DRAWINGS

FIG. 1, comprising FIG. 1A through FIG. 1C. depicts the results of exemplary experiments demonstrating DMAb delivery and in vitro expression.

FIG. 2, comprising FIG. 2A through FIG. 2D. depicts the results of exemplary experiments demonstrating expression of DMAb-αPcrV and DMAb-BiSPA in mouse skeletal muscle. BALB/c mice received a DNA injection, in the TA muscle with DMAb-αPcrV or DMAb-BiSpA DNA followed by in vivo electroporation.

FIG. 3, comprising FIG. 3A depicts the results of exemplary experiments demonstrating serum levels of human IgG monitored over 120 days for B6.Cg-Foxn1<nu>3 mice (n=5/group) administered 100 μg of DMAb-αPcrV by IM-EP. FIG. 3B depicts the results of exemplary experiments demonstrating day 7 serum levels in BALB/c mice (n=10/group) administered 100 pg and 300 μg of DMAb-αPcrV. FIG. 3C depicts the results of exemplary experiments demonstrating day 7 serum binding to PcrV protein in BALB/c mice (n=10/group) administered 100 pg of DMAb-αPcrV. FIG. 3D depicts the results of exemplary experiments demonstrating serum levels of human IgG monitored over 120 days for B6.Cg-Foxn1$^{nu}$/J mice (n=5/group) administered 100 μg of DMAb-BiSPA by IM-EP. FIG. 3E depicts the results of exemplary experiments demonstrating day 7 serum levels in BALB/c mice (n=10/group) administered 100 μg and 300 μg of DMAb-BiSPA. FIG. 3F depicts the results of exemplary experiments demonstrating day 7 serum binding to PcrV protein in BALB/c mice (n=10/group) administered 100 μg of DMAb-BiSPA.

FIG. 4, comprising FIG. 4A through Fibure 4C, depicts the results of exemplary experiments demonstrating the pharmacokinetics of DMAb-αPcrV, DMAb-BiSPA, and a mouse IgG2a DMAb in BALB/c mice. BALB/c mice received a 100 μg DNA injection of DMAb into the TA muscle, followed by in vivo electroporation (n=10/group). Serum human IgG1 levels were monitored for 21 days following DMAb injection and quantified by ELISA. Mouse IgG2a levels were monitored for 103 days following DMAb injection and quantified by ELISA.

FIG. 5, comprising FIG. 5A depicts the results of exemplary experiments demonstrating the serum IgG levels of BALB/c mice administered 300 μg of DMAb-αPcrV, DMAb-BiSPA, or ABC123 IgG (2 mg/kg). n=5 mice/group. 2 animals from the DMAb-BiSPA were below the limit of detection of the anti-cytotoxic activity assay. Antibody levels are representative of DMAb in serum on the day of challenge. FIG. 5B depicts the results of exemplary experiments demonstrating in vivo protection in BALB/c mice following administration of control DMAb-DVSF3 (black open circles), DMAb-αPcrV (red circle), DMAb-BiSPA (green circle) or on day −5 or purified ABC123 mAb (purple circle) on day −1 before lethal challenge (data represented is from 2 independent experiments, n=8/group/experiment, total n=16). FIG. 5C depicts the results of exemplary experiments demonstrating protection with different doses of DMAb-BiSPA: 100 μg (purple circle), 200 μg (green circle), 300 μg (red circle), or DMAb-DVSF3 (control). n=8 mice/group. FIG. 5D depicts the results of exemplary experiments demonstrating serum DMAb concentrations with different doses of DMAb-BiSPA. n=8 mice/group.

FIG. 6, comprising FIG. 6A depicts the results of exemplary experiments demonstrating that organ burden of *P. aeruginosa* bacteria (CFU/mL) was quantified from lung, spleen, and kidneys following lethal pneumonia challenge in animals treated with DMAb-DVSF3, DMAb-αPcrV, DMAb-ABC123, or ABC123 IgG. FIG. 6B depicts the results of exemplary experiments demonstrating lung weight in infected animals following DMAb-treatment. FIG. 6C depicts the results of exemplary experiments demonstrating levels of pro-inflammatory cytokines and chemokines in lung homogenates of DMAb-treated animals following lethal challenge. For FIG. 6A through FIG. 6C, n=8 mice/group. The line represents the mean value. Box and whisker plots display all points and bars indicate minimum to maximum values. FIG. 6D depicts the results of exemplary experiments demonstrating serum IgG levels of DMAb and ABC123 IgG in uninfected animals compared with infected animals at 24 hours following lethal pneumonia challenge.

FIG. 7, comprising FIG. 7A depicts the results of exemplary experiments demonstrating post-electroporation with DMAb-DVSF3 showing coalescing areas of marked alveolar infiltrate and hemorrhage (10× magnification). FIG. 7B depicts the results of exemplary experiments demonstrating alveoli have marked neutrophilic infiltrates, hemorrhage and areas of necrosis (inset). FIG. 7C depicts the results of exemplary experiments demonstrating mild pneumonia and occasional bronchiolar debris with DMAb-αPcrV (10× magnification). FIG. 7D depicts the results of exemplary experiments demonstrating alveolar infiltrates comprised of mixed neutrophilic and macrophage populations (inset). FIG. 7E depicts the results of exemplary experiments demonstrating mild alveolitis in the DMAb-BiSPA group (10× magnification). FIG. 7F depicts the results of exemplary experiments demonstrating primarily neutrophilic infiltrates and mild hemorrhage in alveolar spaces (inset). FIG. 7G depicts the results of exemplary experiments demonstrating ABC123 IgG control demonstrates moderate alveolitis (10× magnification). FIG. 7H depicts the results of exemplary experiments demonstrating Alveolar spaces contain neutrophils admixed with cellular debris and hemorrhage (inset). Representative data from 5 mice/group.

FIG. 8, comprising FIG. 8A depicts the results of exemplary experiments demonstrating BALB/c mice were injected with control DMAb-DVSF3 (100 μg), saline+meropenem (MEM, 2.3 mg/kg), DMAb-BiSPA (100 μg), or DMAb-BiSPA (100 μg)+MEM (2.3 mg/kg) and then challenged with a lethal dose of *P. aeruginosa* 6077. MEM was administered 1 hour post-lethal challenge. Animals were monitored for 144 hours post-infection. n=8 mice/group. FIG. 7B depicts the results of exemplary experiments demonstrating DMAb serum levels in animals before lethal challenge. n=8 mice/group. The line represents the mean value and error bars represent standard deviation.

DETAILED DESCRIPTION

Figure 1A:
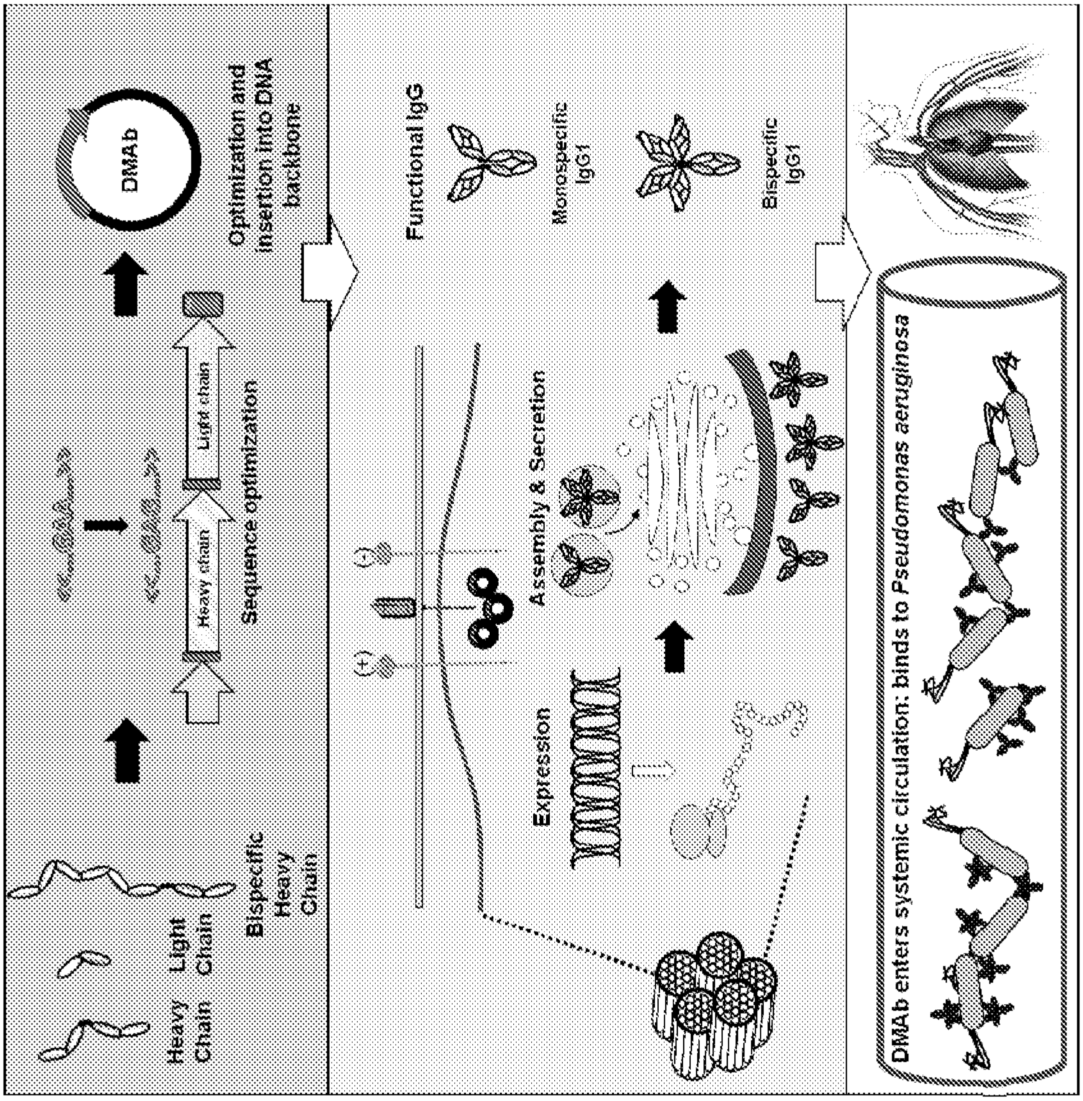
FIG. 1A depicts a schematic diagram demonstrating that DMAbs were designed to encode IgG antibody heavy and light chains of monoclonal antibody clones V2L2MD and ABC123, resulting in the DMAb-αPcrV and DMAb-BiSPA constructs. The optimized DMAb constructs are administered to mice by in vivo IM-EP, and muscle cells being to synthesize an produce mAb. Fully functional DMAb is secreted and enters the systemic circulation.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may refer to a nucleotide sequence (e.g., RNA or DNA) or a nucleic acid molecule comprising a nucleic acid sequence which encodes an antibody as set forth herein. In one embodiment, a coding sequence comprises a DNA sequence from which an RNA sequence encoding an antibody is transcribed. In one embodiment, a coding sequence comprises an RNA sequence encoding an antibody. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule from which an RNA molecule is transcribed. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed. In one embodiment the genetic construct comprises an RNA sequence transcribed from a DNA sequence described herein. For example, in one embodiment, the genetic construct comprises an RNA molecule transcribed from a DNA molecule comprising a sequence encoding an antibody of the invention, a variant thereof or a fragment thereof.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be at least 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be at least 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The invention is based, in part, on the generation of novel sequences for use for producing monoclonal or bispecific antibodies in mammalian cells. In one embodiment, the sequences are for delivery in DNA or RNA vectors including bacterial, yeast, as well as viral vectors. The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding an anti-PcrV antibody (DMAb-αPcrV). In one embodiment, the nucleotide sequence encoding DMAb-αPcrV comprises codon optimized nucleic acid sequences encoding a variable VH or VL regions of a DMAb-αPcrV. In one embodiment, a nucleotide sequence encoding a variable VH region of a DMAb-αPcrV encodes an amino acid sequence as set forth in SEQ ID NO: 2. In one embodiment, a nucleotide sequence encoding a variable VL region of a DMAb-αPcrV encodes an amino acid sequence as set forth in SEQ ID NO: 4. In one embodiment, a nucleotide sequence encoding a variable VH region of a DMAb-αPcrV encodes an amino acid sequence as set forth in SEQ ID NO: 12. In one embodiment, a nucleotide sequence encoding a variable VL region of a DMAb-αPcrV encodes an amino acid sequence as set forth in SEQ ID NO: 16.

In one embodiment, a nucleotide sequence encoding an anti-PcrV antibody encodes a variable VH region as set forth in SEQ ID NO:2 and a variable VL region as set forth in SEQ ID NO:4. In one embodiment, a nucleotide sequence encoding an anti-PcrV antibody encodes a variable VH region as set forth in SEQ ID NO:12 and a variable VL region as set forth in SEQ ID NO:16. In one embodiment, a nucleotide sequence encoding an anti-PcrV antibody encodes an amino acid sequence selected from SEQ ID NO:6, SEQ ID NO:8, SEQ ID NO:10 and SEQ ID NO:14.

In one embodiment, a nucleotide sequence encoding a variable VH region of a DMAb-αPcrV comprises a sequence as set forth in SEQ ID NO:1. In one embodiment, a nucleotide sequence encoding a variable VL region of a DMAb-αPcrV comprises a sequence as set forth in SEQ ID NO:3. In one embodiment, the nucleotide sequence encoding the variable VH region of a DMAb-αPcrV comprises a nucleotide sequence as set forth in SEQ ID NO:11. In one embodiment, a nucleotide sequence encoding a variable VL region of a DMAb-αPcrV comprises a sequence as set forth in SEQ ID NO:15.

In one embodiment, a nucleotide sequence encoding DMAb-αPcrV comprises a variable VH sequence as set forth in SEQ ID NO:1 and a variable VL sequence as set forth in SEQ ID NO:3. In one embodiment, a nucleotide sequence encoding DMAb-αPcrV comprises a variable VH sequence as set forth in SEQ ID NO:11 and a variable VL sequence as set forth in SEQ ID NO:15. In one embodiment, a nucleotide sequence encoding DMAb-αPcrV comprises a sequence selected from SEQ ID NO:5, SEQ ID NO:7, SEQ ID NO:9 and SEQ ID NO:13.

In one embodiment, a nucleotide sequence encoding a DMAb-αPcrV is operably linked to a sequence encoding a leader sequence. In various embodiments, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16 operably linked to a leader sequence are as set forth in SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41, respectively.

In one embodiment, the nucleic acid molecule comprises a nucleotide sequence encoding an anti-Psl antibody (DMAb-αPsl). In one embodiment, the nucleotide sequence encoding DMAb-αPsl comprises codon optimized nucleic acid sequences encoding the variable VH and VL regions of DMAb-αPsl. In one embodiment, the nucleotide sequence encoding DMAb-αPsl comprises codon optimized nucleic acid sequences encoding the variable VH and VL regions of DMAb-αPsl. In one embodiment, a nucleotide sequence encoding DMAb-αPsl encodes an amino acid sequence as set forth in SEQ ID NO:20. In one embodiment, a nucleotide sequence encoding DMAb-αPsl comprises a nucleotide sequence as set forth in SEQ ID NO:19.

In one embodiment, a nucleotide sequence encoding a DMAb-αPsl is operably linked to a sequence encoding a leader sequence. In various embodiments, SEQ ID NO:19 and SEQ ID NO:20 operably linked to a leader sequence are as set forth in SEQ ID NO:44 and SEQ ID NO:45 respectively.

In one embodiment, the nucleic acid molecule comprises a nucleotide sequence encoding a bispecific antibody. In one embodiment, a bispecific antibody is an anti-PcrV and anti-Psl bispecific antibody (DMAb-BiSPA). In one embodiment, the nucleotide sequence encoding DMAb-BiSPA comprises codon optimized nucleic acid sequences encoding the variable VH and VL regions of DMAb-BiSPA. In one embodiment, a nucleotide sequence encoding DMAb-BiSPA encodes an amino acid sequence selected from SEQ ID NO:18 and SEQ ID NO:22. In one embodiment, the nucleotide sequence encoding DMAb-BiSPA comprises a nucleotide sequence selected from SEQ ID NO:17 and SEQ ID NO:21.

In one embodiment, a nucleotide sequence encoding a bispecific antibody is operably linked to a sequence encoding a leader sequence. In various embodiments, SEQ ID NO:17, SEQ ID NO:18, SEQ ID NO:21, and SEQ ID NO:22 operably linked to a leader sequence are as set forth in SEQ ID NO:42, SEQ ID NO:43, SEQ ID NO:46 and SEQ ID NO:47 respectively.

In one embodiment, the nucleic acid molecule comprises an RNA molecule comprising a ribonucleotide sequence. In one embodiment, the RNA molecule comprises a nucleotide sequence encoding an amino acid sequence selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, from SEQ ID NO:22, SEQ ID NO:27, SEQ ID NO:29, SEQ ID NO:31, SEQ ID NO:33, SEQ ID NO:35, SEQ ID NO:37, SEQ ID NO:39; SEQ ID NO:41, SEQ ID NO:43, SEQ ID NO:45 and SEQ ID NO:47. In one embodiment, the RNA molecule comprises a transcript generated from a DNA molecule comprising a nucleotide sequence encoding an amino acid sequence selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, from SEQ ID NO:22, SEQ ID NO:27, SEQ ID NO:29, SEQ ID NO:31, SEQ ID NO:33, SEQ ID NO:35, SEQ ID NO:37, SEQ ID NO:39; SEQ ID NO:41, SEQ ID NO:43, SEQ ID NO:45 and SEQ ID NO:47. In one embodiment, the RNA molecule comprises a transcript generated from a DNA molecule comprising a nucleotide sequence selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, from SEQ ID NO:21, SEQ ID NO:26, SEQ ID NO:28, SEQ ID NO:30, SEQ ID NO:32, SEQ ID NO:34, SEQ ID NO:36, SEQ ID NO:38; SEQ ID NO:40, SEQ ID NO:42, SEQ ID NO:44 and SEQ ID NO:46.

The composition of the invention can treat, prevent and/or protect against any disease, disorder, or condition associated with a bacterial activity. In certain embodiments, the composition can treat, prevent, and or/protect against bacterial infection. In certain embodiments, the composition can treat, prevent, and or/protect against bacterial biofilm formation. In certain embodiments, the composition can treat, prevent, and or/protect against *Pseudomonas aeruginosa* infection. In certain embodiments, the composition can treat, prevent, and or/protect against *Pseudomonas aeruginosa* biofilm formation. In certain embodiments, the composition can treat, prevent, and or/protect against sepsis.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. In one embodiment, the synthetic antibody can provide increased survival of the disease in the subject over the expected survival of a subject having the disease who has not been administered the synthetic antibody. In various embodiments, the synthetic antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the synthetic antibody can provide increased protection against the disease in the subject over the expected protection of a subject who has not been administered the synthetic antibody. In various embodiments, the synthetic antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

a. Bispecific Antibodies

As described elsewhere herein, the composition can comprise a recombinant nucleic acid sequence. The recombinant nucleic acid sequence can encode a bispecific antibody, a fragment thereof, a variant thereof, or a combination thereof. The antibody is described in more detail below. The invention provides novel bispecific antibodies comprising a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

In one embodiment, the bispecific antibody is a bivalent antibody comprising a) a first light chain and a first heavy chain of an antibody specifically binding to a first antigen, and b) a second light chain and a second heavy chain of an antibody specifically binding to a second antigen.

A bispecific antibody molecule according to the invention may have two binding sites of any desired specificity. In some embodiments one of the binding sites is capable of binding a tumor associated antigen. In some embodiments the binding site included in the Fab fragment is a binding site specific for a tumor associated surface antigen. In some embodiments the binding site included in the single chain Fv fragment is a binding site specific for a tumor associated antigen such as a tumor associated surface antigen.

The term "tumor associated surface antigen" as used herein refers to an antigen that is or can be presented on a surface that is located on or within tumor cells. These antigens can be presented on the cell surface with an extracellular part, which is often combined with a transmembrane and cytoplasmic part of the molecule. These antigens can in some embodiments be presented only by tumor cells and not by normal, i.e. non-tumor cells. Tumor antigens can be exclusively expressed on tumor cells or may represent a tumor specific mutation compared to non-tumor cells. In such an embodiment a respective antigen may be referred to as a tumor-specific antigen. Some antigens are presented by both tumor cells and non-tumor cells, which may be referred to as tumor-associated antigens. These tumor-associated antigens can be overexpressed on tumor cells when compared to non-tumor cells or are accessible for antibody binding in tumor cells due to the less compact structure of the tumor tissue compared to non-tumor tissue. In some embodiments the tumor associated surface antigen is located on the vasculature of a tumor.

Illustrative examples of a tumor associated surface antigen are CD10, CD19, CD20, CD22, CD33, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, CD133, IL3R, fibroblast activating protein (FAP), CDCP1, Derlin1, Tenascin, frizzled 1-10, the vascular antigens VEGFR2 (KDR/FLK1), VEGFR3 (FLT4, CD309), PDGFR-.alpha. (CD140a), PDGFR-.beta. (CD140b) Endoglin, CLEC14, Teml-8, and Tie2. Further examples may include A33, CAMPATH-1 (CDw52), Carcinoembryonic antigen (CEA), Carboanhydrase IX (MN/CA IX), CD21, CD25, CD30, CD34, CD37, CD44v6, CD45, CD133, de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72. Examples of antigens expressed on the extracellular matrix of tumors are tenascin and the fibroblast activating protein (FAP).

In some embodiments, one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally monovalent, encompassing .alpha.- and .beta.-chains, in some embodiments it encompasses .gamma-chains and .delta-chains (supra). Accordingly, in some embodiments the TCR is TCR (alpha/beta) and in some embodiments it is TCR (gamma/delta). The T cell receptor forms a complex with the CD3 T-Cell co-receptor. CD3 is a protein complex and is composed of four distinct chains. In mammals, the complex contains a CD3.gamma. chain, a CD36 chain, and two CD3E chains. These chains associate with a molecule known as the T cell receptor (TCR) and the .zeta.-chain to generate an activation signal in T lymphocytes. Hence, in some embodiments a T-cell specific receptor is the CD3 T-Cell co-receptor. In some embodiments a T-cell specific receptor is CD28, a protein that is also expressed on T cells. CD28 can provide co-stimulatory signals, which are required for T cell activation. CD28 plays important roles in T-cell proliferation and survival, cytokine production, and T-helper type-2 development. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments the first binding site of the antibody molecule binds a tumor associated surface antigen and the second binding site binds a T cell specific receptor molecule and/or a natural killer (NK) cell specific receptor molecule. In some embodiments the first binding site of the antibody molecule binds one of A33, CAMPATH-1 (CDw52), Carcinoembryonic antigen (CEA), Carboanhydrase IX (MN/CA IX), CD10, CD19, CD20, CD21, CD22, CD25, CD30, CD33, CD34, CD37, CD44v6, CD45, CD133, CDCP1, Her3, chondroitin sulfate proteoglycan 4 (CSPG4, melanoma-associated chondroitin sulfate proteoglycan), CLEC14, Derlin1, Epidermal growth factor receptor (EGFR), de2-7 EGFR, EGFRvIII, EpCAM, Endoglin, Ep-CAM, Fibroblast activation protein (FAP), Folate-binding protein, G250, Fms-like tyrosine kinase 3 (FLT-3, CD135), c-Kit (CD117), CSF1R (CD115), frizzled 1-10, Her2/neu, HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), TAG-72, Tenascin, Teml-8, Tie2 and VEGFR2 (KDR/FLK1), VEGFR3 (FLT4, CD309), PDGFR-.alpha. (CD140a), PDGFR-.beta. (CD140b), and the second binding site binds a T cell specific receptor molecule and/or a natural killer (NK) cell specific receptor molecule. In some embodiments the first binding site of the antibody molecule binds a tumor associated surface antigen and the second binding site binds one of CD3, the T cell receptor (TCR), CD28, CD16, NKG2D, Ox40, 4-1BB, CD2, CD5 and CD95.

In some embodiments the first binding site of the antibody molecule binds a T cell specific receptor molecule and/or a natural killer (NK) cell specific receptor molecule and the second binding site binds a tumor associated surface antigen. In some embodiments the first binding site of the antibody binds a T cell specific receptor molecule and/or a natural killer (NK) cell specific receptor molecule and the second binding site binds one of A33, CAMPATH-1 (CDw52), Carcinoembryonic antigen (CEA), Carboanhydrase IX (MN/CA IX), CD10, CD19, CD20, CD21, CD22, CD25, CD30, CD33, CD34, CD37, CD44v6, CD45, CD133, CDCP1, Her3, chondroitin sulfate proteoglycan 4 (CSPG4, melanoma-associated chondroitin sulfate proteoglycan), CLEC14, Derlin1, Epidermal growth factor receptor (EGFR), de2-7 EGFR, EGFRvIII, EpCAM, Endoglin, Ep-CAM, Fibroblast activation protein (FAP), Folate-binding protein, G250, Fms-like tyrosine kinase 3 (FLT-3, CD135), frizzled 1-10, Her2/neu, HLA-DR, IGFR, IL-2 receptor, IL3R, MCSP (Melanoma-associated cell surface chondroitin sulphate proteoglycane), Muc-1, Prostate-specific membrane antigen (PSMA), Prostate specific antigen (PSA), TAG-72, Tenascin, Teml-8, Tie2 and VEGFR. In some embodiments the first binding site of the antibody binds one of CD3, the T cell receptor (TCR), CD28, CD16, NKG2D, Ox40, 4-1BB, CD2, CD5 and CD95, and the second binding site binds a tumor associated surface antigen.

In one embodiment, the bispecific antibody of the invention targets CD19 and CD3, HER3 and EGFR, TNF and IL-17, IL-1a and IL1β, IL-4 and IL-13, HER2 and HER3, GP100 and CD3, ANG2 and VEGFA, CD19 and CD32B, TNF and IL17A, IL-17A and IL17E, CD30 and CD16A, CD19 and CD3, CEA and CD3, HER2 and CD3, CD123 and CD3, GPA33 and CD3, EGRF and CD3, PSMA and CD3, CD28 and NG2, CD28 and CD20, EpCAM and CD3 or MET and EGFR, among others.

b. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include at least one heterologous nucleic acid sequence or one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCCACC) for increased translation; addition of an immunoglobulin (Ig) leader sequence encoding a signal peptide; and eliminating to the extent possible cis-acting sequence motifs (i.e., internal TATA boxes).

c. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide.

In one embodiment, a signal peptide comprises an amino acid sequence of MDWTWRILFLVAAATGTHA (SEQ ID NO:24). In one embodiment, a signal peptide comprises an amino acid sequence of MVLQTQVFISLLLWISGAYG (SEQ ID NO:25). Exemplary nucleotide sequences encoding antibodies of the invention operably linked to a sequence encoding a signal peptide include, but are not limited to, nucleotide sequences as set forth in SEQ ID NO:26 through SEQ ID NO:47.

The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include the heterologous nucleic acid sequence encoding the protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

d. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

e. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

The recombinant nucleic acid sequence construct may also comprise a sequence encoding a leader sequence. The leader sequence may be 5' of the coding sequence. In one embodiment, the N-terminal leader comprises an amino acid sequence selected from SEQ ID NO: 24 and SEQ ID NO:25. Exemplary nucleic acid and amino acid sequences of the invention operably linked to a leader sequence are set forth in SEQ ID NO:26 through SEQ ID NO:47.

f. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA Vectors

In one embodiment, the nucleic acid molecule of the invention comprises an RNA molecule encoding an antibody of the invention. In one embodiment, the RNA molecule comprises a nucleotide sequence encoding an amino acid sequence selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, from SEQ ID NO:22, SEQ ID NO:27, SEQ ID NO:29, SEQ ID NO:31, SEQ ID NO:33, SEQ ID NO:35, SEQ ID NO:37, SEQ ID NO:39; SEQ ID NO:41, SEQ ID NO:43, SEQ ID NO:45 and SEQ ID NO:47. In one embodiment, the RNA molecule comprises a transcript generated from a DNA molecule comprising a nucleotide sequence encoding an amino acid sequence selected from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, from SEQ ID NO:22, SEQ ID NO:27, SEQ ID NO:29, SEQ ID NO:31, SEQ ID NO:33, SEQ ID NO:35, SEQ ID NO:37, SEQ ID NO:39; SEQ ID NO:41, SEQ ID NO:43, SEQ ID NO:45 and SEQ ID NO:47. In one embodiment, the RNA molecule comprises a transcript generated from a DNA molecule comprising a nucleotide sequence selected from SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, from SEQ ID NO:21, SEQ ID NO:26, SEQ ID NO:28, SEQ ID NO:30, SEQ ID NO:32, SEQ ID NO:34, SEQ ID NO:36, SEQ ID NO:38; SEQ ID NO:40, SEQ ID NO:42, SEQ ID NO:44 and SEQ ID NO:46. Accordingly, in one embodiment, the invention provides an RNA molecule encoding one or more antibody of the invention. The RNA may be plus-stranded. Accordingly, in some embodiments, the RNA molecule can be translated by cells without needing any intervening replication steps such as reverse transcription. A RNA molecule useful with the invention may have a 5' cap (e.g., a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, copending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

3. ANTIBODY

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

b. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγRIa. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγRIa, and thus, the modified antibody does not enhance or cause ADE of disease associated with the antigen, but still neutralizes the antigen.

4. ANTIGEN

The synthetic antibody is directed to the antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a bacterium. The antigen can be associated with bacterial infection. In one embodiment, the antigen can be a bacterial virulence factor.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

a. Bacterial Antigens

The bacterial antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-*Thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an *halophile*, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthraces*, methicillin-resistant *Staphylococcus aureus* (MRSA), or *Clostridium difficile*. The bacterium can be *Pseudomonas aeruginosa.*

(a) *Pseudomonas aeruginosa* Antigens

The bacterial antigen may be a *Pseudomonas aeruginosa* antigen, or fragment thereof, or variant thereof. The *Pseudomonas aeruginosa* antigen can be from a virulence factor. Virulence factors associated with *Pseudomonas aeruginosa* include, but are not limited to structural components, enzymes and toxins. A *Pseudomonas aeruginosa* virulence factor can be one of exopolysaccharide, Adhesin, lipopolysaccharide, Pyocyanin, Exotoxin A, Exotoxin S, Cytotoxin, Elastase, Alkaline protease, Phospholipase C, Rhamnolipid, and components of a bacterial secretion system.

In one embodiment, an antigen is an extracellular polysaccharide (e.g. Alginate, Pel and Psl). In one embodiment, an antigen is one of polysaccharide synthesis locus (psi), a gene contained therein (e.g. pslA, pslB, pslC, pslD, pslE, pslF, pslG, pslH, pslI, pslJ, pslK, pslL, pslM, pslN and pslO), a protein or enzyme encoded therein (e.g. a glycosyl transferase, phosphomannose isomerase/GDP-D-mannose pyrophosphorylase, a transporter, a hydrolase, a polymerase, an acetylase, a dehydrogenase and a topoisomerase) or a product produced therefrom (e.g. Psl exopolysaccharide, referred to as "Psl").

In one embodiment, an antigen is a component of a bacterial secretion system. Six different classes of secretion systems (types I through VI) have been described in bacteria, five of which (types I, II, II, V and VI) are found in gram negative bacteria, including *Pseudomonas aeruginosa*. In one embodiment, an antigen is one of a gene (e.g. an apr or has gene) or protein (e.g. AprD, AprE, AprF, HasD, HasE, HasF and HasR) or a secreted protein (e.g. AprA, AprX and HasAp) of a type I secretion system. In one embodiment, an antigen is one of a gene (e.g. xcpA/pilD, xphA, xqhA, xcpP to Q and xcpR to Z) or protein (e.g. GspC to M, GspAB, GspN, GspO, GspS, XcpT to XcpX, FppA,) or a secreted protein (e.g. LasB, LasA, PlcH, PlcN, PlcB, CbpD, ToxA, PmpA, PrpL, LipA, LipC, PhoA, PsAP, LapA) of a type II secretion system. In one embodiment, an antigen is one of a gene (e.g. a psc, per, pop or exs gene) or protein (e.g. PscC, PscE to PscF, PscJ, PscN, PscP, PscW, PopB, PopD, PcrH and PcrV) or a secreted protein (e.g. ExoS, ExoT, ExoU and ExoY) of a type III secretion system. In one embodiment, an antigen is a regulator of a type III secretion system (e.g. ExsA and ExsC). In one embodiment, an antigen is one of a gene (e.g. estA) or protein (e.g. EstA, CupB3, CupB5 and LepB) or a secreted protein (e.g. EstA, LepA, and CupB5) of a type V secretion system. In one embodiment, an antigen is one of a gene (e.g. a HSI-I, HSI-II and HSI-III gene) or protein (e.g. Fhal, ClpVl, a VgrG protein or a Hcp protein) or a secreted protein (e.g. Hcpl) of a type VI secretion system.

5. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

6. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

7. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

8. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

9. METHOD OF TREATMENT

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

In certain embodiments, the invention provides a method of treating protecting against, and/or preventing a bacterial infection. In one embodiment, the method treats, protects against, and/or prevents formation of a bacterial biofilm. In one embodiment, the method treats, protects against, and/or prevents *Pseudomonas aeruginosa* infection or biofilm formation. In one embodiment, the method treats, protects against, and/or prevents *Pseudomonas aeruginosa* infection of a wound.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

10. USE IN COMBINATION WITH ANTIBIOTICS

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

The present invention has multiple aspects, illustrated by the following non-limiting examples.

11. EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: An Engineered Bispecific, DNA-Encoded IgG Antibody (DMAb) Protects Against *Pseudomonas aeruginosa* in a Lethal Pneumonia Challenge Model The studies presented herein describe the development and analysis of synthetic DMAbs encoding a monospecific anti-PcrV IgG (DMAb-αPcrV) and clinical candidate bispecific antibody ABC123 (DMAb-BiSPA) for in vivo production and activity. DMAb production in vivo can rapidly produce functional and protective titers for both constructs. These DMAbs can persist and have similar potency to bioprocess produced mAbs, along with comparable prevention of *P. aeruginosa* colonisation of major organs.

In the current study, it is demonstrated that mAbs against *P. aeruginosa* can be encoded in synthetic DNA vectors, DMAbs, and produced in vivo by skeletal muscle. The anti-*Pseudomonas* DMAbs bound effectively to therapeutic targets and were protective in a mouse model of lethal pneumonia caused by an aggressive *P. aeruginosa* strain. A single dose of DMAb is transiently expressed for 3-4 months and protection against lethal infection is comparable to treatment of mice with purified IgG. This is a considerable advance for long-term mAb administration as DMAbs can be continuously expressed from muscle until the plasmid is eventually lost. In addition to routine administration, another foreseeable advantage for anti-*P. aeruginosa* DMAbs would be for high-risk patients with recurring infections related to chronic illnesses or implanted devices, where DMAbs may reduce the need for extended antibiotic regimens. Furthermore, it is demonstrated that DMAbs can also function synergistically with a commonly used antibiotic, meropenem. The synergistic effect of DMAb and antibiotic combination suggests that this strategy could have potential in reducing antibiotic treatment regimens, thereby reducing the length of antibiotic exposure in patients. This adjunctive activity is equivalent to that observed with protein IgG in previous studies (DiGiandomenico et al., 2014, *Sci Transl Med* 6, 262ra155). Taken together, these results suggest that DNA delivery of full length IgG mAbs is a promising platform strategy for prevention of serious bacterial infections and possibly for other therapeutic indications. All bioprocessed anti-Pseudomonal IgG mAbs (anti-Psl, anti-PcrV, and ABC123) have been shown to be protective against *P. aeruginosa* clinical isolates derived from diverse serotypes, multiple type 3 secretion phenotypes (cytotoxic vs. invasive strain; ExoU+, ExoS−; ExoU−, ExoS+, respectively), and multiple infection sites (DiGiandomenico et al., 2012, J Exp Med 209, 1273-1287; Warrener et al., 2014, Antimicrob Agents Chemother 58, 4384-4391; DiGiandomenico et al., 2014, Sci Transl Med 6, 262ra155; Thaden et al., 2016, J Infect Dis 213, 640-648; Zegans er al., 2016, JAMA Ophthalmol 134, 383-389).

The Material and Methods are now described

Cell Lines and Bacteria

Human embryonic kidney (HEK) 293T cells were maintained in Dulbecco's Modified Eagle's Medium (DMEM), supplemented with 10% fetal bovine serum (FBS). Cell lines were and were maintained in mycoplasmia-free conditions. Routine testing was performed at the University of Pennsylvania. All cells were maintained at a low passage number. *P. aeruginosa* keratitis clinical isolate 6077 (PA 6077), a cytotoxic ($ExoU^+$) strain, was used for all infection experiments.

DMAb Construction and Expression

The sequences of the single specificity anti-*P. aeruginosa* PcrV protein (clone V2L2MD) (Warrener et al., 2014, Antimicrob Agents Chemother 58, 4384-4391) and engineered bispecific anti-*P. aeruginosa* (dual specificity for PcrV and Psl, clone ABC123) (DiGiandomenico et al., 2014, Sci Transl Med 6, 262ra155) were obtained. The nucleotide sequence for each human IgG1 heavy and Igκ light chains were codon optimized for both mouse and human biases to enhance expression in mammalian cells (Graf et al., 2004, Methods Mol Med 94, 197-210; Deml et al., 2001, *J Virol* 75, 10991-11001). Sequences were also RNA optimized for improved mRNA stability and efficient translation on the ribosome (Schneider et al., 1997, *J Virol* 71, 4892-4903; Andre et al., 1997, J Virol 72, 1497-1503, leading to increase protein yield (Fath et al., 2011, *PLoS One* 6, e17596). The optimized heavy and light chain genes were then inserted into the pGX0001 DNA expression vector, under the control of a human cytomegalovirus (hCMV) promoter and bovine growth hormone (BGH) polyA.

Both genes were encoded in cis, separated by a furin cleavage site and P2A peptide. The result was two plasmids: DMAb-αPcrV and DMAb-BiSPA. HEK 293T cells were transfected with DMAb DNA using GeneJammer (Agilent, Wilmington, Del.) transfection reagent. Cell supernatants and cell lysates were harvested 48 hours post-transfection and assayed for human IgG production by enzyme-linked immunosorbent assay (ELISA) and Western blot.

Mouse Muscle Tissue Immunofluorescence

BALB/c mice were injected with 100 μg of DMAb by IM injection in the TA muscle followed by IM-EP. Tissue was harvested 3 days post-injection, fixed in 4% Neutral-buffered Formalin (BBC Biochemical, Washington State) and immersed in 30% (w/v) sucrose (Sigma, MO) in D.I.water. Tissues were then embedded into O.C.T. compound (Sakura Finetek, CA) and snap-frozen. Frozen tissue blocks were sectioned to a thickness of 18 um. Muscle sectioned were incubated with Blocking-Buffer (0.3% (v/v) Triton-X (Sigma), 2% (v/v) donkey serum in PBS) for 30 min, covered with Parafilm. Goat anti-human IgG-Fc fragment antibody (A-80-104A, Bethyl, Tex.) was diluted 1:100 in incubation buffer (1% (w/v) BSA (Sigma), 2% (v/v) donkey serum, 0.3% (v/v) Triton-X (Sigma) and 0.025% (v/v) 1 g/ml Sodium Azide (Sigma) in PBS). 50 μl of staining solution was added to each section and incubated for 2 hrs. Sections were washed 5 min in 1×PBS three times. Donkey anti-goat IgG AF488 (ab150129, Abcam, USA) was diluted 1:200 in incubation buffer and 50 μl was added to each section. Section were washed after 1 hr incubation and mounted with DAPI-Fluoromount (SouthernBiotech, AL) and covered.

In vivo expression of DMAb constructs was imaged with a BX51 Fluorescent microscope (Olympus) equipped with Retiga3000 monochromatic camera (QImaging).

Human IgG Quantification by ELISA and by Anti-Cytotoxic Activity

Ninety-six well, high-binding immunosorbent plates were coated with 10 μg/mL purified anti-human IgG-Fc and incubated overnight at 4° C. The following day, plates were washed and blocked at room temperature for at least 1 hour with PBS containing 10% FBS. Samples were serially diluted two-fold and transferred to the blocked plate and incubated for 1 hour at room temperature. Purified human IgGκ was used as a standard. Following incubation, samples were probed with an anti-human IgGκ antibody conjugated to horseradish peroxidase at a 1:20 000 dilution. Plates were developed using o-Phenylenediamine dihydrochloride substrate and stopped with 2N $H_2SO_4$. A BioTek Synergy2 plate reader was used to read the plates at OD450 nm. Alternatively, human IgG from serum was quantified as described above with the exception of using an anti-idiotype mAb (0.05 μg/well suspended in 0.2M sodium bicarbonate buffer, pH 9.4) specific for V2L2MD or ABC123 as the capture reagent. Purified V2L2MD or ABC123 was used as a standard.

DMAb was also quantified from serum using 384-well black MaxiSorp plates (coated with 10 μg/mL Goat anti-Human IgG (H+L). Plates were washed and blocked for 1-2 hours at room temperature with Blocker Casein in PBS. After blocking, a standard containing ABC123 or V2L2MD was serially diluted 1:2 across the plate, while serum samples were diluted 1:20, 1:40, 1:80 and 1:160. Plates containing the samples were then incubated for 1 hour at room temperature. After washing, plates were probed with Donkey anti-Human IgG-HRP at a 1:4000 dilution and incubated for 1 hour at room temperature. After washing, the immune reaction was developed by adding SuperSignal ELISA Pico Reagent and fluorescence was read on the Perkin Elmer Envision.

DMAb was also quantified from serum based on anti-cytotoxic activity mediated by DMAb-αPcrV and DMAb-BiSPA that measures the protection of A549 cells from the cytotoxic effects of PA 6077. The activity of mouse serum was compared to a standard curve of naïve mouse serum spiked with V2L2MD IgG.

Binding ELISA

Ninety-six well plates immunosorbent plates were coated overnight with *Pseudomonas* PcrV protein at 0.5 μg/mL. The following day, serum samples from DMAb-administered animals were serially diluted two-fold and then transferred to the blocked plate. Samples were probed with an anti-human IgG H+L antibody conjugated to HRP at a dilution of 1:5000 and developed with OPD substrate.

Western Blot

The cell lysates from DMAb-transfected cells were collected in cell lysis buffer. Samples were centrifuged at 20 000 rpm and the supernatant containing the protein fraction was collected. The samples were quantified using a bicinchoninic acid (BCA) assay and 10 μg total lysate was loaded on a 4-12% Bis-Tris SDS-PAGE gel. The gel was transferred to a nitrocellulose membrane using the iBlot2 system. The membrane was blocked in 5% powdered skim milk+0.5% Tween-20 and then probed using a donkey anti-human H+L antibody conjugated to HRP. Bands were developed using a chemiluminescent system and visualized on film.

Mice

Female, six to eight week old B6.Cg-Foxn1nuJ and BALB/c mice were purchased from The Jackson Laboratory (Bar Harbor, Me.) and housed in the animal facilities at the University of Pennsylvania or MedImmune, AstraZeneca. All animal protocols were approved by the institutional University of Pennsylvania and MedImmune IACUC committees, following guidelines from ALAAC. Further IACUC oversight was provided by The Animal Care and Use Review Office (ACURO). Animals received an intramuscular (IM) pre-injection of hyaluronidase (400U/mL, Sigma Aldrich) 30 minutes-1 hour before IM injection of 100 μg-300 μg DMAb-αPcrV or DMAb-BiSPA in the TA or quad muscles, followed by electroporation (IM-EP). Serum levels of DMAbs were monitored following administration.

Lethal Pneumonia Challenge

BALB/c mice (n=8/group) received 100 μg or 300 μg of DMAb-αPcrV or DMAb-BiSPA by IM-EP at day −5 before challenge. The unrelated dengue virus DMAb-DVSF3[20] was included as a control. A fourth group of animals received an intraperitoneal (IP) injection of purified protein IgG ABC123 (2 mg/kg) on day −1 before challenge. On day 0, animals received an intranasal challenge of 9.75e5-1.0e6 colony forming units (CFU) of the aggressive, anti-microbial resistant *Pseudomonas aeruginosa* strain 6077. Animals were monitored for 6 days following intranasal challenge for survival as described in[16]. Briefly, animals were anesthetized with ketamine and xylazine followed by intranasal administration of the bacterial inoculum contained in 0.05 ml. For organ burden analyses, lungs, spleens and livers were harvested from DMAb-treated animals 24 hours post-infection followed by homogenizing and plating of Luria agar plates for enumeration of bacterial CFU. IL-1β, IL-6 and KC/GRO were quantified from the supernatant of lung homogenates using a multiplex kit (Meso Scale Diagnostics) according to the manufactures instructions. For DMAb and meropenem (MEM) combination experiments, MEM was administered subcutaneously 4 hours after infection.

Histopathology

Lungs were harvested at 48 hours post-infection and fixed in 10% neutral buffered formalin for a minimum of 48 hours. Fixed tissues were then routinely processed and embedded in paraffin, sectioned at 3 μm thickness, and stained with Gill's hematoxylin and eosin for histologic evaluation by a pathologist blinded to the experimental conditions.

Statistics

All statistical analyses were performed using GraphPad Prism 6.0 software or SPSS. Sample size calculations for two independent proportions were calculated with alpha 0.05 and power 0.90. A minimum of n=5 mice was calculated to be needed in order to ensure adequate power. Student's T-test or one-way analysis of variance (ANOVA) calculations, were performed where necessary. Survival data was represented by a Kaplan-Meier survival curve and significance was calculated using a log-rank test and one-way ANOVA with correction for multiple comparisons. The data was considered significant if $p<0.05$. The lines in all graphs represent the mean value and error bars represent the standard deviation. No samples or animals were excluded from the analysis. Randomization was not performed for the animal studies. Samples and animals were not blinded before performing each experiment.

The results of the Experiments are now described

Design and in vitro expression of anti-*P. aeruginosa* DNA-delivered monoclonal antibodies (DMAbs)

Two anti-*P. aeruginosa* mAb genes to be re-encoded for optimal expression into a DNA expression vector system based on their previously described potent protective in vivo activity against lethal *P. aeruginosa* infection. The human immunoglobulin gamma 1 (IgG1) heavy and light chain sequences (Fab and Fc portions) were nucleotide and amino acid sequence optimized taking into consideration both human and mouse codon bias and encoded as a single, polycistronic unit in the pGX0001 DNA plasmid backbone, resulting in two constructs: DMAb-αPcrV and DMAb-BiSPA (FIG. 1A). The heavy and light chain are expressed as a single mRNA transcript and then cleaved post-translationally at a porcine teschovirus-1 2A (P2A) cleavage site. A furin cleavage site (RGRKRRS; SEQ ID NO:23) was also included to ensure complete removal of the P2A from the final in vivo produced antibody.

Figures 1B, 1C:
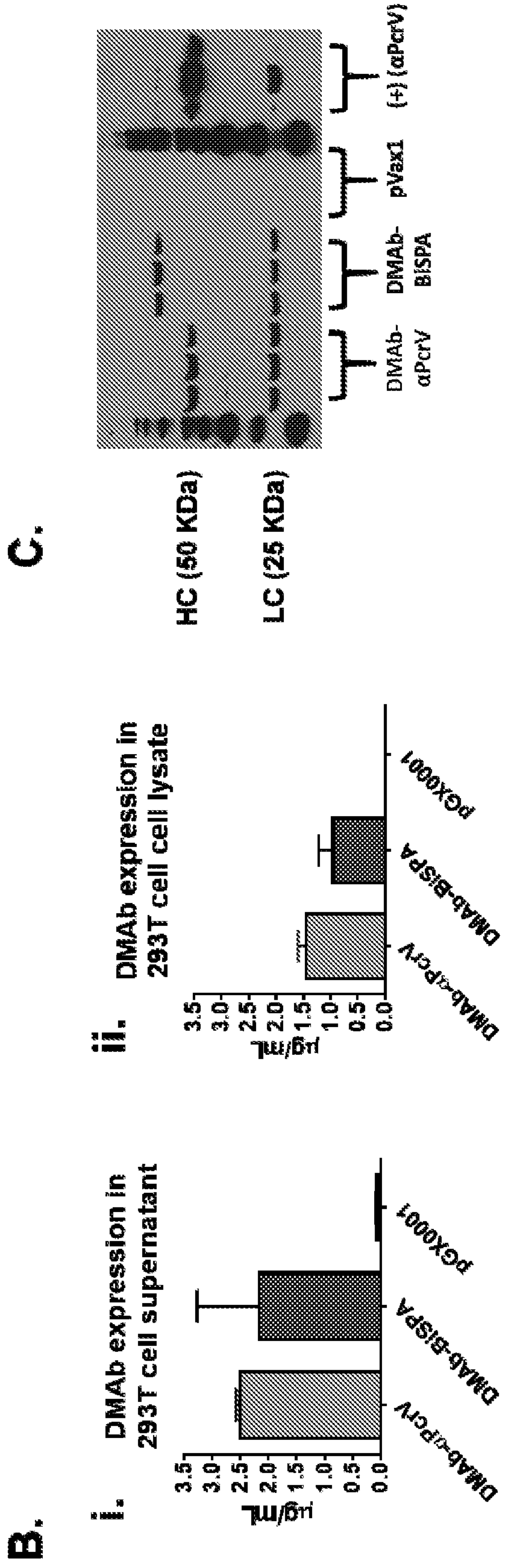
FIG. 1B depicts the results of exemplary experiments demonstrating that HEK 293 T cells were transfected with 1 μg/well of DMAb-αPcrV, DMAb-BiSPA, or control pGX0001. i) supernatant and ii) cell lysates were harvested after 48 hours. Samples were assayed for human IgG.
FIG. 1C depicts the results of an exemplary Western blot performed with cell lysates from transfected cells. 10 μg total cell lysate was loaded in each lane and run on an SDS-PAGE gel, followed by transfer onto a nitrocellulose membrane. The membrane was probed with a goat anti-human IgG H+L antibody, conjugated to HRP. Samples were developed using an ECL chemiluminescence kit and visualized on film.

The ability for each construct to express full length human IgG1 antibody was assessed following in vitro transfection of HEK293T cells. The DMAb-transfected cells and supernatants were harvested after 48 hours and a total IgG ELISA was performed on the cell lysates and in the medium, which verified DMAb IgG production and secretion (FIG. 1B, panels i and ii). A Western blot was also performed to confirm that both antibody heavy and light chains were expressed. The heavy chain for the bispecific DMAb runs at a higher molecular weight as it encodes two variable region specificities (FIG. 1C). pGX0001 DNA vector was included as a negative control and purified anti-PcrV IgG1 as a positive control.

Expression of Anti-*P. aeruginosa* DMAb-αPcrV and DMAb-BiSPA in Mice

Figures 2A, 2B, 2C, 2D:
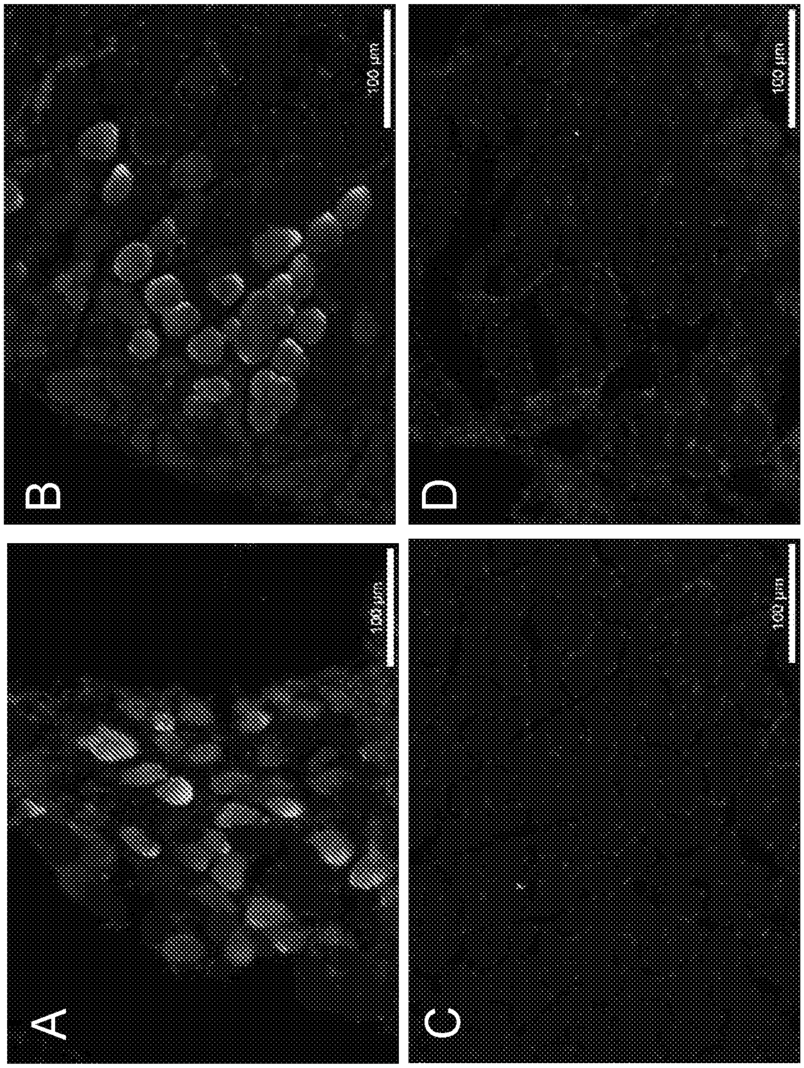
FIG. 2A depicts an exemplary image of cells receiving DMAb-αPcrV.
FIG. 2B depicts an exemplary image of cells receiving DMAb-BiSPA.
FIG. 2C depicts an exemplary image of cells receiving pGX0001 empty vector backbone.
FIG. 2D depicts an exemplary image of naïve muscle cells. Muscle tissue was harvested 3 days post-DMAb injection and probed with a goat anti-humanIgG Fc antibody, followed by detection with anti-goat IgG AF88 and DAPI.
Figures 3A, 3B, 3C, 3D, 3E, 3F:
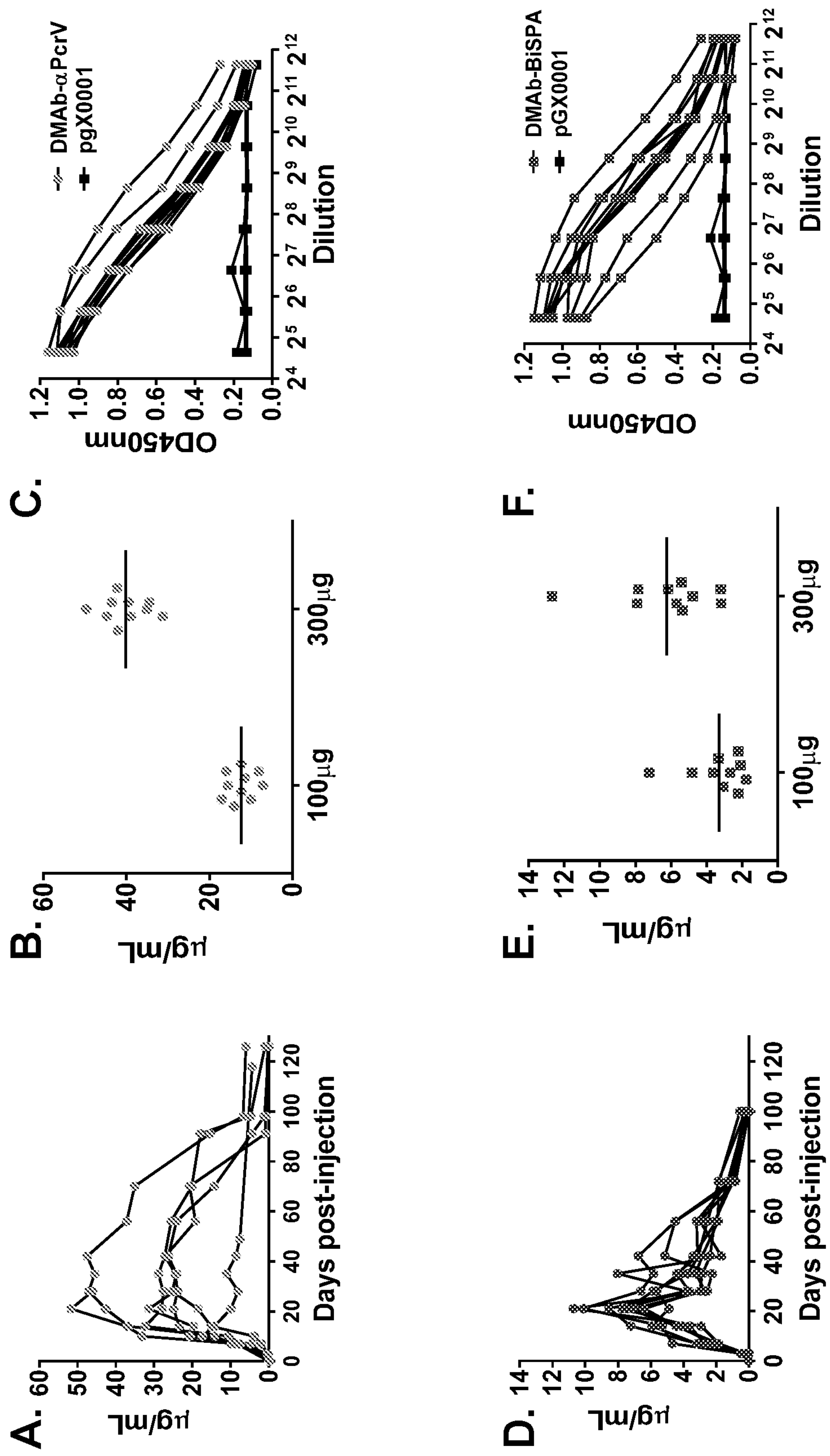
FIG. 3A through FIG. 3F, depicts the results of exemplary experiments demonstrating the in vivo expression of DMAb-αPcrV and DMAb-BiSPA in mice.

Following confirmation of in vitro expression, expression of DNA-delivered DMAb-αPcrV and DMAb-BiSPA in mice was examined. To confirm DMAb expression in mouse muscle, anti-*P. aeruginosa* DMAb-αPcrV (100 μg), DMAb-BiSPA (100 μg), control DMAb-DVSF3 (100 μg), or control pGX0001 empty vector (100 μg), were administered to BALB/c mice by intramuscular injection (IM) in the tibialis anterior (TA), followed by intramuscular electroporation (IM-EP). Muscle tissue was harvested 3 days post-injection and sections were probed with a goat anti-human IgG Fc antibody followed by detection with a donkey anti-goat IgG conjugated to AF488 (FIG. 2). Following confirmation of expression in vivo, further experiments were performed to assay DMAb levels in systemic circulation. Human IgG1 induces an anti-antibody response in immunocompetent mice, since it is recognized as non-self by the murine immune system. Therefore, expression was evaluated in immunocompromised B6.Cg-Foxn1$^{nu}$/J athymic mice (nude) that lack T cells and have non-functional B cells. Anti-*P. aeruginosa* DMAb-αPcrV (100 μg) or DMAb-BiSPA (100 μg) was administered to nude mice (n=5/group) IM in the TA or quadriceps (quad) muscles, followed by IM-EP. Serum was collected to monitor long-term human IgG1 expression in circulation. Expression of both DMAbs was observed for 100-120 days post-administration, supporting the hypothesis that these novel DNA-delivered mAbs can be produced in skeletal muscle in significant amounts detectable in systemic circulation, with expression for several weeks (FIG. 3A and FIG. 3D).

Figures 4A, 4B, 4C:
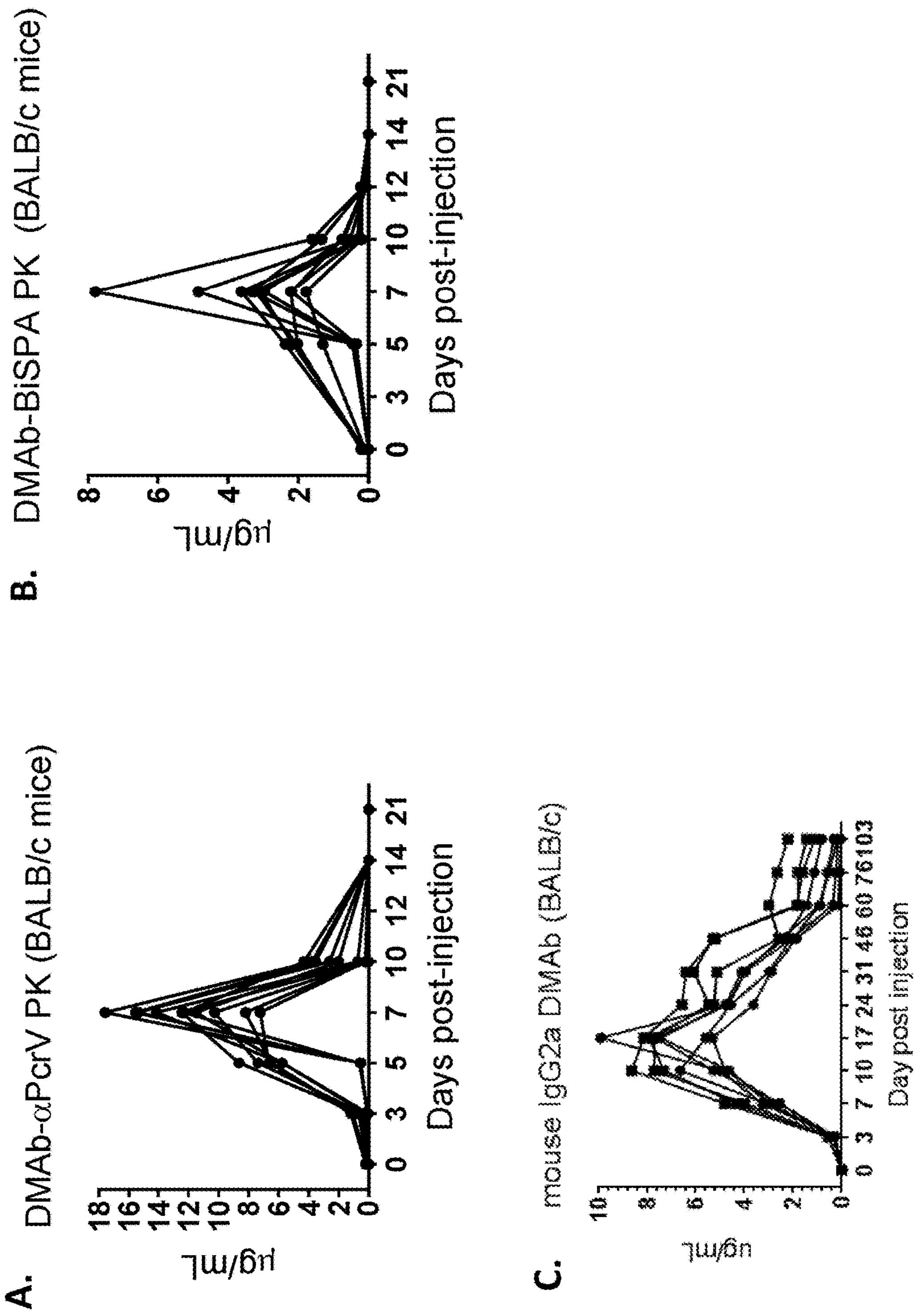
FIG. 4A depicts the results of exemplary experiments demonstrating the pharmacokinetics of DMAb-αPcrV.
FIG. 4B depicts the results of exemplary experiments demonstrating the pharmacokinetics of DMAb-BiSPA.
FIG. 4C depicts the results of exemplary experiments demonstrating the pharmacokinetics of control IgG2A DMAb.

Next, DMAb expression was evaluated in immunocompetent BALB/c mice as they are commonly used as a model for *P. aeruginosa* infection. Mice (n=10/group) were administered 100 μg and 300 μg doses (3 injection sites×100 μg) of DMAb-αPcrV or DMAb-BiSPA by IM-EP. Peak DMAb expression levels were observed at day 7 following injection and were 7.1-17.1 μg/ml and 2.9-7.2 μg/ml at the 100 μg dose and 31.2-49.7 μg/mL and 3.2-12.7 μg/mL at the 300 μg dose for DMAb-αPcrV and DMAb-BiSPA, respectively (FIG. 3B and FIG. 3E). Human IgG1 DMAb expression in BALB/c mice was eliminated by the mouse immune system by Day 14 (FIG. 4A and FIG. 4B). For comparison, a mouse IgG2a DMAb was also designed. This demonstrated long-term expression >100 days in immune competent BALB/c mice, demonstrating long expression of DMAbs without elimination by the immune system (FIG. 4C.) To confirm the target antigen specificity of DMAbs, the day 7 post-administration serum was also assayed and confirmed for binding to recombinant PcrV protein by ELISA (FIG. 3C and FIG. 3F).

Evaluation of DMAb-αPcrV and DMAb-BiSPA in a Lethal Pneumonia Model

Figures 5A, 5B, 5C, 5D:
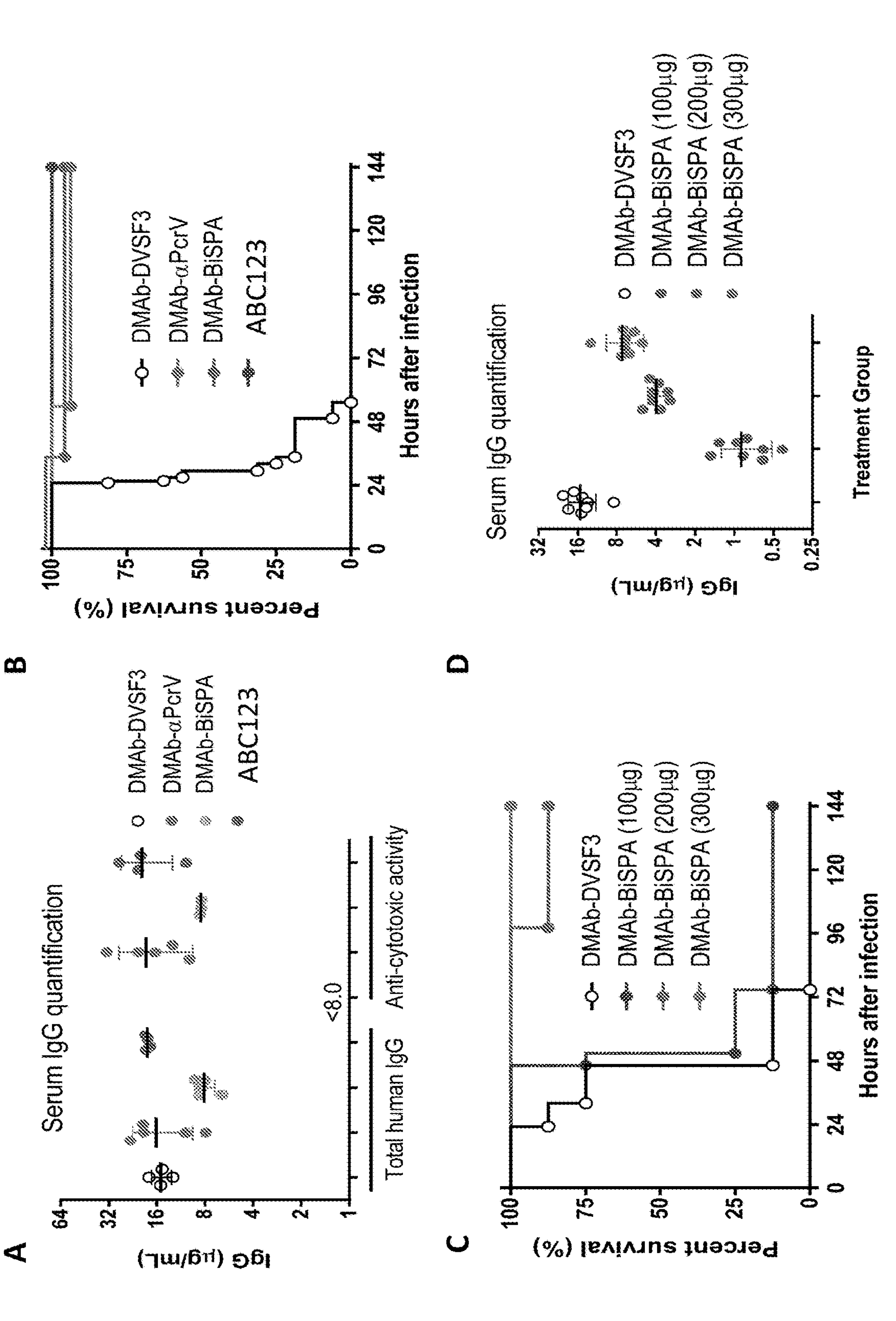
FIG. 5A through FIG. 5D, depicts the results of exemplary experiments demonstrating in vivo functionality and protection conferred by DMAb-αPcrV and DMAb-BiSPA in BALB/c mice following lethal pneumonia challenge.

The in vitro and in vivo expression studies indicated that DMAbs form full, human IgG1 antibodies that bind to recombinant PcrV protein. To address the functional activity of in vivo DNA-delivered DMAbs, protection against the highly pathogenic and cytotoxic *P. aeruginosa* strain, 6077 (PA 6077) was evaluated, using a lethal mouse pneumonia infection model. Mice were injected five days before PA 6077 challenge with DMAb-αPcrV (300 μg), DMAb-BiSPA (300 μg), or an unrelated control DMAb-DVSF3 (300 μg) that targets dengue virus (Flingai et al., 2015, Sci Rep 5, 12616). A positive control group was also included in which mice received protein ABC123 IgG (2 mg/kg) one day before challenge. Randomly selected animals from DMAb-αPcrV and DMAb-BiSPA treated animals were euthanized to monitor DMAb expression levels in serum at the time of challenge as well as to evaluate the potency of the expressed DMAbs. As indicated in FIG. 5A, both monospecific DMAb-αPcrV and bispecific DMAb-BiSPA exhibited median titers of approximately 16 and 8 μg/ml, respectively, when quantifying total human IgG from serum. The potency of in vivo expressed DMAb-αPcrV and DMAb-BiSPA was evaluated by quantifying antibody expression based on the anti-cytotoxic activity from serum. No difference was observed in the quantification methods, indicating that in vivo expressed monospecific and bispecific DMAb-IgGs are fully functional and equivalent in activity in comparison to bioprocessed IgG (FIG. 5A). The remaining animals in each group were then challenged with a lethal dose of *P. aeruginosa* by intranasal inoculation followed by monitoring of survival for 6 days post-infection (144 hours). Animals receiving the control DMAb-DVSF3 succumbed to infection within 24-55 hours. In contrast, approximately 94% of animals (15/16) that received either DMAb-αPcrV or DMAb-BiSPA survived challenge (FIG. 5B, $p<0.0001$ in comparison with DMAb-DVSF3). As expected, positive control animals receiving ABC123 IgG (2 mg/kg) all survived challenge. In addition, treatment of mice with DMAb-BiSPA at 100 μg (1 site×100 μg), 200 μg (2 sites×100 μg), or 300 μg (3 sites×100 μg) followed by infection with *P. aeruginosa*, yielded concentration-dependent survival (FIG. 5C). These results were consistent with the quantification of expressed DMAb-BiSPA in serum from these animals, in which the serum protein concentration of DMAb-BiSPA decreased with decreasing amounts of electroporated DNA (FIG. 5D).

Figures 6A, 6B, 6C, 6D:
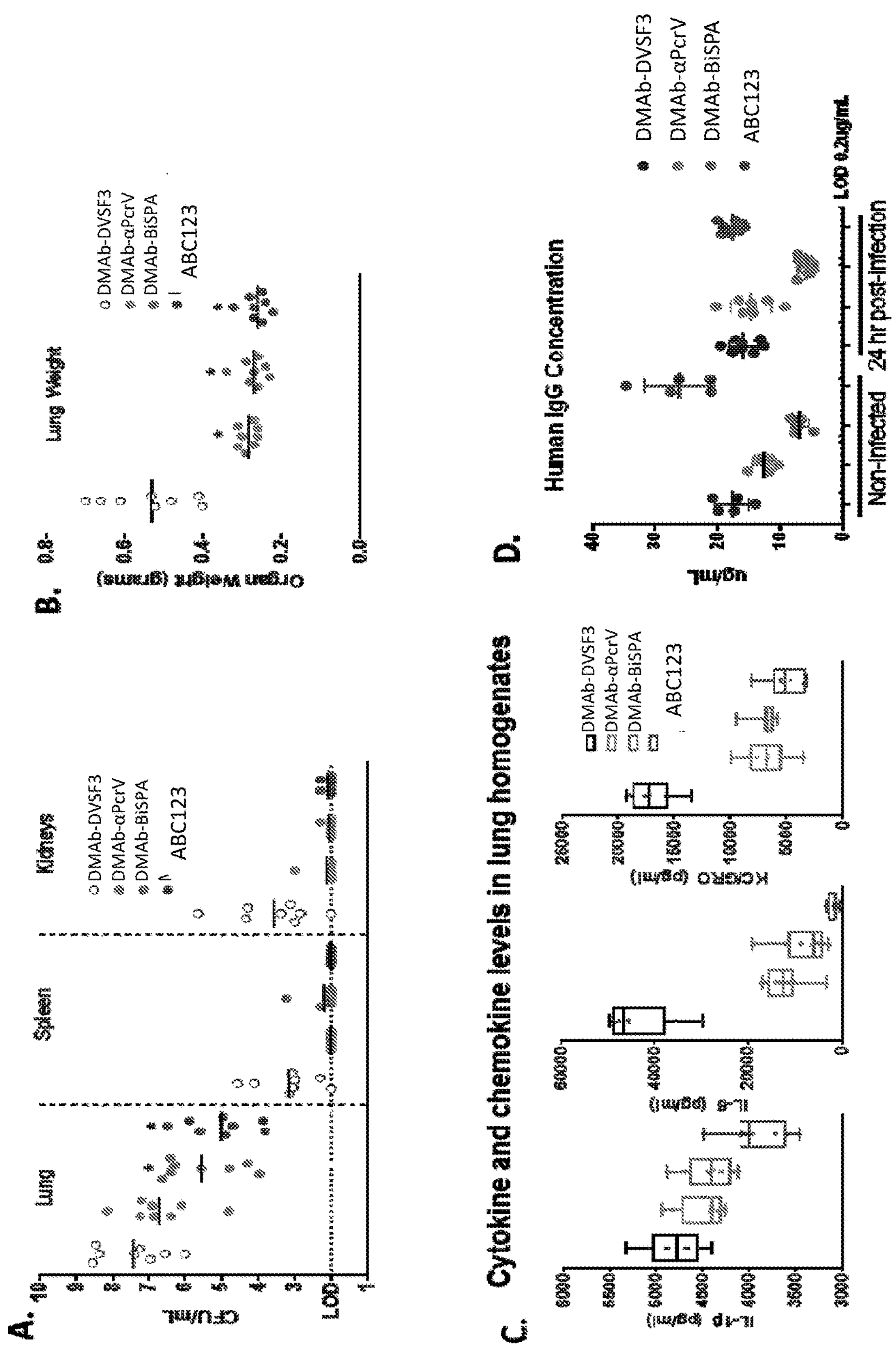
FIG. 6A through FIG. 6D, depicts the results of exemplary experiments demonstrating organ protective effect of DMAb-αPcrV and DMAb-BiSPA treated animals following lethal *P. aeruginosa* challenge.

The ability of anti-*Pseudomonas* DMAbs to reduce the bacterial burden in the lungs and to prevent systemic bacterial dissemination was analyzed. Lungs, spleen, and kidneys were assayed 24 hours post-challenge with *P. aeruginosa* followed by quantification of colony forming units (CFUs) in each tissue. A significant reduction in CFU lung burden was observed with DMAb-BiSPA but not DMAb-αPcrV-treated animals (FIG. 6A). Importantly, bacterial burden in the lungs of DMAb-BiSPA-treated animals were similar to the lung burden observed from mice treated with protein ABC123 IgG and both anti-*Pseudomonas* DMAbs reduced dissemination of bacteria to the spleen and kidneys when compared to the control DMAb-DVSF3 (FIG. 6A). In addition, DMAb-αPcrV, DMAb-BiSPA, and ABC123 IgG were effective in preventing pulmonary edema in infected animals, as measured by lung weight, compared to control DMAb-DVSF3 treated mice (FIG. 6B). Consistent with these results, proinflammatory cytokines IL-1β and IL-6 as well as the chemokine KC/GRO (FIG. 6C) were also reduced in anti-*Pseudomonas* DMAb-treated and protein IgG-treated mice vs. the control DMAb-DVSF3. Serum IgG levels were compared between uninfected animals and infected animals 24 hours post-PA 6077 challenge (FIG. 6D). Taken together, this data suggests that DNA-delivered mAbs produced in vivo in skeletal muscle mediate protective activity and exhibit similar potency to exogenously produced IgG mAbs.

Lung Histopathology Following Challenge

Figures 7A, 7B, 7C, 7D, 7E, 7F, 7G, 7H:
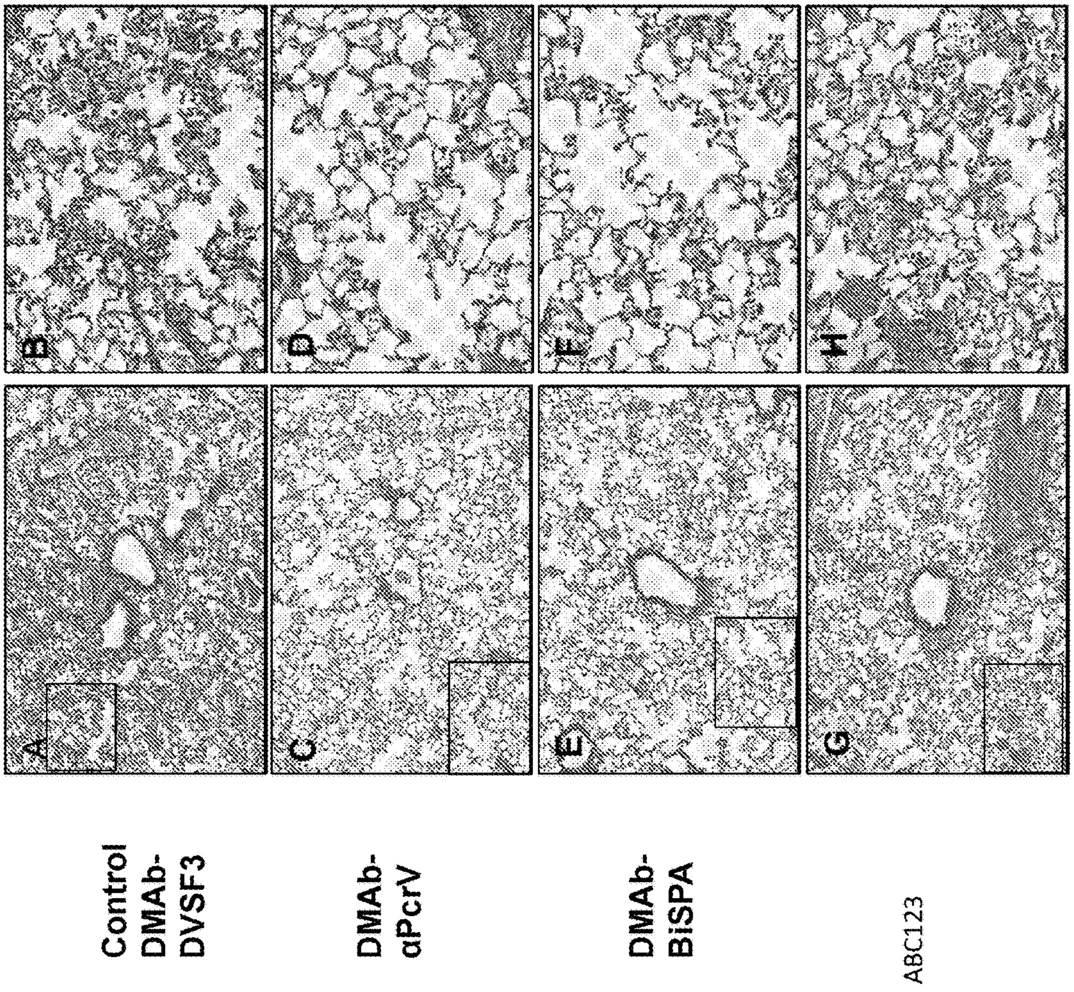
FIG. 7A through FIG. 7H, depicts the results of exemplary experiments demonstrating histology of acute pneumonia at 48 hours post-infection with *P. aeruginosa* 6077 (hematoxylin & eosin (HE)).

Histopathology of lungs harvested at 48 hours post-infection demonstrated a marked alveolitis in DMAb-DVSF3-treated animals with infiltrates of neutrophils and macrophages within alveolar and perivascular spaces, along with areas of hemorrhage and alveolar necrosis. In contrast, and consistent with the reduction in proinflammatory cytokines and chemokines from lung supernatants described above, there was a clear reduction in inflammation with mild populations of primarily neutrophils and fewer macrophages in DMAb-BiSPA treated animals with similar changes seen as well as in the DMAb-αPcrV and control ABC123 IgG groups (FIG. 7).

DMAb Combination with Antibiotics

Figures 8A, 8B:
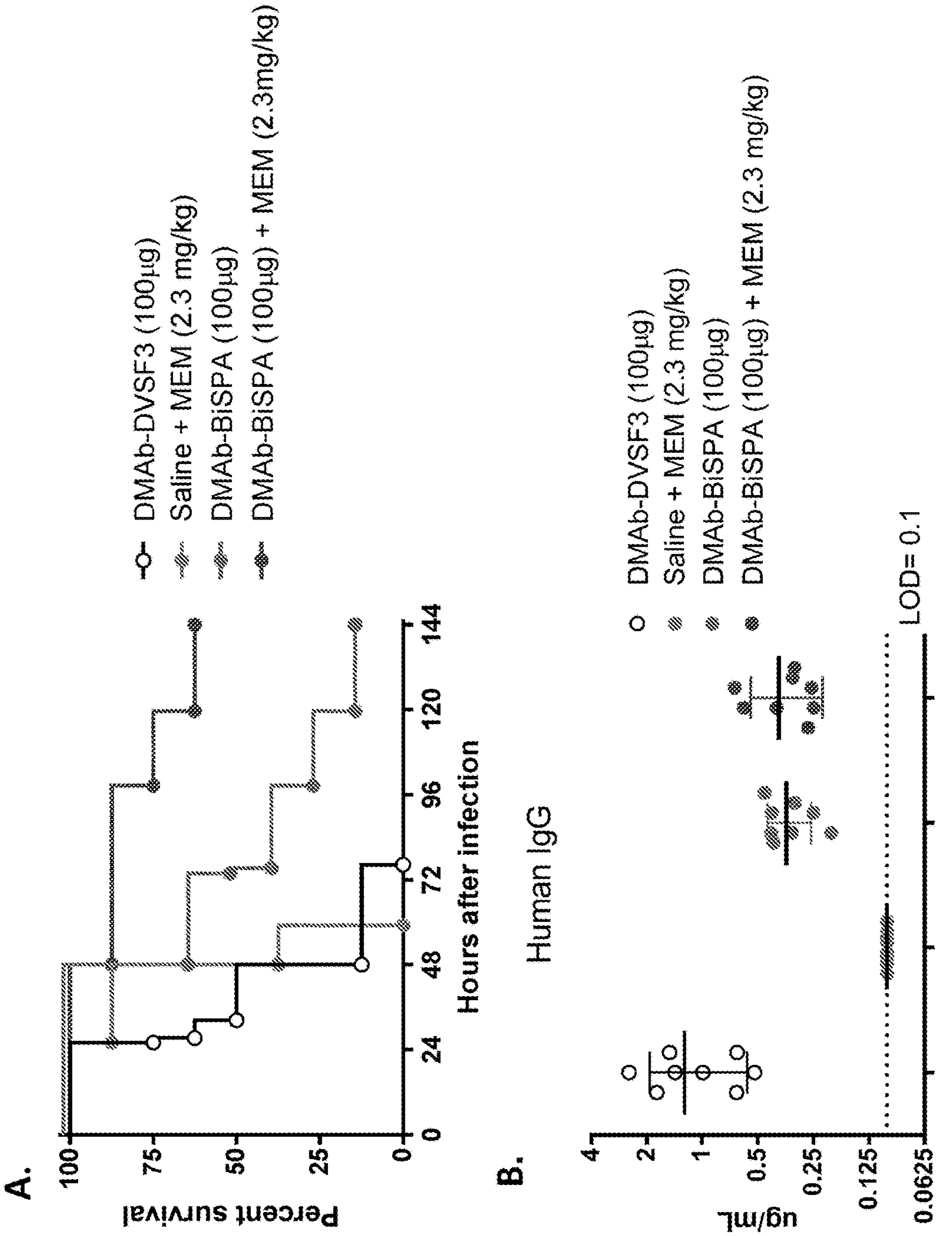
FIG. 8A through FIG. 8B, depicts the results of exemplary experiments demonstrating DMAb combination with antibiotic regimen.

Broad-spectrum carbapenem family antibiotics such as meropenem (MEM) are administered when a Gram negative or *P. aeruginosa* infection is suspected. Further last-resort antibiotic regimens, such as colistin, are associated with high toxicity in humans (Falagas et al., 2005, *BMC Infect Dis* 5, 1; Lim et al., 2010, *Pharmacotherapy* 30, 1279-1291) and there is the potential for the bacterium to acquire further anti-microbial resistance (Hirsch and Tam, 2010, *Expert Rev Pharmacoecon Outcomes Res* 10, 441-451; Lister et al., 2009, *Clin Microbiol Rev* 22, 582-610; Breidenstein et al., 2011, *Trends Microbiol* 19, 419-426). Therefore alternative and adjunctive strategies to reduce these risks would be highly advantageous. The potential application of DMAb-BiSPA treatment was evaluated in combination with MEM. For these experiments, a subtherapeutic dose of MEM (2.3 mg/kg) was used to simulate the inadequate drug exposure encountered in patients infected with a resistant bacterium, and a subtherapeutic dose of DMAb-BiSPA (100 μg, identified in FIG. 5C). Combining these subtherapeutic dosages resulted in 67% survival compared with 10% in animals that received DMAb-BiSPA alone (p=0.026, FIG. 8.) Control mice that received MEM alone or the DMAb-DVSF3 did not survive lethal challenge. Taken together, this expands the application of DMAb treatment as either a standalone treatment or in combination with existing antibiotic regimens. Furthermore, this data supports the hypothesis that DMAb administration functions similarly to purified IgG mAbs and can mediate enhanced protective activity when combined with standard of care antibiotic treatment regimens.

The field of mAb engineering is evolving dynamically and DMAb delivery offers an additional strategy to help transport biologically functional mAbs rapidly in vivo. In addition to obvious clinical benefits, in vivo expression of non-traditional bispecific mAb isoforms, as presented here, emphasizes the versatility of muscle to be engaged as protein production factories. Importantly, DMAb expression is transient, with similar efficacy to other therapeutic deliveries. It may be possible to develop an inducible system that will eliminate the DNA plasmid when it is no longer needed. Alternatively, DMAb DNA can potentially be re-administered indefinitely as there are no associated anti-vector responses, allowing for long term therapy through repeat administration (Hirao et al., 2010, *Molecular therapy: the journal of the American Society of Gene Therapy* 18, 1568-1576; Williams, 2013, *Vaccines* 1, 225-249; Schmaljohn et al., 2014, *Virus research* 187, 91-96). DMAb delivery represents a significant advancement not only for mAb therapy and DNA-delivery technology, but also for novel pathogen-specific treatment approaches to enhance host immunity.

Figure 9:
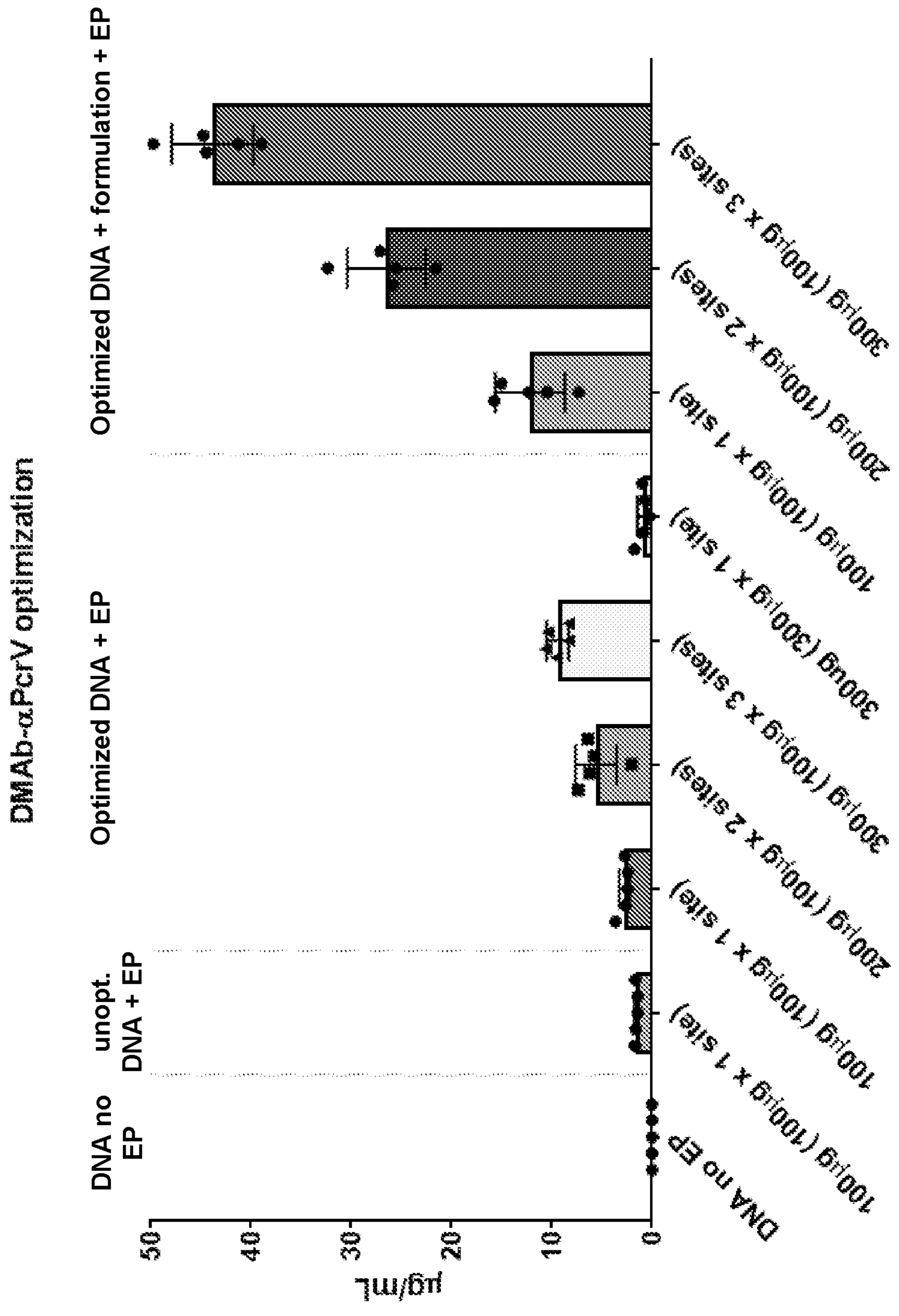
FIG. 9 depicts the results of exemplary experiments demonstrating optimization of DMAb-V2L2 in vivo expression. BALB/c mice received a single DNA injection into the TA muscle with DMAb-αPcrV or DMAb-BiSpA DNA followed by in vivo electroporation. Graph represents Day 7 serum levels in BALB/c mice (n=5/group) administered 100 μg, 200 μg, or 300 μg for DMAb-αPcrV, respectively, before and after sequence, formulation with hyaluronidase (400U/mL), and electroporation optimizations.

Recently delivery of DNA-encoded antibodies that target Her2 in a mouse model of human breast cancer carcinoma has been reported (Kim et al., 2016, *Cancer Gene Ther* 23, 341-347). This study demonstrated anti-tumor efficacy comparable to protein IgG, further supporting the concept that a gene-encoded mAb can have functionality. This is the first demonstration of DNA-encoded mAb (DMAb) delivery that is protective against a bacterial target and the first delivery of an engineered IgG isoform. Early studies with DNA plasmid-encoded antibodies demonstrated feasibility but exhibited low IgG expression in serum (Tjelle et al., 2004, *Molecular therapy: the journal of the American Society of Gene Therapy* 9, 328-336; Perez et al., 2004, *Genet Vaccines Ther* 2, 2). The protective efficacy of DMAbs targeting viral infections has previously been studies, showing rapid protection against chikungunya (Muthumani et al., 2016, *J Infect Dis* 214, 369-378) and dengue virus (DENV) infections (Flingai et al., 2005, *Sci Rep* 5, 12616). The DMAb targeting DENV also did not promote antibody-dependent enhancement of disease. These two infectious disease models did not require high serum IgG levels, however optimized DMAb formulations to increase expression levels are desirable so as to provide extended coverage after a single DMAb administration. Towards this end, serum DMAb expression levels were optimized for use against *Pseudomonas aeruginosa* (FIG. 9). This work included the inclusion of hyaluronidase into the formulation regimen, which allowed for greater IgG expression from the treated muscle.

Although further study is required for translation to humans, DMAbs are a step towards enabling routine delivery of mAb, with the potential for increasing accessibility to diverse communities worldwide. Dose translation in larger animals and humans will be important to address in future studies, particularly understanding DNA dose-limitations during DMAb administration. This includes investigating different delivery and formulation optimizations that will enhance DNA expression in vivo. One strategy may be to employ other extracellular matrix enzymes to facilitate DNA entry into muscle cells[37]. Further study in non-human primates may help to understand the threshold for DNA dosage and impact on pharmacokinetic levels. Additional studies evaluating the glycosylation patterns of human IgG DMAbs produced in muscle would be beneficial to compare with bioprocessed protein IgG, however in the context of the current study there was no difference in functionality between DMAb and its protein IgG counterpart.

In conclusion, the work described herein could be of tremendous significance for the treatment of AMR infections, particularly against ESKAPE pathogens that are refractory to many broad-spectrum antibiotic regimens. DMAbs are versatile and can deliver monospecific IgGs against multiple antigenic targets as well as encode novel bispecific IgGs. The sustained serum mAb trough levels produced by a single dose of DMAb are consistent with functionality and protective levels afforded by bioprocessed protein IgG in vivo. The rapid development of this platform and prolonged transient expression from muscle are favourable in comparison with protein IgG mAb regimens as it could enable less frequent mAb administration. Furthermore, DMAbs are temperature stable allowing for transport, long-term storage, and administration to broader populations. These attractive features combined with the safety profile of DNA delivery in humans, support further DMAb studies in larger animal models as a pathogen-specific approach to targeting infectious diseases and other potential therapeutic targets.

TABLE 1

Sequence Descriptions

| SEQ ID NO: | Description |
|---|---|
| 1 | nucleotide sequence of pGX9308: V2L2MD heavy chain |
| 2 | amino acid sequence of pGX9308: V2L2MD heavy chain |
| 3 | nucleotide sequence of pGX9309: V2L2MD light chain |
| 4 | amino acid sequence of pGX9309: V2L2MD light chain |
| 5 | nucleotide sequence of pGX9214: Pseudo-V2L2MD; DMAb-αPcrV |
| 6 | amino acid sequence of pGX9214: Pseudo-V2L2MD; DMAb-αPcrV |
| 7 | nucleotide sequence of pGX9247: V2L2 with Rhesus Fc in pGX0001; DMAb-αPcrV |
| 8 | amino acid sequence of pGX9247: V2L2 with Rhesus Fc in pGX0001; DMAb-αPcrV |
| 9 | nucleotide sequence of pGX9248: Pseudo-V2L2MD rbFc; DMAb-αPcrV |
| 10 | amino acid sequence of pGX9248: Pseudo-V2L2MD rbFc; DMAb-αPcrV |
| 11 | nucleotide sequence of pGX9257 heavy chain: Pseudo-V2L2MD in pGX0003 (sCMV-light chain, hCMV-heavy chain); DMAb-αPcrV |
| 12 | amino acid sequence of pGX9257 heavy chain: Pseudo-V2L2MD in pGX0003 (sCMV-light chain, hCMV-heavy chain); DMAb-αPcrV |
| 13 | nucleotide sequence of pGX9258: Psuedo-V2L2MD-YTE only in pGX0001; DMAb-αPcrV |
| 14 | amino acid sequence of pGX9258: Psuedo-V2L2MD-YTE only in pGX0001; DMAb-αPcrV |
| 15 | nucleotide sequence of pGX9257 light chain: Pseudo-V2L2MD in pGX0003 (sCMV-light chain, hCMV-heavy chain); DMAb-αPcrV |
| 16 | amino acid sequence of pGX9257 light chain: Pseudo-V2L2MD in pGX0003 (sCMV-light chain, hCMV-heavy chain); DMAb-αPcrV |
| 17 | nucleotide sequence of pGX9213: Bispecific *Pseudomonas* (Bis4-V2L2MD/PsI0096); DMAb-BiSPA |
| 18 | amino acid sequence of pGX9213: Bispecific *Pseudomonas* (Bis4-V2L2MD/PsI0096); DMAb-BiSPA |
| 19 | nucleotide sequence of pGX9215: Pseudo-Ps10096; DMAb-αPsI |
| 20 | amino acid sequence of pGX9215: Pseudo-Ps10096; DMAb-αPsI |
| 21 | nucleotide sequence of pGX9259: Bispecific *Pseudomonas* (Bis4-V2L2MD/PsI0096)-YTE only pGX0001; DMAb-BiSPA |
| 22 | amino acid sequence of pGX9259: Bispecific *Pseudomonas* (Bis4-V2L2MD/PsI0096)-YTE only pGX0001; DMAb-BiSPA |
| 23 | furin cleavage sequence |
| 24 | amino acid sequence of a heavy chain leader sequence |
| 25 | amino acid sequence of a light chain leader sequence |
| 26 | nucleotide sequence of pGX9308: V2L2MD heavy chain operably linked to a sequence encoding an IgE leader sequence |
| 27 | amino acid sequence of pGX9308: V2L2MD heavy chain operably linked to an IgE leader sequence |
| 28 | nucleotide sequence of pGX9309: V2L2MD light chain operably linked to a sequence encoding an IgE leader sequence |
| 29 | amino acid sequence of pGX9309: V2L2MD light chain operably linked to an IgE leader sequence |
| 30 | nucleotide sequence of pGX9214: Pseudo-V2L2MD; DMAb-αPcrV operably linked to a sequence encoding an IgE leader sequence |
| 31 | amino acid sequence of pGX9214: Pseudo-V2L2MD; DMAb-αPcrV operably linked to an IgE leader sequence |
| 32 | nucleotide sequence of pGX9247: V2L2 with Rhesus Fc in pGX0001; DMAb-αPcrV operably linked to a sequence encoding an IgE leader sequence |
| 33 | amino acid sequence of pGX9247: V2L2 with Rhesus Fc in pGX0001; DMAb-αPcrV operably linked to an IgE leader sequence |
| 34 | nucleotide sequence of pGX9248: Pseudo-V2L2MD rbFc; DMAb-αPcrV operably linked to a sequence encoding an IgE leader sequence |
| 35 | amino acid sequence of pGX9248: Pseudo-V2L2MD rbFc; DMAb-αPcrV operably linked to an IgE leader sequence |
| 36 | nucleotide sequence of pGX9257 heavy chain: Pseudo-V2L2MD in pGX0003 (sCMV-light chain, hCMV-heavy chain); DMAb-αPcrV operably linked to a sequence encoding an IgE leader sequence |

TABLE 1-continued

| Sequence Descriptions | |
|---|---|
| SEQ ID NO: | Description |
| 37 | amino acid sequence of pGX9257 heavy chain: Pseudo-V2L2MD in pGX0003 (sCMV-light chain, hCMV-heavy chain); DMAb-αPcrV operably linked to an IgE leader sequence |
| 38 | nucleotide sequence of pGX9258: Psuedo-V2L2MD-YTE only in pGX0001; DMAb-αPcrV operably linked to a sequence encoding an IgE leader sequence |
| 39 | amino acid sequence of pGX9258: Psuedo-V2L2MD-YTE only in pGX0001; DMAb-αPcrV operably linked to an IgE leader sequence |
| 40 | nucleotide sequence of pGX9257 light chain: Pseudo-V2L2MD in pGX0003 (sCMV-light chain, hCMV-heavy chain); DMAb-αPcrV operably linked to a sequence encoding an IgE leader sequence |
| 41 | amino acid sequence of pGX9257 light chain: Pseudo-V2L2MD in pGX0003 (sCMV-light chain, hCMV-heavy chain); DMAb-αPcrV operably linked to an IgE leader sequence |
| 42 | nucleotide sequence of pGX9213: Bispecific *Pseudomonas* (Bis4-V2L2MD/PsI0096); DMAb-BiSPA operably linked to a sequence encoding an IgE leader sequence |
| 43 | amino acid sequence of pGX9213: Bispecific *Pseudomonas* (Bis4-V2L2MD/PsI0096); DMAb-BiSPA operably linked to an IgE leader sequence |
| 44 | nucleotide sequence of pGX9215: Pseudo-Ps10096; DMAb-αPsI operably linked to a sequence encoding an IgE leader sequence |
| 45 | amino acid sequence of pGX9215: Pseudo-Ps10096; DMAb-αPsI operably linked to an IgE leader sequence |
| 46 | nucleotide sequence of pGX9259: Bispecific *Pseudomonas* (Bis4-V2L2MD/PsI0096)-YTE only pGX0001; DMAb-BiSPA operably linked to a sequence encoding an IgE leader sequence |
| 47 | amino acid sequence of pGX9259: Bispecific *Pseudomonas* (Bis4-V2L2MD/PsI0096)-YTE only pGX0001; DMAb-BiSPA operably linked to an IgE leader sequence |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding one or more DNA monoclonal antibody (DMAb), wherein the nucleic acid molecule comprises a nucleotide sequence encoding one or more of a variable heavy chain region and a variable light chain region of an anti-PcrV DMAb (DMAb-αPcrV) selected from the group consisting of: a nucleotide sequence encoding an amino acid sequence of SEQ ID NO:6 and a nucleotide sequence of SEQ ID NO:5.

2. The nucleic acid molecule of claim 1, further comprising a nucleotide sequence encoding a cleavage domain.

3. The nucleic acid molecule of claim 1, further comprising a nucleotide sequence encoding a signal peptide.

4. The nucleic acid molecule of claim 1, wherein the nucleic acid molecule further comprises a nucleotide sequence encoding an internal ribosome entry site (IRES) element.

5. The nucleic acid molecule of claim 1, wherein the nucleic acid molecule further comprises a nucleotide sequence encoding a signal peptide selected from the group consisting of SEQ ID NO:24 and SEQ ID NO:25.

6. The nucleic acid molecule of claim 1, wherein the nucleic acid molecule is a ribonucleic acid molecule.

7. An expression vector comprising the nucleic acid molecule of claim 1.

8. A composition comprising the nucleic acid molecule of claim 1.

9. The composition of claim 8, further comprising a pharmaceutically acceptable excipient.

10. A method of treating a *Pseudomonas aeruginosa* infection in a subject, the method comprising administering to the subject the nucleic acid molecule of claim 1.

11. The method of claim 10, further comprising administering an antibiotic agent to the subject.

12. The method of claim 11, wherein an antibiotic is administered less than 10 days after administration of the nucleic acid molecule or composition.

13. A method of treating a *Pseudomonas aeruginosa* biofilm formation in a subject, the method comprising administering to the subject the nucleic acid molecule of claim 1.

14. The method of claim 13, further comprising administering an antibiotic agent to the subject.

15. The method of claim 14, wherein an antibiotic is administered less than 10 days after administration of the nucleic acid molecule or composition.

* * * * *

SEQUENCE LISTING

```
<160> NUMBER OF SEQ ID NOS: 47

<210> SEQ ID NO 1
<211> LENGTH: 1362
<212> TYPE: DNA
<213> ORGANISM: Artificial Sequence
<220> FEATURE:
<223> OTHER INFORMATION: nucleotide sequence of pGX9308: V2L2MD heavy
      chain

<400> SEQUENCE: 1

gaggtgcagc tgctggagag cggcggcggc ctggtgcagc ctggcggcag cctgaggctg      60

tcctgcgcag catctggctt cacctttagc tcctatgcaa tgaactgggt gcgccaggca     120

ccaggcaagg gactggagtg ggtgtctgcc atcacaatga gcggcatcac cgcctactat     180

acagacgatg tgaagggcag gtttaccatc agcagagaca actccaagaa tacactgtac     240

ctgcagatga atagcctgag agccgaggat accgccgtgt actattgcgc caaggaggag     300

ttcctgcccg gcacacacta ctattacgga atggacgtgt ggggacaggg aaccacagtg     360

accgtgtcta gcgcctccac aaagggacct agcgtgttcc cactggcacc ctcctctaag     420
```

```
tccacctctg gcggcacagc cgccctgggc tgtctggtga aggattattt cccagagccc    480

gtgaccgtgt cttggaacag cggcgccctg acctctggag tgcacacatt tccagccgtg    540

ctgcagagct ccggcctgta tagcctgtct agcgtggtga ccgtgccctc ctctagcctg    600

ggcacccaga catacatctg caacgtgaat cacaagccat ctaatacaaa ggtggacaag    660

aaggtggagc ccaagagctg tgataagacc cacacatgcc ctccctgtcc tgcaccagag    720

ctgctgggcg gcccatccgt gttcctgttt ccacccaagc ctaaggacac cctgatgatc    780

tcccggaccc cagaggtgac atgcgtggtg gtggacgtgt ctcacgagga ccccgaggtg    840

aagttcaact ggtacgtgga tggcgtggag gtgcacaatg ccaagaccaa gccacgggag    900

gagcagtata acagcaccta ccgcgtggtg tccgtgctga cagtgctgca ccaggactgg    960

ctgaacggca aggagtacaa gtgcaaggtg agcaataagg ccctgcccgc ccctatcgag   1020

aagaccatct ccaaggccaa gggccagcct agggagccac aggtgtatac actgcctcca   1080

agcagagacg agctgaccaa gaaccaggtg tccctgacat gtctggtgaa gggcttctac   1140

ccttccgata tcgccgtgga gtgggagtct aatggccagc cagagaacaa ttataagacc   1200

acaccccctg tgctggactc cgatggctct ttctttctgt actctaagct gaccgtggat   1260

aagagccgct ggcagcaggg caacgtgttt agctgttccg tgatgcacga ggccctgcac   1320

aatcactaca cacagaagtc tctgagcctg tcccctggca ag                      1362
```

<210> SEQ ID NO 2
<211> LENGTH: 454
<212> TYPE: PRT
<213> ORGANISM: Artificial Sequence
<220> FEATURE:
<223> OTHER INFORMATION: amino acid sequence of pGX9308: V2L2MD heavy chain

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 3
<211> LENGTH: 642
<212> TYPE: DNA
<213> ORGANISM: Artificial Sequence
<220> FEATURE:
<223> OTHER INFORMATION: nucleotide sequence of pGX9309: V2L2MD light chain

<400> SEQUENCE: 3

```
gcaatccaga tgacccagtc cccaagctcc ctgagcgcct ccgtgggcga cagggtgacc      60

atcacatgca gagcctctca gggcatccgg aacgatctgg gctggtacca gcagaagcca     120

ggcaaggccc ccaagctgct gatctattct gccagcaccc tgcagtctgg agtgcccagc     180

cggttctccg gctctggcag cggaacagac tttaccctga caatctctag cctgcagcct     240

gaggacttcg ccacctacta ttgcctgcag gattacaatt atccatggac ctttggccag     300

ggcacaaagg tggagatcaa gcgcacagtg gccgccccca gcgtgttcat ctttcccccct     360

agcgacgagc agctgaagtc cggcaccgcc tctgtggtgt gcctgctgaa caatttctac     420

cctagggagg ccaaggtgca gtggaaggtg gataacgccc tgcagagcgg caattcccag     480
```

```
gagtctgtga ccgagcagga cagcaaggat tccacatatt ccctgtctaa caccctgaca    540

ctgagcaagg ccgattacga gaagcacaag gtgtatgcat gcgaggtgac ccaccaggga    600

ctgtcctctc ccgtgacaaa gtcctttaat aggggcgagt gt                       642
```

<210> SEQ ID NO 4
<211> LENGTH: 214
<212> TYPE: PRT
<213> ORGANISM: Artificial Sequence
<220> FEATURE:
<223> OTHER INFORMATION: amino acid sequence of pGX9309: V2L2MD light chain

<400> SEQUENCE: 4

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 2151
<212> TYPE: DNA
<213> ORGANISM: Artificial Sequence
<220> FEATURE:
<223> OTHER INFORMATION: nucleotide sequence of pGX9214: Pseudo-V2L2MD; DMAb-antiPcrV

<400> SEQUENCE: 5

```
gaggtgcagc tgctggagtc aggaggagga ctggtgcagc ccggcggatc actgcgactg     60

agctgcgcag cttccggctt caccttcagc agctatgcca tgaactgggt ccgacaggct    120

cctggcaagg gactggaatg ggtgagtgca atcaccatgt cagggattac tgcctactat    180

accgacgatg tgaaaggccg attcactatc tctagggaca acagtaagaa taccctgtac    240

ctgcagatga attccctgcg cgctgaggat acagcagtgt actattgcgc caaggaggaa    300
```

-continued

```
ttcctgccag ggactcacta ctattacgga atggacgtgt ggggacaggg aaccacagtc    360

accgtgtcta gtgcaagcac aaaaggcccc tccgtgtttc ccctggcccc ttcaagcaag    420

tctacaagtg ggggcactgc agccctggga tgtctggtga aggattactt ccctgagcca    480

gtcaccgtga gctggaactc cggcgccctg acttccggag tccatacctt tcctgctgtg    540

ctgcagtcct ctggcctgta tagcctgagt tcagtggtca ccgtcccaag ctcctctctg    600

ggaacacaga cttacatctg caacgtgaat cacaaaccaa gcaatacaaa ggtcgacaag    660

aaagtggaac ccaaatcctg tgataagacc catacatgcc ctccctgtcc agcacctgag    720

ctgctgggag ggccaagcgt gttcctgttt ccacccaagc ctaaagacac actgatgatt    780

tctcggaccc ccgaagtcac atgcgtggtc gtggacgtga gccacgagga ccccgaagtc    840

aagtttaact ggtacgtgga tggcgtcgag gtgcataatg ccaagaccaa accacgagag    900

gaacagtata actctacata cagggtcgtg agtgtcctga ctgtgctgca ccaggactgg    960

ctgaacggga aggagtacaa gtgcaaagtg tccaacaagg ccctgccagc tcccatcgag   1020

aagaccattt ctaaggccaa aggccagcca agagaacccc aggtgtatac actgcctcca   1080

agtcgggacg agctgactaa aaaccaggtc tctctgacct gtctggtgaa gggattctac   1140

ccttccgata tcgctgtgga gtgggaatct aatgggcagc cagaaaacaa ttataagact   1200

acccctcccg tgctggactc tgatggaagt ttctttctgt actccaaact gaccgtggac   1260

aagtctagat ggcagcaggg gaacgtcttt tcatgcagcg tgatgcatga ggccctgcac   1320

aatcattaca ctcagaaatc cctgtctctg agtcctggga aacggggccg caagaggaga   1380

tcaggaagcg gggccaccaa cttctccctg ctgaagcagg ctggcgatgt ggaggaaaat   1440

cctggaccaa tggtcctgca gactcaggtg tttatctcac tgctgctgtg gattagcgga   1500

gcatacgggg ccattcagat gacccagtcc cccagttcac tgtccgcttc tgtcggcgac   1560

agagtgacta tcacctgtcg ggcaagccag ggaattcgca acgatctggg gtggtatcag   1620

cagaagcctg ggaaagctcc aaagctgctg atctacagtg catcaactct gcagtcagga   1680

gtgcctagcc ggttcagcgg ctccggatct ggaaccgact ttacactgac tattagctcc   1740

ctgcagccag aggacttcgc cacatattac tgcctgcagg attataatta cccctggaca   1800

tttggccagg gaactaaagt ggaaatcaag cgcacagtcg ctgcacctag cgtgttcatc   1860

tttccaccct cagacgagca gctgaagtcc ggaactgctt ctgtggtgtg cctgctgaac   1920

aatttctatc caagggaagc aaaagtccag tggaaggtgg ataacgccct gcagtcaggc   1980

aatagccagg agtccgtgac cgaacaggac tctaaagata gtacatacag tctgtcaaac   2040

accctgacac tgagcaaggc tgattatgag aagcacaaag tgtacgcatg cgaagtcacc   2100

caccaggggc tgtcctcacc agtcacaaaa tctttcaatc ggggagaatg c            2151
```

```
<210> SEQ ID NO 6
<211> LENGTH: 717
<212> TYPE: PRT
<213> ORGANISM: Artificial Sequence
<220> FEATURE:
<223> OTHER INFORMATION: amino acid sequence of pGX9214: Pseudo-V2L2MD;
      DMAb-antiPcrV

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445
```

```
Ser Leu Ser Pro Gly Lys Arg Gly Arg Lys Arg Arg Ser Gly Ser Gly
    450                 455                 460

Ala Thr Asn Phe Ser Leu Leu Lys Gln Ala Gly Asp Val Glu Glu Asn
465                 470                 475                 480

Pro Gly Pro Met Val Leu Gln Thr Gln Val Phe Ile Ser Leu Leu Leu
                485                 490                 495

Trp Ile Ser Gly Ala Tyr Gly Ala Ile Gln Met Thr Gln Ser Pro Ser
            500                 505                 510

Ser Leu Ser Ala Ser Val Gly Asp Arg Val Thr Ile Thr Cys Arg Ala
        515                 520                 525

Ser Gln Gly Ile Arg Asn Asp Leu Gly Trp Tyr Gln Gln Lys Pro Gly
    530                 535                 540

Lys Ala Pro Lys Leu Leu Ile Tyr Ser Ala Ser Thr Leu Gln Ser Gly
545                 550                 555                 560

Val Pro Ser Arg Phe Ser Gly Ser Gly Ser Gly Thr Asp Phe Thr Leu
                565                 570                 575

Thr Ile Ser Ser Leu Gln Pro Glu Asp Phe Ala Thr Tyr Tyr Cys Leu
            580                 585                 590

Gln Asp Tyr Asn Tyr Pro Trp Thr Phe Gly Gln Gly Thr Lys Val Glu
        595                 600                 605

Ile Lys Arg Thr Val Ala Ala Pro Ser Val Phe Ile Phe Pro Pro Ser
    610                 615                 620

Asp Glu Gln Leu Lys Ser Gly Thr Ala Ser Val Val Cys Leu Leu Asn
625                 630                 635                 640

Asn Phe Tyr Pro Arg Glu Ala Lys Val Gln Trp Lys Val Asp Asn Ala
                645                 650                 655

Leu Gln Ser Gly Asn Ser Gln Glu Ser Val Thr Glu Gln Asp Ser Lys
            660                 665                 670

Asp Ser Thr Tyr Ser Leu Ser Asn Thr Leu Thr Leu Ser Lys Ala Asp
        675                 680                 685

Tyr Glu Lys His Lys Val Tyr Ala Cys Glu Val Thr His Gln Gly Leu
    690                 695                 700

Ser Ser Pro Val Thr Lys Ser Phe Asn Arg Gly Glu Cys
705                 710                 715


<210> SEQ ID NO 7
<211> LENGTH: 2154
<212> TYPE: DNA
<213> ORGANISM: Artificial Sequence
<220> FEATURE:
<223> OTHER INFORMATION: nucleotide sequence of pGX9247: V2L2 with
      Rhesus Fc in pGX0001; DMAb-antiPcrV

<400> SEQUENCE: 7

gaggtgcagc tcctggaaag tgggggaggg ctggtgcagc ccggcgggtc cctcagactg      60

tcttgcgccg ctagtggctt cacctttagc tcctatgcaa tgaactgggt gcggcaggca     120

cctgggaaag gactggagtg ggtgagcgcc atcaccatgt ccggcattac tgcatactat     180

accgacgatg tgaaagggag gttcacaatc tcaagagaca acagcaagaa tactctctac     240

ctgcagatga atagcctgcg cgctgaggat actgcagtgt actattgcgc caaggaggaa     300

ttcctgccag gcacccacta ctattacgga atggacgtgt ggggacaggg aaccacagtc     360

accgtgtcta gtgcttctac aaaagggccc agcgtgttcc cactggcacc ctcaagcagg     420

agtacatcag agagcactgc agccctcgga tgtctggtga aggattactt ccccgaacct     480

gtcaccgtgt cctggaactc cggatctctc acttctggcg tccacacctt tcccgccgtg     540
```

```
ctgcagtcct ctgggctcta tagcctgagt tcagtggtca ccgtgcctag ctcctctctg    600

ggaacacaga cttacgtctg caacgtgaat cataagccat ccaatacaaa ggtcgacaaa    660

agagtggaga tcaaaacctg tggaggcggg tctaagcccc ctacatgccc accctgtcca    720

gcaccagaac tgctcggagg cccaagcgtg ttcctctttc ctccaaagcc caaagacacc    780

ctgatgattt cccggacccc agaggtcaca tgcgtggtcg tggacgtgag ccaggaagac    840

cctgatgtca aattcaactg gtacgtgaat ggcgccgagg tgcaccatgc tcagacaaag    900

cccagagaaa ctcagtataa ctcaacctac cgggtcgtga gcgtcctcac cgtgacacac    960

caggactggc tgaacggcaa agagtataca tgcaaagtga gcaataaggc cctgcctgct   1020

ccaatccaga agactattag caaggataaa gggcagcctc gcgaaccaca ggtgtacacc   1080

ctgcctccca gcagggagga actgactaaa aaccaggtca gcctcacctg tctggtgaag   1140

ggcttctacc cttccgacat cgtcgtggag tgggaaagtt caggccagcc agagaatacc   1200

tacaagacta ccccacccgt gctggactct gatggaagtt atttcctcta cagcaaactg   1260

acagtggata agtccagatg gcagcagggc aacgtcttta gttgctcagt gatgcatgag   1320

gccctccaca atcattacac acagaaaagc ctgtccgtgt ctccccgggg caggaagagg   1380

agaagtggat caggcgcaac taacttcagc ctgctcaagc aggcagggga cgtggaggaa   1440

aatcccggac ctatggtcct gcagacccag gtgtttatct ccctgctcct gtggatttct   1500

ggcgcatacg gggccatcca gatgacacag agccccagct ccctgagcgc ctccgtcggc   1560

gaccgggtga ctatcacctg tcgcgctagc cagggaatta ggaacgatct gggctggtat   1620

cagcagaagc ccggcaaagc ccctaagctc ctgatctact ctgctagtac actgcagtcc   1680

ggggtgcctt ctaggttctc agggagcggc agcggcactg acttcaccct cactatttct   1740

agtctgcagc cagaggactt cgcaacctat tactgcctgc aggattataa ttacccctgg   1800

acatttgggc agggaactaa agtggagatc aagcgcgctg tcgctgcacc tagcgtgttc   1860

atctttcctc caagtgaaga ccaggtcaag agtggcaccg tgtcagtggt gtgcctcctg   1920

aacaatttct atccaaggga ggcctccgtg aagtggaaag tcgatggggt gctgaaaaca   1980

ggaaactcac aggagagcgt gactgaacag gacagtaagg ataataccta ctcactgtca   2040

agcaccctca cactgtcctc taccgactat cagtctcaca acgtgtacgc ttgcgaagtc   2100

acccaccagg ggctcagtag tccagtcaca aaatctttca atagaggcga atgt         2154
```

```
<210> SEQ ID NO 8
<211> LENGTH: 718
<212> TYPE: PRT
<213> ORGANISM: Artificial Sequence
<220> FEATURE:
<223> OTHER INFORMATION: amino acid sequence of pGX9247: V2L2 with
      Rhesus Fc in pGX0001; DMAb-antiPcrV

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
```

-continued

```
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ser Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Val Cys Asn
        195                 200                 205

Val Asn His Lys Pro Ser Asn Thr Lys Val Asp Lys Arg Val Glu Ile
    210                 215                 220

Lys Thr Cys Gly Gly Gly Ser Lys Pro Pro Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Asp Val Lys Phe Asn Trp Tyr
        275                 280                 285

Val Asn Gly Ala Glu Val His His Ala Gln Thr Lys Pro Arg Glu Thr
    290                 295                 300

Gln Tyr Asn Ser Thr Tyr Arg Val Val Ser Val Leu Thr Val Thr His
305                 310                 315                 320

Gln Asp Trp Leu Asn Gly Lys Glu Tyr Thr Cys Lys Val Ser Asn Lys
                325                 330                 335

Ala Leu Pro Ala Pro Ile Gln Lys Thr Ile Ser Lys Asp Lys Gly Gln
            340                 345                 350

Pro Arg Glu Pro Gln Val Tyr Thr Leu Pro Pro Ser Arg Glu Glu Leu
        355                 360                 365

Thr Lys Asn Gln Val Ser Leu Thr Cys Leu Val Lys Gly Phe Tyr Pro
    370                 375                 380

Ser Asp Ile Val Val Glu Trp Glu Ser Ser Gly Gln Pro Glu Asn Thr
385                 390                 395                 400

Tyr Lys Thr Thr Pro Pro Val Leu Asp Ser Asp Gly Ser Tyr Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Val Ser Pro Arg Gly Arg Lys Arg Arg Ser Gly Ser
    450                 455                 460

Gly Ala Thr Asn Phe Ser Leu Leu Lys Gln Ala Gly Asp Val Glu Glu
465                 470                 475                 480

Asn Pro Gly Pro Met Val Leu Gln Thr Gln Val Phe Ile Ser Leu Leu
                485                 490                 495
```

```
Leu Trp Ile Ser Gly Ala Tyr Gly Ala Ile Gln Met Thr Gln Ser Pro
            500                 505                 510

Ser Ser Leu Ser Ala Ser Val Gly Asp Arg Val Thr Ile Thr Cys Arg
        515                 520                 525

Ala Ser Gln Gly Ile Arg Asn Asp Leu Gly Trp Tyr Gln Gln Lys Pro
    530                 535                 540

Gly Lys Ala Pro Lys Leu Leu Ile Tyr Ser Ala Ser Thr Leu Gln Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Leu Gln Asp Tyr Asn Tyr Pro Trp Thr Phe Gly Gln Gly Thr Lys Val
        595                 600                 605

Glu Ile Lys Arg Ala Val Ala Ala Pro Ser Val Phe Ile Phe Pro Pro
    610                 615                 620

Ser Glu Asp Gln Val Lys Ser Gly Thr Val Ser Val Val Cys Leu Leu
625                 630                 635                 640

Asn Asn Phe Tyr Pro Arg Glu Ala Ser Val Lys Trp Lys Val Asp Gly
                645                 650                 655

Val Leu Lys Thr Gly Asn Ser Gln Glu Ser Val Thr Glu Gln Asp Ser
            660                 665                 670

Lys Asp Asn Thr Tyr Ser Leu Ser Ser Thr Leu Thr Leu Ser Ser Thr
        675                 680                 685

Asp Tyr Gln Ser His Asn Val Tyr Ala Cys Glu Val Thr His Gln Gly
    690                 695                 700

Leu Ser Ser Pro Val Thr Lys Ser Phe Asn Arg Gly Glu Cys
705                 710                 715


<210> SEQ ID NO 9
<211> LENGTH: 2127
<212> TYPE: DNA
<213> ORGANISM: Artificial Sequence
<220> FEATURE:
<223> OTHER INFORMATION: nucleotide sequence of pGX9248: Pseudo-V2L2MD
      rbFc; DMAb-antiPcrV

<400> SEQUENCE: 9

gaagtgcagc tgctggaatc tggagggggc ctggtgcagc ccggcggcag cctgaggctg     60

tcctgcgccg ccagcggctt caccttctcc agctacgcca tgaactgggt gcgccaggcc    120

ccaggcaagg gactggagtg ggtgtccgcc atcaccatga gcggcatcac cgcctactac    180

accgacgacg tgaagggccg cttcaccatc tcccgggaca acagcaagaa caccctgtac    240

ctgcagatga actccctgag ggccgaggac accgccgtgt actactgcgc caaggaggag    300

ttcctgccag gaacccacta ctactacgga atggacgtgt ggggacaggg aaccaccgtg    360

accgtgtcca gcggccagcc caaggccccc agcgtgttcc cactggcccc atgctgcggc    420

gacacccccct ccagcaccgt gaccctggga tgcctggtga agggatacct gccagagcca    480

gtgaccgtga cctggaactc cggcaccctg accaacggcg tgaggacctt cccaagcgtg    540

cgccagtcca gcggactgta ctccctgtcc agcgtggtga gcgtgacctc cagctcccag    600

ccagtgacct gcaacgtggc ccacccagcc accaacacca aggtggacaa gaccgtggcc    660

ccaagcacct gctccaagcc aacctgccct cctcccgagc tgctgggcgg cccctccgtg    720

ttcatcttcc ctcccaagcc caaggacacc ctgatgatct ccaggacccc agaggtgacc    780
```

```
tgcgtggtgg tggacgtgag ccaggacgac cccgaggtgc agttcacctg gtacatcaac    840

aacgagcagg tgcggaccgc ccgccctccc ctgcgcgagc agcagttcaa ctccaccatc    900

cgggtggtga gcaccctgcc aatcacccac caggactggc tgaggggcaa ggagttcaag    960

tgcaaggtgc acaacaaggc cctgcccgcc cccatcgaga agaccatcag caaggccagg   1020

ggccagccac tggagcccaa ggtgtacacc atgggccctc cccgcgagga gctgagctcc   1080

aggagcgtgt ccctgacctg catgatcaac ggcttctacc ccagcgacat ctccgtggag   1140

tgggagaaga acggcaaggc cgaggacaac tacaagacca ccccagccgt gctggacagc   1200

gacggctcct acttcctgta caacaagctg tccgtgccca ccagcgagtg gcagcggggc   1260

gacgtgttca cctgctccgt gatgcacgag gccctgcaca accactacac ccagaagagc   1320

atctccagga gccccggcaa gaggggaagg aagcgccggt ccggcagcgg agccaccaac   1380

ttcagcctgc tgaagcaggc cggcgacgtg gaggagaacc caggaccaat ggtgctgcag   1440

acccaggtgt tcatctccct gctgctgtgg atcagcggag cctacggagc catccagatg   1500

acccagtccc ccagctccct gtccgccagc gtgggcgaca gggtgaccat cacctgcagg   1560

gccagccagg gcatcaggaa cgacctgggc tggtaccagc agaagcccgg caaggccccc   1620

aagctgctga tctactccgc cagcaccctg cagtccggag tgcccagccg gttctccggc   1680

agcggctccg gaaccgactt caccctgacc atcagctccc tgcagcccga ggacttcgcc   1740

acctactact gcctgcagga ctacaactac ccctggacct tcggccaggg caccaaggtg   1800

gagatcaaga ggcagccagc cgtgacccca tccgtgatcc tgttccctcc ctcctccgag   1860

gagctgaagg acaacaaggc caccctggtg tgcctgatct ccgacttcta cccccgcacc   1920

gtgaaggtga actggaaggc cgacggaaac agcgtgaccc agggagtgga caccacccag   1980

ccaagcaagc agtccaacaa caagtacgcc gccagctcct tcctgcacct gaccgccaac   2040

cagtggaaga gctaccagtc cgtgacctgt caggtcaccc acgaagggca caccgtcgaa   2100

aaatctctgg cccccgccga atgttct                                       2127
```

```
<210> SEQ ID NO 10
<211> LENGTH: 709
<212> TYPE: PRT
<213> ORGANISM: Artificial Sequence
<220> FEATURE:
<223> OTHER INFORMATION: amino acid sequence of pGX9248: Pseudo-V2L2MD
      rbFc; DMAb-antiPcrV

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Tyr Gly Met Asp
            100                 105                 110
```

```
Val Trp Gly Gln Gly Thr Thr Val Thr Val Ser Ser Gly Gln Pro Lys
        115                 120                 125

Ala Pro Ser Val Phe Pro Leu Ala Pro Cys Cys Gly Asp Thr Pro Ser
    130                 135                 140

Ser Thr Val Thr Leu Gly Cys Leu Val Lys Gly Tyr Leu Pro Glu Pro
145                 150                 155                 160

Val Thr Val Thr Trp Asn Ser Gly Thr Leu Thr Asn Gly Val Arg Thr
                165                 170                 175

Phe Pro Ser Val Arg Gln Ser Ser Gly Leu Tyr Ser Leu Ser Ser Val
            180                 185                 190

Val Ser Val Thr Ser Ser Ser Gln Pro Val Thr Cys Asn Val Ala His
        195                 200                 205

Pro Ala Thr Asn Thr Lys Val Asp Lys Thr Val Ala Pro Ser Thr Cys
    210                 215                 220

Ser Lys Pro Thr Cys Pro Pro Pro Glu Leu Leu Gly Gly Pro Ser Val
225                 230                 235                 240

Phe Ile Phe Pro Pro Lys Pro Lys Asp Thr Leu Met Ile Ser Arg Thr
                245                 250                 255

Pro Glu Val Thr Cys Val Val Val Asp Val Ser Gln Asp Asp Pro Glu
            260                 265                 270

Val Gln Phe Thr Trp Tyr Ile Asn Asn Glu Gln Val Arg Thr Ala Arg
        275                 280                 285

Pro Pro Leu Arg Glu Gln Gln Phe Asn Ser Thr Ile Arg Val Val Ser
    290                 295                 300

Thr Leu Pro Ile Thr His Gln Asp Trp Leu Arg Gly Lys Glu Phe Lys
305                 310                 315                 320

Cys Lys Val His Asn Lys Ala Leu Pro Ala Pro Ile Glu Lys Thr Ile
                325                 330                 335

Ser Lys Ala Arg Gly Gln Pro Leu Glu Pro Lys Val Tyr Thr Met Gly
            340                 345                 350

Pro Pro Arg Glu Glu Leu Ser Ser Arg Ser Val Ser Leu Thr Cys Met
        355                 360                 365

Ile Asn Gly Phe Tyr Pro Ser Asp Ile Ser Val Glu Trp Glu Lys Asn
    370                 375                 380

Gly Lys Ala Glu Asp Asn Tyr Lys Thr Thr Pro Ala Val Leu Asp Ser
385                 390                 395                 400

Asp Gly Ser Tyr Phe Leu Tyr Asn Lys Leu Ser Val Pro Thr Ser Glu
                405                 410                 415

Trp Gln Arg Gly Asp Val Phe Thr Cys Ser Val Met His Glu Ala Leu
            420                 425                 430

His Asn His Tyr Thr Gln Lys Ser Ile Ser Arg Ser Pro Gly Lys Arg
        435                 440                 445

Gly Arg Lys Arg Arg Ser Gly Ser Gly Ala Thr Asn Phe Ser Leu Leu
    450                 455                 460

Lys Gln Ala Gly Asp Val Glu Glu Asn Pro Gly Pro Met Val Leu Gln
465                 470                 475                 480

Thr Gln Val Phe Ile Ser Leu Leu Leu Trp Ile Ser Gly Ala Tyr Gly
                485                 490                 495

Ala Ile Gln Met Thr Gln Ser Pro Ser Ser Leu Ser Ala Ser Val Gly
            500                 505                 510

Asp Arg Val Thr Ile Thr Cys Arg Ala Ser Gln Gly Ile Arg Asn Asp
        515                 520                 525

Leu Gly Trp Tyr Gln Gln Lys Pro Gly Lys Ala Pro Lys Leu Leu Ile
```

```
    530                 535                 540

Tyr Ser Ala Ser Thr Leu Gln Ser Gly Val Pro Ser Arg Phe Ser Gly
545                 550                 555                 560

Ser Gly Ser Gly Thr Asp Phe Thr Leu Thr Ile Ser Ser Leu Gln Pro
                565                 570                 575

Glu Asp Phe Ala Thr Tyr Tyr Cys Leu Gln Asp Tyr Asn Tyr Pro Trp
            580                 585                 590

Thr Phe Gly Gln Gly Thr Lys Val Glu Ile Lys Arg Gln Pro Ala Val
        595                 600                 605

Thr Pro Ser Val Ile Leu Phe Pro Pro Ser Ser Glu Glu Leu Lys Asp
    610                 615                 620

Asn Lys Ala Thr Leu Val Cys Leu Ile Ser Asp Phe Tyr Pro Arg Thr
625                 630                 635                 640

Val Lys Val Asn Trp Lys Ala Asp Gly Asn Ser Val Thr Gln Gly Val
                645                 650                 655

Asp Thr Thr Gln Pro Ser Lys Gln Ser Asn Asn Lys Tyr Ala Ala Ser
            660                 665                 670

Ser Phe Leu His Leu Thr Ala Asn Gln Trp Lys Ser Tyr Gln Ser Val
        675                 680                 685

Thr Cys Gln Val Thr His Glu Gly His Thr Val Glu Lys Ser Leu Ala
    690                 695                 700

Pro Ala Glu Cys Ser
705
```

<210> SEQ ID NO 11
<211> LENGTH: 1362
<212> TYPE: DNA
<213> ORGANISM: Artificial Sequence
<220> FEATURE:
<223> OTHER INFORMATION: nucleotide sequence of pGX9257 hc: Pseudo-V2L2MD in pGX0003 (sCMV-light chain, hCMV-heavy chain); DMAb-antiPcrV

<400> SEQUENCE: 11

```
gaggtgcagc tgctggagtc aggaggagga ctggtgcagc ccggcggatc actgcgactg     60

agctgcgcag cttccggctt caccttcagc agctatgcca tgaactgggt ccgacaggct    120

cctggcaagg gactggaatg ggtgagtgca atcaccatgt cagggattac tgcctactat    180

accgacgatg tgaaaggccg attcactatc tctagggaca acagtaagaa taccctgtac    240

ctgcagatga attccctgcg cgctgaggat acagcagtgt actattgcgc caaggaggaa    300

ttcctgccag ggactcacta ctattacgga atggacgtgt ggggacaggg aaccacagtc    360

accgtgtcta gtgcaagcac aaaaggcccc tccgtgtttc ccctggcccc ttcaagcaag    420

tctacaagtg ggggcactgc agccctggga tgtctggtga aggattactt ccctgagcca    480

gtcaccgtga gctggaactc cggcgccctg acttccggag tccatacctt tcctgctgtg    540

ctgcagtcct ctggcctgta tagcctgagt tcagtggtca ccgtcccaag ctcctctctg    600

ggaacacaga cttacatctg caacgtgaat cacaaaccaa gcaatacaaa ggtcgacaag    660

aaagtggaac ccaaatcctg tgataagacc catacatgcc ctccctgtcc agcacctgag    720

ctgctgggag ggccaagcgt gttcctgttt ccacccaagc ctaaagacac actgatgatt    780

tctcggaccc ccgaagtcac atgcgtggtc gtggacgtga gccacgagga ccccgaagtc    840

aagtttaact ggtacgtgga tggcgtcgag gtgcataatg ccaagaccaa accacgagag    900

gaacagtata actctacata cagggtcgtg agtgtcctga ctgtgctgca ccaggactgg    960
```

ctgaacggga aggagtacaa gtgcaaagtg tccaacaagg ccctgccagc tcccatcgag 1020
aagaccattt ctaaggccaa aggccagcca agagaacccc aggtgtatac actgcctcca 1080
agtcgggacg agctgactaa aaaccaggtc tctctgacct gtctggtgaa gggattctac 1140
ccttccgata tcgctgtgga gtgggaatct aatgggcagc cagaaaacaa ttataagact 1200
acccctcccg tgctggactc tgatggaagt ttctttctgt actccaaact gaccgtggac 1260
aagtctagat ggcagcaggg gaacgtcttt tcatgcagcg tgatgcatga ggccctgcac 1320
aatcattaca ctcagaaatc cctgtctctg agtcctggga aa 1362

<210> SEQ ID NO 12
<211> LENGTH: 454
<212> TYPE: PRT
<213> ORGANISM: Artificial Sequence
<220> FEATURE:
<223> OTHER INFORMATION: amino acid sequence of pGX9257 hc: Pseudo-
V2L2MD in pGX0003 (sCMV-light chain, hCMV-heavy chain); DMAb-
antiPcrV

<400> SEQUENCE: 12

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Ala Ile Thr Met Ser Gly Ile Thr Ala Tyr Tyr Thr Asp Asp Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Glu Phe Leu Pro Gly Thr His Tyr Tyr Tyr Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 13
<211> LENGTH: 2151
<212> TYPE: DNA
<213> ORGANISM: Artificial Sequence
<220> FEATURE:
<223> OTHER INFORMATION: nucleotide sequence of pGX9258: Psuedo-V2L2MD-
      YTE only in pGX0001; DMAb-antiPcrV

<400> SEQUENCE: 13
gaggtgcagc tgctggagtc aggaggagga ctggtgcagc ccggcggatc actgcgactg 60
agctgcgcag cttccggctt caccttcagc agctatgcca tgaactgggt ccgacaggct 120
cctggcaagg gactggaatg ggtgagtgca atcaccatgt cagggattac tgcctactat 180
accgacgatg tgaaaggccg attcactatc tctagggaca acagtaagaa taccctgtac 240
ctgcagatga attccctgcg cgctgaggat acagcagtgt actattgcgc caaggaggaa 300
ttcctgccag ggactcacta ctattacgga atggacgtgt ggggacaggg aaccacagtc 360
accgtgtcta gtgcaagcac aaaaggcccc tccgtgtttc ccctggcccc ttcaagcaag 420
tctacaagtg gggcactgc agccctggga tgtctggtga aggattactt ccctgagcca 480
gtcaccgtga gctggaactc cggcgccctg acttccggag tccatacctt tcctgctgtg 540
ctgcagtcct ctggcctgta tagcctgagt tcagtggtca ccgtcccaag ctcctctctg 600
ggaacacaga cttacatctg caacgtgaat cacaaaccaa gcaatacaaa ggtcgacaag 660
aaagtggaac ccaaatcctg tgataagacc catacatgcc ctccctgtcc agcacctgag 720
ctgctgggag ggccaagcgt gttcctgttt ccacccaagc ctaaagacac actgtacatt 780
actcgggagc ccgaagtcac atgcgtggtc gtggacgtga gccacgagga ccccgaagtc 840
aagtttaact ggtacgtgga tggcgtcgag gtgcataatg ccaagaccaa accacgagag 900
gaacagtata actctacata cagggtcgtg agtgtcctga ctgtgctgca ccaggactgg 960
ctgaacggga aggagtacaa gtgcaaagtg tccaacaagg ccctgccagc tcccatcgag 1020
aagaccattt ctaaggccaa aggccagcca agagaacccc aggtgtatac actgcctcca 1080
agtcgggacg agctgactaa aaaccaggtc tctctgacct gtctggtgaa gggattctac 1140
ccttccgata tcgctgtgga gtgggaatct aatgggcagc cagaaaacaa ttataagact 1200
acccctcccg tgctggactc tgatggaagt ttctttctgt actccaaact gaccgtggac 1260
aagtctagat ggcagcaggg gaacgtcttt tcatgcagcg tgatgcatga ggccctgcac 1320
aatcattaca ctcagaaatc cctgtctctg agtcctggga aacggggccg caagaggaga 1380
tcaggaagcg gggccaccaa cttctccctg ctgaagcagg ctggcgatgt ggaggaaaat 1440
cctggaccaa tggtcctgca gactcaggtg tttatctcac tgctgctgtg gattagcgga 1500
gcatacgggg ccattcagat gacccagtcc cccagttcac tgtccgcttc tgtcggcgac 1560
agagtgacta tcacctgtcg ggcaagccag ggaattcgca acgatctggg gtggtatcag 1620
cagaagcctg ggaaagctcc aaagctgctg atctacagtg catcaactct gcagtcagga 1680
gtgcctagcc ggttcagcgg ctccggatct ggaaccgact ttacactgac tattagctcc 1740
ctgcagccag aggacttcgc cacatattac tgcctgcagg attataatta cccctggaca 1800
tttggccagg gaactaaagt ggaaatcaag cgcacagtcg ctgcacctag cgtgttcatc 1860
tttccaccct cagacgagca gctgaagtcc ggaactgctt ctgtggtgtg cctgctgaac 1920
aatttctatc caagggaagc aaaagtccag tggaaggtgg ataacgccct gcagtcaggc 1980
aatagccagg agtccgtgac cgaacaggac tctaaagata gtacatacag tctgtcaaac 2040
accctgacac tgagcaaggc tgattatgag aagcacaaag tgtacgcatg cgaagtcacc 2100
caccaggggc tgtcctcacc agtcacaaaa tctttcaatc ggggagaatg c 2151

<210> SEQ ID NO 14
<211> LENGTH: 717
<212> TYPE: PRT
<213> ORGANISM: Artificial Sequence
<220> FEATURE:
<223> OTHER INFORMATION: amino acid sequence of pGX9258: Psuedo-V2L2MD-
YTE only in pGX0001; DMAb-antiPcrV

<400> SEQUENCE: 14

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Ala Ile Thr Met Ser Gly Ile Thr Ala Tyr Tyr Thr Asp Asp Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Glu Phe Leu Pro Gly Thr His Tyr Tyr Tyr Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

-continued

```
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Tyr Ile Thr Arg Glu Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Arg Gly Arg Lys Arg Arg Ser Gly Ser Gly
    450                 455                 460

Ala Thr Asn Phe Ser Leu Leu Lys Gln Ala Gly Asp Val Glu Glu Asn
465                 470                 475                 480

Pro Gly Pro Met Val Leu Gln Thr Gln Val Phe Ile Ser Leu Leu Leu
                485                 490                 495

Trp Ile Ser Gly Ala Tyr Gly Ala Ile Gln Met Thr Gln Ser Pro Ser
            500                 505                 510

Ser Leu Ser Ala Ser Val Gly Asp Arg Val Thr Ile Thr Cys Arg Ala
        515                 520                 525

Ser Gln Gly Ile Arg Asn Asp Leu Gly Trp Tyr Gln Gln Lys Pro Gly
    530                 535                 540

Lys Ala Pro Lys Leu Leu Ile Tyr Ser Ala Ser Thr Leu Gln Ser Gly
545                 550                 555                 560

Val Pro Ser Arg Phe Ser Gly Ser Gly Ser Gly Thr Asp Phe Thr Leu
                565                 570                 575

Thr Ile Ser Ser Leu Gln Pro Glu Asp Phe Ala Thr Tyr Tyr Cys Leu
```

```
            580                 585                 590

Gln Asp Tyr Asn Tyr Pro Trp Thr Phe Gly Gln Gly Thr Lys Val Glu
        595                 600                 605

Ile Lys Arg Thr Val Ala Ala Pro Ser Val Phe Ile Phe Pro Pro Ser
    610                 615                 620

Asp Glu Gln Leu Lys Ser Gly Thr Ala Ser Val Val Cys Leu Leu Asn
625                 630                 635                 640

Asn Phe Tyr Pro Arg Glu Ala Lys Val Gln Trp Lys Val Asp Asn Ala
                645                 650                 655

Leu Gln Ser Gly Asn Ser Gln Glu Ser Val Thr Glu Gln Asp Ser Lys
            660                 665                 670

Asp Ser Thr Tyr Ser Leu Ser Asn Thr Leu Thr Leu Ser Lys Ala Asp
        675                 680                 685

Tyr Glu Lys His Lys Val Tyr Ala Cys Glu Val Thr His Gln Gly Leu
    690                 695                 700

Ser Ser Pro Val Thr Lys Ser Phe Asn Arg Gly Glu Cys
705                 710                 715


<210> SEQ ID NO 15
<211> LENGTH: 642
<212> TYPE: DNA
<213> ORGANISM: Artificial Sequence
<220> FEATURE:
<223> OTHER INFORMATION: nucleotide sequence of pGX9257 lc: Pseudo-
      V2L2MD in pGX0003 (sCMV-light chain, hCMV-heavy chain); DMAb-
      antiPcrV

<400> SEQUENCE: 15

gccattcaga tgacccagtc ccccagttca ctgtccgctt ctgtcggcga cagagtgact      60

atcacctgtc gggcaagcca gggaattcgc aacgatctgg ggtggtatca gcagaagcct     120

gggaaagctc caaagctgct gatctacagt gcatcaactc tgcagtcagg agtgcctagc     180

cggttcagcg gctccggatc tggaaccgac tttacactga ctattagctc cctgcagcca     240

gaggacttcg ccacatatta ctgcctgcag gattataatt acccctggac atttggccag     300

ggaactaaag tggaaatcaa gcgcacagtc gctgcaccta gcgtgttcat ctttccaccc     360

tcagacgagc agctgaagtc cggaactgct tctgtggtgt gcctgctgaa caatttctat     420

ccaagggaag caaaagtcca gtggaaggtg gataacgccc tgcagtcagg caatagccag     480

gagtccgtga ccgaacagga ctctaaagat agtacataca gtctgtcaaa caccctgaca     540

ctgagcaagg ctgattatga gaagcacaaa gtgtacgcat gcgaagtcac ccaccagggg     600

ctgtcctcac cagtcacaaa atctttcaat cggggagaat gc                        642


<210> SEQ ID NO 16
<211> LENGTH: 214
<212> TYPE: PRT
<213> ORGANISM: Artificial Sequence
<220> FEATURE:
<223> OTHER INFORMATION: amino acid sequence of pGX9257 lc: Pseudo-
      V2L2MD in pGX0003 (sCMV-light chain, hCMV-heavy chain); DMAb-
      antiPcrV

<400> SEQUENCE: 16

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
```

```
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 17
<211> LENGTH: 2949
<212> TYPE: DNA
<213> ORGANISM: Artificial Sequence
<220> FEATURE:
<223> OTHER INFORMATION: nucleotide sequence of pGX9213: Bispecific
      Pseudomonas (Bis4-V2L2MD/Psl0096); DMAb-BiSPA

<400> SEQUENCE: 17

gaagtgcagc tgctggagtc agggggaggg ctggtgcagc ccggcggcag cctgcgactg     60

tcttgcgccg ctagtggctt caccttcagc agctatgcta tgaactgggt ccgacaggca    120

ccaggaaagg gactggaatg ggtgtctgcc atcaccatga gtggaattac agcttactat    180

actgacgatg tgaaggggag attcacaatc tcacgggaca acagcaaaaa tactctgtac    240

ctgcagatga atagcctgag ggcagaggat accgccgtgt actattgcgc caaggaggaa    300

ttcctgcctg gcacacacta ctattacgga atggacgtgt ggggccaggg aaccacagtc    360

accgtgtcta gtgcttcaac aaaggggcca agcgtgtttc cactggcacc ctcaagcaaa    420

tcaaccagcg ggggcacagc agccctggga tgtctggtga aggattactt ccccgagcct    480

gtcaccgtgt catggaacag cggagccctg acctccggag tccacacatt tcctgctgtg    540

ctgcagtcct ctgggctgta ttctctgagt tcagtggtca cagtcccaag ctcctctctg    600

ggcacacaga cttacatctg caacgtgaat cataagccat ccaatactaa ggtcgacaaa    660

cgggtggagc ccaaatcttg tggcggcggc ggcagcggcg gcggcggcag ccaggtccag    720

ctgcaggaga gcggacctgg actggtgaag ccatccgaaa cactgtctct gacctgcacc    780

gtgagcggcg gcagcatctc tccatattac tggacttgga ttaggcagcc ccctggcaag    840

tgtctggagc tgatcgggta cattcacagt tcaggctata ccgactacaa cccctccctg    900

aagtctagag tgactatcag tggcgatacc tcaaagaaac agttctccct gaaactgagc    960

tccgtcactg ctgcagacac cgccgtgtat tactgcgcac gcgccgactg ggatcgactg   1020
```

```
cgcgctctgg atatctgggg acaggggact atggtcaccg tgtctagtgg gggcggaggg   1080
agtggcggag ggggctcagg agggggcgga agcgggggcg gagggtccga cattcagctg   1140
acccagagcc cctcaagcct gagtgcctca gtcggcgatc gcgtgactat cacctgtcga   1200
gctagccagt ccattaggtc ccatctgaac tggtatcagc agaagcccgg aaaagcacct   1260
aagctgctga tctacggcgc cagcaatctg cagtccggag tgccctctag gttctctggc   1320
agtggatcag ggacagactt tacactgact atttcctctc tgcagcctga ggatttcgca   1380
acttattact gccagcagag caccggcgcc tggaactggt ttggctgtgg aaccaaggtg   1440
gaaatcaaag gcggaggggg ctctggaggg ggcggaagtg acaagaccca cacatgccca   1500
ccctgtccag caccagagct gctgggcggc ccatccgtgt tcctgtttcc tccaaagcct   1560
aaagatacac tgatgattag cagaacaccc gaagtcactt gcgtggtcgt ggacgtgtcc   1620
cacgaggacc ccgaagtcaa gtttaactgg tacgtggacg gcgtcgaggt gcataatgcc   1680
aagaccaaac cccgagagga acagtataac tcaacctaca gggtcgtgag cgtcctgaca   1740
gtgctgcatc aggattggct gaacggcaag gagtacaagt gcaaagtgtc taataaggct   1800
ctgcctgcac caatcgagaa aactattagc aaggccaaag gccagcctag agaaccacag   1860
gtgtataccc tgcccccttc tcgggaggaa atgacaaaga accaggtcag cctgacttgt   1920
ctggtgaaag gcttctaccc ttctgacatc gctgtggagt gggaaagtaa tggacagcca   1980
gaaaacaatt ataagactac cccacccgtc ctggacagtg atggctcatt ctttctgtac   2040
agtaagctga ccgtggataa atcaaggtgg cagcagggaa acgtctttag ctgctccgtg   2100
atgcacgagg ccctgcacaa tcattacaca cagaagtctc tgagtctgtc acctggcaag   2160
cgaggaagga aaaggagaag cgggtccgga gcaaccaact tcagcctgct gaaacaggct   2220
ggggacgtgg aggaaaatcc cggccctatg gtcctgcaga cccaggtgtt tatctccctg   2280
ctgctgtgga tttctggggc ctacggcgct atccagatga cacagtctcc tagttcactg   2340
tctgcaagtg tcggcgacag agtgactatc acctgtcggg cttcccaggg aattcgcaac   2400
gatctggggt ggtatcagca gaaaccagga aaggctccca aactgctgat ctactcagca   2460
agcacactgc agagtggggt gccatcaaga ttctccggat ctgggagtgg cactgacttc   2520
accctgacta ttagctccct gcagccagag gacttcgcca cctattactg cctgcaggat   2580
tataattacc cctggacatt tggacagggg actaaggtgg agatcaaacg gactgtcgcc   2640
gctcccagcg tgttcatttt tcctccatcc gacgaacagc tgaagagcgg aaccgcatcc   2700
gtggtgtgcc tgctgaacaa tttctatcct cgcgaagcaa aggtccagtg gaaagtggat   2760
aacgccctgc agagcggcaa ttcccaggag tctgtgactg aacaggacag taaggattca   2820
acctacagcc tgtctagtac cctgacactg tccaaagctg actatgagaa gcataaagtg   2880
tacgcatgtg aggtcaccca ccaggggctg tccagtccag tcaccaagtc tttcaatagg   2940
ggcgaatgc                                                           2949
```

<210> SEQ ID NO 18
<211> LENGTH: 983
<212> TYPE: PRT
<213> ORGANISM: Artificial Sequence
<220> FEATURE:
<223> OTHER INFORMATION: amino acid sequence of pGX9213: Bispecific Pseudomonas (Bis4-V2L2MD/Psl0096); DMAb-BiSPA

<400> SEQUENCE: 18

Glu Val Gln Leu Leu Glu Ser Gly Gly Gly Leu Val Gln Pro Gly Gly

-continued

```
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Gly Ser Gly Gly Gly Gly Ser Gln Val Gln
225                 230                 235                 240

Leu Gln Glu Ser Gly Pro Gly Leu Val Lys Pro Ser Glu Thr Leu Ser
                245                 250                 255

Leu Thr Cys Thr Val Ser Gly Gly Ser Ile Ser Pro Tyr Tyr Trp Thr
            260                 265                 270

Trp Ile Arg Gln Pro Pro Gly Lys Cys Leu Glu Leu Ile Gly Tyr Ile
        275                 280                 285

His Ser Ser Gly Tyr Thr Asp Tyr Asn Pro Ser Leu Lys Ser Arg Val
    290                 295                 300

Thr Ile Ser Gly Asp Thr Ser Lys Lys Gln Phe Ser Leu Lys Leu Ser
305                 310                 315                 320

Ser Val Thr Ala Ala Asp Thr Ala Val Tyr Tyr Cys Ala Arg Ala Asp
                325                 330                 335

Trp Asp Arg Leu Arg Ala Leu Asp Ile Trp Gly Gln Gly Thr Met Val
            340                 345                 350

Thr Val Ser Ser Gly Gly Gly Gly Ser Gly Gly Gly Gly Ser Gly Gly
        355                 360                 365

Gly Gly Ser Gly Gly Gly Gly Ser Asp Ile Gln Leu Thr Gln Ser Pro
    370                 375                 380

Ser Ser Leu Ser Ala Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
                405                 410                 415

Gly Lys Ala Pro Lys Leu Leu Ile Tyr Gly Ala Ser Asn Leu Gln Ser
            420                 425                 430
```

```
Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460

Gln Gln Ser Thr Gly Ala Trp Asn Trp Phe Gly Cys Gly Thr Lys Val
465                 470                 475                 480

Glu Ile Lys Gly Gly Gly Gly Ser Gly Gly Gly Gly Ser Asp Lys Thr
                485                 490                 495

His Thr Cys Pro Pro Cys Pro Ala Pro Glu Leu Leu Gly Gly Pro Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

Arg Gly Arg Lys Arg Arg Ser Gly Ser Gly Ala Thr Asn Phe Ser Leu
                725                 730                 735

Leu Lys Gln Ala Gly Asp Val Glu Glu Asn Pro Gly Pro Met Val Leu
            740                 745                 750

Gln Thr Gln Val Phe Ile Ser Leu Leu Leu Trp Ile Ser Gly Ala Tyr
        755                 760                 765

Gly Ala Ile Gln Met Thr Gln Ser Pro Ser Ser Leu Ser Ala Ser Val
    770                 775                 780

Gly Asp Arg Val Thr Ile Thr Cys Arg Ala Ser Gln Gly Ile Arg Asn
785                 790                 795                 800

Asp Leu Gly Trp Tyr Gln Gln Lys Pro Gly Lys Ala Pro Lys Leu Leu
                805                 810                 815

Ile Tyr Ser Ala Ser Thr Leu Gln Ser Gly Val Pro Ser Arg Phe Ser
            820                 825                 830

Gly Ser Gly Ser Gly Thr Asp Phe Thr Leu Thr Ile Ser Ser Leu Gln
        835                 840                 845
```

```
Pro Glu Asp Phe Ala Thr Tyr Tyr Cys Leu Gln Asp Tyr Asn Tyr Pro
    850                 855                 860

Trp Thr Phe Gly Gln Gly Thr Lys Val Glu Ile Lys Arg Thr Val Ala
865                 870                 875                 880

Ala Pro Ser Val Phe Ile Phe Pro Pro Ser Asp Glu Gln Leu Lys Ser
                885                 890                 895

Gly Thr Ala Ser Val Val Cys Leu Leu Asn Asn Phe Tyr Pro Arg Glu
            900                 905                 910

Ala Lys Val Gln Trp Lys Val Asp Asn Ala Leu Gln Ser Gly Asn Ser
        915                 920                 925

Gln Glu Ser Val Thr Glu Gln Asp Ser Lys Asp Ser Thr Tyr Ser Leu
    930                 935                 940

Ser Ser Thr Leu Thr Leu Ser Lys Ala Asp Tyr Glu Lys His Lys Val
945                 950                 955                 960

Tyr Ala Cys Glu Val Thr His Gln Gly Leu Ser Ser Pro Val Thr Lys
                965                 970                 975

Ser Phe Asn Arg Gly Glu Cys
            980


<210> SEQ ID NO 19
<211> LENGTH: 2136
<212> TYPE: DNA
<213> ORGANISM: Artificial Sequence
<220> FEATURE:
<223> OTHER INFORMATION: nucleotide sequence of pGX9215: Pseudo-Ps10096;
      DMAb-antiPsl

<400> SEQUENCE: 19

caggtgcagc tgcaggagtc tggacccgga ctggtcaagc ctagcgaaac tctgtccctg      60

acttgcaccg tgtccggcgg atcaatcagc ccatactatt ggacctggat tcgccagccc     120

cctggcaagg gactggagct gatcggctac attcacagct ccggatacac cgactataac     180

ccatcactga aaagccgagt gacaatctct ggcgatacta gtaagaaaca gttcagcctg     240

aagctgtcta gtgtcacagc cgctgacact gcagtgtact attgcgcccg cgctgactgg     300

gatcgactgc gcgctctgga tatttggggg cagggcacta tggtcaccgt gagcagcgcc     360

tcaaccaaag gccctagcgt gtttccactg gcaccctcct ctaagtccac ctctgggggc     420

acagcagccc tgggatgtct ggtgaaggac tacttccccg agcctgtcac agtgtcctgg     480

aactctggag ccctgacctc cggggtccat acatttcccg ctgtgctgca gagttcaggg     540

ctgtactctc tgagctccgt ggtcaccgtg ccttctagtt cactgggcac acagacttat     600

atctgcaacg tgaatcacaa accttccaat acaaaggtcg acaagaaagt ggaaccaaaa     660

tcttgtgata agacccatac atgcccaccc tgtccagcac cagagctgct gggagggcca     720

tccgtgttcc tgtttcctcc aaagcccaaa gacaccctga tgattagccg gactccagaa     780

gtcacctgcg tggtcgtgga cgtgtcccac gaggaccccg aagtcaagtt caactggtac     840

gtggatggcg tcgaggtgca taatgccaag acaaaacccc gagaggaaca gtacaactcc     900

acttataggg tcgtgtctgt cctgaccgtg ctgcaccagg attggctgaa cgggaaggag     960

tataagtgca aagtgtctaa caaggccctg cctgccccaa tcgagaagac cattagcaag    1020

gccaaaggcc agcctagaga accacaggtg tacacactgc cccctagtcg ggacgagctg    1080

actaaaaacc aggtcagcct gacctgtctg gtgaagggct tctatccctc agatatcgct    1140

gtggagtggg aatctaatgg acagcctgaa aacaattaca agaccacacc acccgtgctg    1200

gacagtgatg gatcattctt tctgtatagc aaactgaccg tggacaagtc cagatggcag    1260
```

```
caggggaacg tctttagttg ctcagtgatg cacgaggccc tgcacaatca ttacactcag   1320

aaaagcctgt ccctgtctcc cggcaaacga ggaaggaaga ggagaagtgg atcaggggcc   1380

acaaacttca gcctgctgaa gcaggctggg gatgtggagg aaaatcccgg ccctatggtc   1440

ctgcagacac aggtgtttat cagtctgctg ctgtggattt caggggccta tggcgacatc   1500

cagctgactc agtcccctag ctccctgagc gcctccgtcg gagatagagt gactatcacc   1560

tgtcgggctt ctcagagtat tcgcagccat ctgaactggt accagcagaa gcccgggaaa   1620

gctcctaagc tgctgatcta tggagcatca aatctgcaga gcggagtgcc atcccggttc   1680

tcaggcagcg gcagcggaac cgactttaca ctgactattt ctagtctgca gcccgaggat   1740

ttcgcaacat actattgcca gcagtccact ggcgcctgga actggtttgg cggagggacc   1800

aaagtggaaa tcaagcgcac agtcgctgca cctagcgtgt tcatctttcc tccaagtgac   1860

gagcagctga agtctggcac cgccagtgtg gtgtgcctgc tgaacaattt ctacccaagg   1920

gaagcaaaag tccagtggaa ggtggataac gccctgcaga gcggaaattc ccaggagtct   1980

gtgacagaac aggacagtaa ggattcaact tactctctga gtaacaccct gacactgagc   2040

aaggctgact acgagaagca caaagtgtat gcatgcgagg tcacccacca ggggctgtcc   2100

agtccagtca ctaagtcctt caatagggga gaatgc                             2136
```

```
<210> SEQ ID NO 20
<211> LENGTH: 712
<212> TYPE: PRT
<213> ORGANISM: Artificial Sequence
<220> FEATURE:
<223> OTHER INFORMATION: amino acid sequence of pGX9215: Pseudo-Ps10096;
      DMAb-antiPsl

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Gly Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Arg Leu Arg Ala Leu Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Arg Gly Arg Lys Arg Arg Ser Gly Ser Gly Ala Thr Asn Phe Ser
    450                 455                 460

Leu Leu Lys Gln Ala Gly Asp Val Glu Glu Asn Pro Gly Pro Met Val
465                 470                 475                 480

Leu Gln Thr Gln Val Phe Ile Ser Leu Leu Leu Trp Ile Ser Gly Ala
                485                 490                 495

Tyr Gly Asp Ile Gln Leu Thr Gln Ser Pro Ser Ser Leu Ser Ala Ser
            500                 505                 510

Val Gly Asp Arg Val Thr Ile Thr Cys Arg Ala Ser Gln Ser Ile Arg
        515                 520                 525

Ser His Leu Asn Trp Tyr Gln Gln Lys Pro Gly Lys Ala Pro Lys Leu
    530                 535                 540

Leu Ile Tyr Gly Ala Ser Asn Leu Gln Ser Gly Val Pro Ser Arg Phe
545                 550                 555                 560

Ser Gly Ser Gly Ser Gly Thr Asp Phe Thr Leu Thr Ile Ser Ser Leu
                565                 570                 575

Gln Pro Glu Asp Phe Ala Thr Tyr Tyr Cys Gln Gln Ser Thr Gly Ala
            580                 585                 590

Trp Asn Trp Phe Gly Gly Gly Thr Lys Val Glu Ile Lys Arg Thr Val
        595                 600                 605

Ala Ala Pro Ser Val Phe Ile Phe Pro Pro Ser Asp Glu Gln Leu Lys
    610                 615                 620
```

```
Ser Gly Thr Ala Ser Val Val Cys Leu Leu Asn Asn Phe Tyr Pro Arg
625                 630                 635                 640

Glu Ala Lys Val Gln Trp Lys Val Asp Asn Ala Leu Gln Ser Gly Asn
                645                 650                 655

Ser Gln Glu Ser Val Thr Glu Gln Asp Ser Lys Asp Ser Thr Tyr Ser
            660                 665                 670

Leu Ser Asn Thr Leu Thr Leu Ser Lys Ala Asp Tyr Glu Lys His Lys
        675                 680                 685

Val Tyr Ala Cys Glu Val Thr His Gln Gly Leu Ser Ser Pro Val Thr
    690                 695                 700

Lys Ser Phe Asn Arg Gly Glu Cys
705                 710


<210> SEQ ID NO 21
<211> LENGTH: 2949
<212> TYPE: DNA
<213> ORGANISM: Artificial Sequence
<220> FEATURE:
<223> OTHER INFORMATION: nucleotide sequence of pGX9259: Bispecific
      Pseudomonas (Bis4-V2L2MD/Psl0096)-YTE only pGX0001; DMAb-BiSPA

<400> SEQUENCE: 21

gaagtgcagc tgctggagtc agggggaggg ctggtgcagc ccggcggcag cctgcgactg     60

tcttgcgccg ctagtggctt caccttcagc agctatgcta tgaactgggt ccgacaggca    120

ccaggaaagg gactggaatg ggtgtctgcc atcaccatga gtggaattac agcttactat    180

actgacgatg tgaaggggag attcacaatc tcacgggaca acagcaaaaa tactctgtac    240

ctgcagatga atagcctgag ggcagaggat accgccgtgt actattgcgc caaggaggaa    300

ttcctgcctg gcacacacta ctattacgga atggacgtgt ggggccaggg aaccacagtc    360

accgtgtcta gtgcttcaac aaaggggcca agcgtgtttc cactggcacc ctcaagcaaa    420

tcaaccagcg gggcacagc agccctggga tgtctggtga aggattactt ccccgagcct    480

gtcaccgtgt catggaacag cggagccctg acctccggag tccacacatt tcctgctgtg    540

ctgcagtcct ctgggctgta ttctctgagt tcagtggtca cagtcccaag ctcctctctg    600

ggcacacaga cttacatctg caacgtgaat cataagccat ccaatactaa ggtcgacaaa    660

cgggtggagc ccaaatcttg tggcggcggc ggcagcggcg gcggcggcag ccaggtccag    720

ctgcaggaga gcggacctgg actggtgaag ccatccgaaa cactgtctct gacctgcacc    780

gtgagcggcg gcagcatctc tccatattac tggacttgga ttaggcagcc ccctggcaag    840

tgtctggagc tgatcgggta cattcacagt tcaggctata ccgactacaa cccctccctg    900

aagtctagag tgactatcag tggcgatacc tcaaagaaac agttctccct gaaactgagc    960

tccgtcactg ctgcagacac cgccgtgtat tactgcgcac gcgccgactg ggatcgactg   1020

cgcgctctgg atatctgggg acaggggact atggtcaccg tgtctagtgg gggcggaggg   1080

agtggcggag ggggctcagg agggggcgga agcgggggcg gagggtccga cattcagctg   1140

acccagagcc cctcaagcct gagtgcctca gtcggcgatc gcgtgactat cacctgtcga   1200

gctagccagt ccattaggtc ccatctgaac tggtatcagc agaagcccgg aaaagcacct   1260

aagctgctga tctacggcgc cagcaatctg cagtccggag tgccctctag gttctctggc   1320

agtggatcag ggacagactt tacactgact atttcctctc tgcagcctga ggatttcgca   1380

acttattact gccagcagag caccggcgcc tggaactggt ttggctgtgg aaccaaggtg   1440

gaaatcaaag gcggaggggg ctctggaggg ggcggaagtg acaagaccca cacatgccca   1500
```

ccctgtccag caccagagct gctgggcggc ccatccgtgt tcctgtttcc tccaaagcct 1560
aaagatacac tgtatattac tagagagccc gaagtcactt gcgtggtcgt ggacgtgtcc 1620
cacgaggacc ccgaagtcaa gtttaactgg tacgtggacg gcgtcgaggt gcataatgcc 1680
aagaccaaac cccgagagga acagtataac tcaacctaca gggtcgtgag cgtcctgaca 1740
gtgctgcatc aggattggct gaacggcaag gagtacaagt gcaaagtgtc taataaggct 1800
ctgcctgcac caatcgagaa aactattagc aaggccaaag gccagcctag agaaccacag 1860
gtgtataccc tgccccccttc tcgggaggaa atgacaaaga accaggtcag cctgacttgt 1920
ctggtgaaag gcttctaccc ttctgacatc gctgtggagt gggaaagtaa tggacagcca 1980
gaaaacaatt ataagactac ccccacccgtc ctggacagtg atggctcatt ctttctgtac 2040
agtaagctga ccgtggataa atcaaggtgg cagcagggaa acgtctttag ctgctccgtg 2100
atgcacgagg ccctgcacaa tcattacaca cagaagtctc tgagtctgtc acctggcaag 2160
cgaggaagga aaaggagaag cgggtccgga gcaaccaact tcagcctgct gaaacaggct 2220
ggggacgtgg aggaaaatcc cggccctatg gtcctgcaga cccaggtgtt tatctccctg 2280
ctgctgtgga tttctggggc ctacggcgct atccagatga cacagtctcc tagttcactg 2340
tctgcaagtg tcggcgacag agtgactatc acctgtcggg cttcccaggg aattcgcaac 2400
gatctggggt ggtatcagca gaaaccagga aaggctccca aactgctgat ctactcagca 2460
agcacactgc agagtggggt gccatcaaga ttctccggat ctgggagtgg cactgacttc 2520
accctgacta ttagctccct gcagccagag gacttcgcca cctattactg cctgcaggat 2580
tataattacc cctggacatt tggacagggg actaaggtgg agatcaaacg gactgtcgcc 2640
gctcccagcg tgttcatttt tcctccatcc gacgaacagc tgaagagcgg aaccgcatcc 2700
gtggtgtgcc tgctgaacaa tttctatcct cgcgaagcaa aggtccagtg gaaagtggat 2760
aacgccctgc agagcggcaa ttcccaggag tctgtgactg aacaggacag taaggattca 2820
acctacagcc tgtctagtac cctgacactg tccaaagctg actatgagaa gcataaagtg 2880
tacgcatgtg aggtcaccca ccaggggctg tccagtccag tcaccaagtc tttcaatagg 2940
ggcgaatgc 2949

<210> SEQ ID NO 22
<211> LENGTH: 983
<212> TYPE: PRT
<213> ORGANISM: Artificial Sequence
<220> FEATURE:
<223> OTHER INFORMATION: amino acid sequence of pGX9259: Bispecific Pseudomonas (Bis4-V2L2MD/Psl0096)-YTE only pGX0001; DMAb-BiSPA

<400> SEQUENCE: 22

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Asn Trp Val Arg Gln Ala Pro Gly Lys Gly Leu Glu Trp Val
35 40 45

Ser Ala Ile Thr Met Ser Gly Ile Thr Ala Tyr Tyr Thr Asp Asp Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Lys Glu Glu Phe Leu Pro Gly Thr His Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Gly Ser Gly Gly Gly Gly Ser Gln Val Gln
225                 230                 235                 240

Leu Gln Glu Ser Gly Pro Gly Leu Val Lys Pro Ser Glu Thr Leu Ser
                245                 250                 255

Leu Thr Cys Thr Val Ser Gly Gly Ser Ile Ser Pro Tyr Tyr Trp Thr
            260                 265                 270

Trp Ile Arg Gln Pro Pro Gly Lys Cys Leu Glu Leu Ile Gly Tyr Ile
        275                 280                 285

His Ser Ser Gly Tyr Thr Asp Tyr Asn Pro Ser Leu Lys Ser Arg Val
    290                 295                 300

Thr Ile Ser Gly Asp Thr Ser Lys Lys Gln Phe Ser Leu Lys Leu Ser
305                 310                 315                 320

Ser Val Thr Ala Ala Asp Thr Ala Val Tyr Tyr Cys Ala Arg Ala Asp
                325                 330                 335

Trp Asp Arg Leu Arg Ala Leu Asp Ile Trp Gly Gln Gly Thr Met Val
            340                 345                 350

Thr Val Ser Ser Gly Gly Gly Gly Ser Gly Gly Gly Gly Ser Gly Gly
        355                 360                 365

Gly Gly Ser Gly Gly Gly Gly Ser Asp Ile Gln Leu Thr Gln Ser Pro
    370                 375                 380

Ser Ser Leu Ser Ala Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
                405                 410                 415

Gly Lys Ala Pro Lys Leu Leu Ile Tyr Gly Ala Ser Asn Leu Gln Ser
            420                 425                 430

Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460

Gln Gln Ser Thr Gly Ala Trp Asn Trp Phe Gly Cys Gly Thr Lys Val
465                 470                 475                 480

Glu Ile Lys Gly Gly Gly Gly Ser Gly Gly Gly Gly Ser Asp Lys Thr
                485                 490                 495

His Thr Cys Pro Pro Cys Pro Ala Pro Glu Leu Leu Gly Gly Pro Ser
            500                 505                 510
```

```
Val Phe Leu Phe Pro Pro Lys Pro Lys Asp Thr Leu Tyr Ile Thr Arg
        515                 520                 525

Glu Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

Arg Gly Arg Lys Arg Arg Ser Gly Ser Gly Ala Thr Asn Phe Ser Leu
                725                 730                 735

Leu Lys Gln Ala Gly Asp Val Glu Glu Asn Pro Gly Pro Met Val Leu
            740                 745                 750

Gln Thr Gln Val Phe Ile Ser Leu Leu Leu Trp Ile Ser Gly Ala Tyr
        755                 760                 765

Gly Ala Ile Gln Met Thr Gln Ser Pro Ser Ser Leu Ser Ala Ser Val
    770                 775                 780

Gly Asp Arg Val Thr Ile Thr Cys Arg Ala Ser Gln Gly Ile Arg Asn
785                 790                 795                 800

Asp Leu Gly Trp Tyr Gln Gln Lys Pro Gly Lys Ala Pro Lys Leu Leu
                805                 810                 815

Ile Tyr Ser Ala Ser Thr Leu Gln Ser Gly Val Pro Ser Arg Phe Ser
            820                 825                 830

Gly Ser Gly Ser Gly Thr Asp Phe Thr Leu Thr Ile Ser Ser Leu Gln
        835                 840                 845

Pro Glu Asp Phe Ala Thr Tyr Tyr Cys Leu Gln Asp Tyr Asn Tyr Pro
    850                 855                 860

Trp Thr Phe Gly Gln Gly Thr Lys Val Glu Ile Lys Arg Thr Val Ala
865                 870                 875                 880

Ala Pro Ser Val Phe Ile Phe Pro Pro Ser Asp Glu Gln Leu Lys Ser
                885                 890                 895

Gly Thr Ala Ser Val Val Cys Leu Leu Asn Asn Phe Tyr Pro Arg Glu
            900                 905                 910

Ala Lys Val Gln Trp Lys Val Asp Asn Ala Leu Gln Ser Gly Asn Ser
        915                 920                 925

Gln Glu Ser Val Thr Glu Gln Asp Ser Lys Asp Ser Thr Tyr Ser Leu
```

930 935 940

Ser Ser Thr Leu Thr Leu Ser Lys Ala Asp Tyr Glu Lys His Lys Val
945 950 955 960

Tyr Ala Cys Glu Val Thr His Gln Gly Leu Ser Ser Pro Val Thr Lys
965 970 975

Ser Phe Asn Arg Gly Glu Cys
980

<210> SEQ ID NO 23
<211> LENGTH: 7
<212> TYPE: PRT
<213> ORGANISM: Artificial Sequence
<220> FEATURE:
<223> OTHER INFORMATION: furin cleavage sequence

<400> SEQUENCE: 23

Arg Gly Arg Lys Arg Arg Ser
1 5

<210> SEQ ID NO 24
<211> LENGTH: 19
<212> TYPE: PRT
<213> ORGANISM: Artificial Sequence
<220> FEATURE:
<223> OTHER INFORMATION: signal peptide amino acid sequence

<400> SEQUENCE: 24

Met Asp Trp Thr Trp Arg Ile Leu Phe Leu Val Ala Ala Ala Thr Gly
1 5 10 15

Thr His Ala

<210> SEQ ID NO 25
<211> LENGTH: 20
<212> TYPE: PRT
<213> ORGANISM: Artificial Sequence
<220> FEATURE:
<223> OTHER INFORMATION: signal peptide amino acid sequence

<400> SEQUENCE: 25

Met Val Leu Gln Thr Gln Val Phe Ile Ser Leu Leu Leu Trp Ile Ser
1 5 10 15

Gly Ala Tyr Gly
20

<210> SEQ ID NO 26
<211> LENGTH: 1419
<212> TYPE: DNA
<213> ORGANISM: Artificial Sequence
<220> FEATURE:
<223> OTHER INFORMATION: nucleotide sequence of pGX9308: V2L2MD heavy
chain operably linked to a sequence encoding an IgE leader
sequence

<400> SEQUENCE: 26
atggactgga cctggagaat cctgttcctg gtggcagcag caaccggaac acacgcagag 60
gtgcagctgc tggagagcgg cggcggcctg gtgcagcctg gcggcagcct gaggctgtcc 120
tgcgcagcat ctggcttcac ctttagctcc tatgcaatga actgggtgcg ccaggcacca 180
ggcaagggac tggagtgggt gtctgccatc acaatgagcg gcatcaccgc ctactataca 240
gacgatgtga agggcaggtt taccatcagc agagacaact ccaagaatac actgtacctg 300
cagatgaata gcctgagagc cgaggatacc gccgtgtact attgcgccaa ggaggagttc 360

```
ctgcccggca cacactacta ttacggaatg gacgtgtggg gacagggaac cacagtgacc    420

gtgtctagcg cctccacaaa gggacctagc gtgttcccac tggcaccctc ctctaagtcc    480

acctctggcg gcacagccgc cctgggctgt ctggtgaagg attatttccc agagcccgtg    540

accgtgtctt ggaacagcgg cgccctgacc tctggagtgc acacatttcc agccgtgctg    600

cagagctccg gcctgtatag cctgtctagc gtggtgaccg tgccctcctc tagcctgggc    660

acccagacat acatctgcaa cgtgaatcac aagccatcta atacaaaggt ggacaagaag    720

gtggagccca agagctgtga taagacccac acatgccctc cctgtcctgc accagagctg    780

ctgggcggcc catccgtgtt cctgtttcca cccaagccta aggacaccct gatgatctcc    840

cggaccccag aggtgacatg cgtggtggtg gacgtgtctc acgaggaccc cgaggtgaag    900

ttcaactggt acgtggatgg cgtggaggtg cacaatgcca agaccaagcc acgggaggag    960

cagtataaca gcacctaccg cgtggtgtcc gtgctgacag tgctgcacca ggactggctg   1020

aacggcaagg agtacaagtg caaggtgagc aataaggccc tgcccgcccc tatcgagaag   1080

accatctcca aggccaaggg ccagcctagg gagccacagg tgtatacact gcctccaagc   1140

agagacgagc tgaccaagaa ccaggtgtcc ctgacatgtc tggtgaaggg cttctaccct   1200

tccgatatcg ccgtggagtg ggagtctaat ggccagccag agaacaatta taagaccaca   1260

ccccctgtgc tggactccga tggctctttc tttctgtact ctaagctgac cgtggataag   1320

agccgctggc agcagggcaa cgtgtttagc tgttccgtga tgcacgaggc cctgcacaat   1380

cactacacac agaagtctct gagcctgtcc cctggcaag                          1419
```

```
<210> SEQ ID NO 27
<211> LENGTH: 473
<212> TYPE: PRT
<213> ORGANISM: Artificial Sequence
<220> FEATURE:
<223> OTHER INFORMATION: amino acid sequence of pGX9308: V2L2MD heavy
      chain operably linked to an IgE leader sequence

<400> SEQUENCE: 27

Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Thr Met Ser Gly Ile Thr Ala Tyr Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175
```

```
Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470


<210> SEQ ID NO 28
<211> LENGTH: 702
<212> TYPE: DNA
<213> ORGANISM: Artificial Sequence
<220> FEATURE:
<223> OTHER INFORMATION: nucleotide sequence of pGX9309: V2L2MD light
      chain operably linked to a sequence encoding an IgE leader
      sequence

<400> SEQUENCE: 28

atggtgctgc agacacaggt gttcatcagc ctgctgctgt ggatctccgg agcatacgga     60

gcaatccaga tgacccagtc cccaagctcc ctgagcgcct ccgtgggcga cagggtgacc    120

atcacatgca gagcctctca gggcatccgg aacgatctgg gctggtacca gcagaagcca    180

ggcaaggccc ccaagctgct gatctattct gccagcaccc tgcagtctgg agtgcccagc    240

cggttctccg gctctggcag cggaacagac tttaccctga caatctctag cctgcagcct    300
```

```
gaggacttcg ccacctacta ttgcctgcag gattacaatt atccatggac ctttggccag    360

ggcacaaagg tggagatcaa gcgcacagtg gccgcccccca gcgtgttcat ctttcccccct    420

agcgacgagc agctgaagtc cggcaccgcc tctgtggtgt gcctgctgaa caatttctac    480

cctagggagg ccaaggtgca gtggaaggtg gataacgccc tgcagagcgg caattcccag    540

gagtctgtga ccgagcagga cagcaaggat tccacatatt ccctgtctaa caccctgaca    600

ctgagcaagg ccgattacga gaagcacaag gtgtatgcat gcgaggtgac ccaccaggga    660

ctgtcctctc ccgtgacaaa gtcctttaat aggggcgagt gt                        702
```

<210> SEQ ID NO 29
<211> LENGTH: 234
<212> TYPE: PRT
<213> ORGANISM: Artificial Sequence
<220> FEATURE:
<223> OTHER INFORMATION: amino acid sequence of pGX9309: V2L2MD light chain operably linked to an IgE leader sequence

<400> SEQUENCE: 29

```
Met Val Leu Gln Thr Gln Val Phe Ile Ser Leu Leu Leu Trp Ile Ser
1               5                   10                  15

Gly Ala Tyr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Arg Asn Asp Leu Gly Trp Tyr Gln Gln Lys Pro Gly Lys Ala Pro
    50                  55                  60

Lys Leu Leu Ile Tyr Ser Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Asn Tyr Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Asn Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 30
<211> LENGTH: 2208
<212> TYPE: DNA
<213> ORGANISM: Artificial Sequence
<220> FEATURE:
<223> OTHER INFORMATION: nucleotide sequence of pGX9214: Pseudo-V2L2MD; DMAb-?PcrV operably linked to a sequence encoding an IgE leader sequence

<400> SEQUENCE: 30
atggattgga catggaggat tctgtttctg gtcgccgccg ctactggaac ccacgccgag 60
gtgcagctgc tggagtcagg aggaggactg gtgcagcccg gcggatcact gcgactgagc 120
tgcgcagctt ccggcttcac cttcagcagc tatgccatga actgggtccg acaggctcct 180
ggcaagggac tggaatgggt gagtgcaatc accatgtcag ggattactgc ctactatacc 240
gacgatgtga aaggccgatt cactatctct agggacaaca gtaagaatac cctgtacctg 300
cagatgaatt ccctgcgcgc tgaggataca gcagtgtact attgcgccaa ggaggaattc 360
ctgccaggga ctcactacta ttacggaatg gacgtgtggg gacagggaac cacagtcacc 420
gtgtctagtg caagcacaaa aggcccctcc gtgtttcccc tggccccttc aagcaagtct 480
acaagtgggg gcactgcagc cctgggatgt ctggtgaagg attacttccc tgagccagtc 540
accgtgagct ggaactccgg cgccctgact tccggagtcc atacctttcc tgctgtgctg 600
cagtcctctg gcctgtatag cctgagttca gtggtcaccg tcccaagctc ctctctggga 660
acacagactt acatctgcaa cgtgaatcac aaaccaagca atacaaaggt cgacaagaaa 720
gtggaaccca aatcctgtga taagacccat acatgccctc cctgtccagc acctgagctg 780
ctgggagggc caagcgtgtt cctgtttcca cccaagccta aagacacact gatgatttct 840
cggacccccg aagtcacatg cgtggtcgtg gacgtgagcc acgaggaccc cgaagtcaag 900
tttaactggt acgtggatgg cgtcgaggtg cataatgcca agaccaaacc acgagaggaa 960
cagtataact ctacatacag ggtcgtgagt gtcctgactg tgctgcacca ggactggctg 1020
aacgggaagg agtacaagtg caaagtgtcc aacaaggccc tgccagctcc catcgagaag 1080
accatttcta aggccaaagg ccagccaaga gaaccccagg tgtatacact gcctccaagt 1140
cgggacgagc tgactaaaaa ccaggtctct ctgacctgtc tggtgaaggg attctaccct 1200
tccgatatcg ctgtggagtg ggaatctaat gggcagccag aaaacaatta taagactacc 1260
cctcccgtgc tggactctga tggaagtttc tttctgtact ccaaactgac cgtggacaag 1320
tctagatggc agcaggggaa cgtcttttca tgcagcgtga tgcatgaggc cctgcacaat 1380
cattacactc agaaatccct gtctctgagt cctgggaaac ggggccgcaa gaggagatca 1440
ggaagcgggg ccaccaactt ctccctgctg aagcaggctg gcgatgtgga ggaaaatcct 1500
ggaccaatgg tcctgcagac tcaggtgttt atctcactgc tgctgtggat tagcggagca 1560
tacggggcca ttcagatgac ccagtccccc agttcactgt ccgcttctgt cggcgacaga 1620
gtgactatca cctgtcgggc aagccaggga attcgcaacg atctggggtg gtatcagcag 1680
aagcctggga aagctccaaa gctgctgatc tacagtgcat caactctgca gtcaggagtg 1740
cctagccggt tcagcggctc cggatctgga accgacttta cactgactat tagctccctg 1800
cagccagagg acttcgccac atattactgc ctgcaggatt ataattaccc ctggacattt 1860
ggccagggaa ctaaagtgga aatcaagcgc acagtcgctg cacctagcgt gttcatcttt 1920
ccaccctcag acgagcagct gaagtccgga actgcttctg tggtgtgcct gctgaacaat 1980
ttctatccaa gggaagcaaa agtccagtgg aaggtggata acgccctgca gtcaggcaat 2040
agccaggagt ccgtgaccga acaggactct aaagatagta catacagtct gtcaaacacc 2100
ctgacactga gcaaggctga ttatgagaag cacaaagtgt acgcatgcga agtcacccac 2160
caggggctgt cctcaccagt cacaaaatct ttcaatcggg gagaatgc 2208

<210> SEQ ID NO 31
<211> LENGTH: 736
<212> TYPE: PRT
<213> ORGANISM: Artificial Sequence
<220> FEATURE:
<223> OTHER INFORMATION: amino acid sequence of pGX9214: Pseudo-V2L2MD; DMAb-?PcrV operably linked to an IgE leader sequence

<400> SEQUENCE: 31

```
Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Thr Met Ser Gly Ile Thr Ala Tyr Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365
```

```
Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Val Leu Gln Thr Gln Val Phe Ile Ser
            500                 505                 510

Leu Leu Leu Trp Ile Ser Gly Ala Tyr Gly Ala Ile Gln Met Thr Gln
        515                 520                 525

Ser Pro Ser Ser Leu Ser Ala Ser Val Gly Asp Arg Val Thr Ile Thr
    530                 535                 540

Cys Arg Ala Ser Gln Gly Ile Arg Asn Asp Leu Gly Trp Tyr Gln Gln
545                 550                 555                 560

Lys Pro Gly Lys Ala Pro Lys Leu Leu Ile Tyr Ser Ala Ser Thr Leu
                565                 570                 575

Gln Ser Gly Val Pro Ser Arg Phe Ser Gly Ser Gly Ser Gly Thr Asp
            580                 585                 590

Phe Thr Leu Thr Ile Ser Ser Leu Gln Pro Glu Asp Phe Ala Thr Tyr
        595                 600                 605

Tyr Cys Leu Gln Asp Tyr Asn Tyr Pro Trp Thr Phe Gly Gln Gly Thr
    610                 615                 620

Lys Val Glu Ile Lys Arg Thr Val Ala Ala Pro Ser Val Phe Ile Phe
625                 630                 635                 640

Pro Pro Ser Asp Glu Gln Leu Lys Ser Gly Thr Ala Ser Val Val Cys
                645                 650                 655

Leu Leu Asn Asn Phe Tyr Pro Arg Glu Ala Lys Val Gln Trp Lys Val
            660                 665                 670

Asp Asn Ala Leu Gln Ser Gly Asn Ser Gln Glu Ser Val Thr Glu Gln
        675                 680                 685

Asp Ser Lys Asp Ser Thr Tyr Ser Leu Ser Asn Thr Leu Thr Leu Ser
    690                 695                 700

Lys Ala Asp Tyr Glu Lys His Lys Val Tyr Ala Cys Glu Val Thr His
705                 710                 715                 720

Gln Gly Leu Ser Ser Pro Val Thr Lys Ser Phe Asn Arg Gly Glu Cys
                725                 730                 735
```

<210> SEQ ID NO 32
<211> LENGTH: 2217
<212> TYPE: DNA
<213> ORGANISM: Artificial Sequence
<220> FEATURE:
<223> OTHER INFORMATION: nucleotide sequence of pGX9247: V2L2 with Rhesus Fc in pGX0001; DMAb-?PcrV operably linked to a sequence encoding an IgE leader sequence

<400> SEQUENCE: 32
atggactgga catggagaat cctgttcctg gtcgccgccg ctactgggac tcacgccgag 60
gtgcagctcc tggaaagtgg gggagggctg gtgcagcccg gcgggtccct cagactgtct 120
tgcgccgcta gtggcttcac ctttagctcc tatgcaatga actgggtgcg gcaggcacct 180
gggaaaggac tggagtgggt gagcgccatc accatgtccg gcattactgc atactatacc 240
gacgatgtga aagggaggtt cacaatctca agagacaaca gcaagaatac tctctacctg 300
cagatgaata gcctgcgcgc tgaggatact gcagtgtact attgcgccaa ggaggaattc 360
ctgccaggca cccactacta ttacggaatg gacgtgtggg gacagggaac cacagtcacc 420
gtgtctagtg cttctacaaa agggcccagc gtgttcccac tggcaccctc aagcaggagt 480
acatcagaga gcactgcagc cctcggatgt ctggtgaagg attacttccc cgaacctgtc 540
accgtgtcct ggaactccgg atctctcact tctggcgtcc acacctttcc cgccgtgctg 600
cagtcctctg ggctctatag cctgagttca gtggtcaccg tgcctagctc ctctctggga 660
acacagactt acgtctgcaa cgtgaatcat aagccatcca atacaaaggt cgacaaaaga 720
gtggagatca aaacctgtgg aggcgggtct aagcccccta catgcccacc ctgtccagca 780
ccagaactgc tcggaggccc aagcgtgttc ctctttcctc caaagcccaa agacaccctg 840
atgatttccc ggaccccaga ggtcacatgc gtggtcgtgg acgtgagcca ggaagaccct 900
gatgtcaaat tcaactggta cgtgaatggc gccgaggtgc accatgctca gacaaagccc 960
agagaaactc agtataactc aacctaccgg gtcgtgagcg tcctcaccgt gacacaccag 1020
gactggctga acggcaaaga gtatacatgc aaagtgagca ataaggccct gcctgctcca 1080
atccagaaga ctattagcaa ggataaaggg cagcctcgcg aaccacaggt gtacaccctg 1140
cctcccagca gggaggaact gactaaaaac caggtcagcc tcacctgtct ggtgaagggc 1200
ttctaccctt ccgacatcgt cgtggagtgg gaaagttcag gccagccaga gaatacctac 1260
aagactaccc cacccgtgct ggactctgat ggaagttatt tcctctacag caaactgaca 1320
gtggataagt ccagatggca gcagggcaac gtctttagtt gctcagtgat gcatgaggcc 1380
ctccacaatc attacacaca gaaaagcctg tccgtgtctc cccggggcag gaagaggaga 1440
agtggatcag gcgcaactaa cttcagcctg ctcaagcagg caggggacgt ggaggaaaat 1500
cccggaccta tggtcctgca gacccaggtg tttatctccc tgctcctgtg gatttctggc 1560
gcatacgggg ccatccagat gacacagagc cccagctccc tgagcgcctc cgtcggcgac 1620
cgggtgacta tcacctgtcg cgctagccag ggaattagga acgatctggg ctggtatcag 1680
cagaagcccg gcaaagcccc taagctcctg atctactctg ctagtacact gcagtccggg 1740
gtgccttcta ggttctcagg gagcggcagc ggcactgact tcaccctcac tatttctagt 1800
ctgcagccag aggacttcgc aacctattac tgcctgcagg attataatta cccctggaca 1860
tttgggcagg gaactaaagt ggagatcaag cgcgctgtcg ctgcacctag cgtgttcatc 1920
tttcctccaa gtgaagacca ggtcaagagt ggcaccgtgt cagtggtgtg cctcctgaac 1980
aatttctatc caagggaggc ctccgtgaag tggaaagtcg atggggtgct gaaaacagga 2040
aactcacagg agagcgtgac tgaacaggac agtaaggata atacctactc actgtcaagc 2100
accctcacac tgtcctctac cgactatcag tctcacaacg tgtacgcttg cgaagtcacc 2160
caccaggggc tcagtagtcc agtcacaaaa tctttcaata gaggcgaatg ttgataa 2217

<210> SEQ ID NO 33
<211> LENGTH: 737

<212> TYPE: PRT
<213> ORGANISM: Artificial Sequence
<220> FEATURE:
<223> OTHER INFORMATION: amino acid sequence of pGX9247: V2L2 with
Rhesus Fc in pGX0001; DMAb-?PcrV operably linked to an IgE leader
sequence

<400> SEQUENCE: 33

Met Asp Trp Thr Trp Arg Ile Leu Phe Leu Val Ala Ala Ala Thr Gly
1 5 10 15

Thr His Ala Glu Val Gln Leu Leu Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Ala Met Asn Trp Val Arg Gln Ala Pro Gly Lys Gly Leu
50 55 60

Glu Trp Val Ser Ala Ile Thr Met Ser Gly Ile Thr Ala Tyr Tyr Thr
65 70 75 80

Asp Asp Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Lys Glu Glu Phe Leu Pro Gly Thr His Tyr Tyr Tyr
115 120 125

Gly Met Asp Val Trp Gly Gln Gly Thr Thr Val Thr Val Ser Ser Ala
130 135 140

Ser Thr Lys Gly Pro Ser Val Phe Pro Leu Ala Pro Ser Ser Arg Ser
145 150 155 160

Thr Ser Glu Ser Thr Ala Ala Leu Gly Cys Leu Val Lys Asp Tyr Phe
165 170 175

Pro Glu Pro Val Thr Val Ser Trp Asn Ser Gly Ser Leu Thr Ser Gly
180 185 190

Val His Thr Phe Pro Ala Val Leu Gln Ser Ser Gly Leu Tyr Ser Leu
195 200 205

Ser Ser Val Val Thr Val Pro Ser Ser Ser Leu Gly Thr Gln Thr Tyr
210 215 220

Val Cys Asn Val Asn His Lys Pro Ser Asn Thr Lys Val Asp Lys Arg
225 230 235 240

Val Glu Ile Lys Thr Cys Gly Gly Gly Ser Lys Pro Pro Thr Cys Pro
245 250 255

Pro Cys Pro Ala Pro Glu Leu Leu Gly Gly Pro Ser Val Phe Leu Phe
260 265 270

Pro Pro Lys Pro Lys Asp Thr Leu Met Ile Ser Arg Thr Pro Glu Val
275 280 285

Thr Cys Val Val Val Asp Val Ser Gln Glu Asp Pro Asp Val Lys Phe
290 295 300

Asn Trp Tyr Val Asn Gly Ala Glu Val His His Ala Gln Thr Lys Pro
305 310 315 320

Arg Glu Thr Gln Tyr Asn Ser Thr Tyr Arg Val Val Ser Val Leu Thr
325 330 335

Val Thr His Gln Asp Trp Leu Asn Gly Lys Glu Tyr Thr Cys Lys Val
340 345 350

Ser Asn Lys Ala Leu Pro Ala Pro Ile Gln Lys Thr Ile Ser Lys Asp
355 360 365

Lys Gly Gln Pro Arg Glu Pro Gln Val Tyr Thr Leu Pro Pro Ser Arg

```
    370                 375                 380

Glu Glu Leu Thr Lys Asn Gln Val Ser Leu Thr Cys Leu Val Lys Gly
385                 390                 395                 400

Phe Tyr Pro Ser Asp Ile Val Val Glu Trp Glu Ser Ser Gly Gln Pro
                405                 410                 415

Glu Asn Thr Tyr Lys Thr Thr Pro Pro Val Leu Asp Ser Asp Gly Ser
            420                 425                 430

Tyr Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Val Ser Pro Arg Gly Arg Lys Arg Arg
465                 470                 475                 480

Ser Gly Ser Gly Ala Thr Asn Phe Ser Leu Leu Lys Gln Ala Gly Asp
                485                 490                 495

Val Glu Glu Asn Pro Gly Pro Met Val Leu Gln Thr Gln Val Phe Ile
            500                 505                 510

Ser Leu Leu Leu Trp Ile Ser Gly Ala Tyr Gly Ala Ile Gln Met Thr
        515                 520                 525

Gln Ser Pro Ser Ser Leu Ser Ala Ser Val Gly Asp Arg Val Thr Ile
    530                 535                 540

Thr Cys Arg Ala Ser Gln Gly Ile Arg Asn Asp Leu Gly Trp Tyr Gln
545                 550                 555                 560

Gln Lys Pro Gly Lys Ala Pro Lys Leu Leu Ile Tyr Ser Ala Ser Thr
                565                 570                 575

Leu Gln Ser Gly Val Pro Ser Arg Phe Ser Gly Ser Gly Ser Gly Thr
            580                 585                 590

Asp Phe Thr Leu Thr Ile Ser Ser Leu Gln Pro Glu Asp Phe Ala Thr
        595                 600                 605

Tyr Tyr Cys Leu Gln Asp Tyr Asn Tyr Pro Trp Thr Phe Gly Gln Gly
    610                 615                 620

Thr Lys Val Glu Ile Lys Arg Ala Val Ala Ala Pro Ser Val Phe Ile
625                 630                 635                 640

Phe Pro Pro Ser Glu Asp Gln Val Lys Ser Gly Thr Val Ser Val Val
                645                 650                 655

Cys Leu Leu Asn Asn Phe Tyr Pro Arg Glu Ala Ser Val Lys Trp Lys
            660                 665                 670

Val Asp Gly Val Leu Lys Thr Gly Asn Ser Gln Glu Ser Val Thr Glu
        675                 680                 685

Gln Asp Ser Lys Asp Asn Thr Tyr Ser Leu Ser Ser Thr Leu Thr Leu
    690                 695                 700

Ser Ser Thr Asp Tyr Gln Ser His Asn Val Tyr Ala Cys Glu Val Thr
705                 710                 715                 720

His Gln Gly Leu Ser Ser Pro Val Thr Lys Ser Phe Asn Arg Gly Glu
                725                 730                 735

Cys
```

<210> SEQ ID NO 34
<211> LENGTH: 2184
<212> TYPE: DNA
<213> ORGANISM: Artificial Sequence
<220> FEATURE:
<223> OTHER INFORMATION: nucleotide sequence of pGX9248: Pseudo-V2L2MD rbFc; DMAb-?PcrV operably linked to a sequence encoding an IgE leader sequence

<400> SEQUENCE: 34

```
atggactgga catggagaat cctgtttctg gtcgccgccg ccaccggaac ccacgccgaa     60
gtgcagctgc tggaatctgg agggggcctg gtgcagcccg gcggcagcct gaggctgtcc    120
tgcgccgcca gcggcttcac cttctccagc tacgccatga actgggtgcg ccaggcccca    180
ggcaagggac tggagtgggt gtccgccatc accatgagcg gcatcaccgc ctactacacc    240
gacgacgtga agggccgctt caccatctcc cgggacaaca gcaagaacac cctgtacctg    300
cagatgaact ccctgagggc cgaggacacc gccgtgtact actgcgccaa ggaggagttc    360
ctgccaggaa cccactacta ctacggaatg gacgtgtggg gacagggaac caccgtgacc    420
gtgtccagcg gccagcccaa ggcccccagc gtgttcccac tggccccatg ctgcggcgac    480
accccctcca gcaccgtgac cctgggatgc ctggtgaagg gatacctgcc agagccagtg    540
accgtgacct ggaactccgg caccctgacc aacggcgtga ggaccttccc aagcgtgcgc    600
cagtccagcg gactgtactc cctgtccagc gtggtgagcg tgacctccag ctcccagcca    660
gtgacctgca acgtggccca cccagccacc aacaccaagg tggacaagac cgtggcccca    720
agcacctgct ccaagccaac ctgccctcct cccgagctgc tgggcggccc ctccgtgttc    780
atcttccctc ccaagcccaa ggacaccctg atgatctcca ggaccccaga ggtgacctgc    840
gtggtggtgg acgtgagcca ggacgacccc gaggtgcagt tcacctggta catcaacaac    900
gagcaggtgc ggaccgcccg ccctccccctg cgcgagcagc agttcaactc caccatccgg    960
gtggtgagca ccctgccaat cacccaccag gactggctga ggggcaagga gttcaagtgc   1020
aaggtgcaca acaaggccct gcccgccccc atcgagaaga ccatcagcaa ggccaggggc   1080
cagccactgg agcccaaggt gtacaccatg ggccctcccc gcgaggagct gagctccagg   1140
agcgtgtccc tgacctgcat gatcaacggc ttctacccca gcgacatctc cgtggagtgg   1200
gagaagaacg gcaaggccga ggacaactac aagaccaccc cagccgtgct ggacagcgac   1260
ggctcctact tcctgtacaa caagctgtcc gtgcccacca gcgagtggca gcggggcgac   1320
gtgttcacct gctccgtgat gcacgaggcc ctgcacaacc actacaccca gaagagcatc   1380
tccaggagcc ccggcaagag gggaaggaag cgccggtccg gcagcggagc caccaacttc   1440
agcctgctga agcaggccgg cgacgtggag gagaacccag gaccaatggt gctgcagacc   1500
caggtgttca tctccctgct gctgtggatc agcggagcct acggagccat ccagatgacc   1560
cagtccccca gctccctgtc cgccagcgtg ggcgacaggg tgaccatcac ctgcagggcc   1620
agccagggca tcaggaacga cctgggctgg taccagcaga agcccggcaa ggcccccaag   1680
ctgctgatct actccgccag caccctgcag tccggagtgc ccagccggtt ctccggcagc   1740
ggctccggaa ccgacttcac cctgaccatc agctccctgc agcccgagga cttcgccacc   1800
tactactgcc tgcaggacta caactacccc tggaccttcg gccagggcac caaggtggag   1860
atcaagaggc agccagccgt gaccccatcc gtgatcctgt tccctccctc ctccgaggag   1920
ctgaaggaca acaaggccac cctggtgtgc ctgatctccg acttctaccc ccgcaccgtg   1980
aaggtgaact ggaaggccga cggaaacagc gtgacccagg gagtggacac cacccagcca   2040
agcaagcagt ccaacaacaa gtacgccgcc agctccttcc tgcacctgac cgccaaccag   2100
tggaagagct accagtccgt gacctgtcag gtcacccacg aagggcacac cgtcgaaaaa   2160
tctctggccc ccgccgaatg ttct                                          2184
```

<210> SEQ ID NO 35

```
<211> LENGTH: 728
<212> TYPE: PRT
<213> ORGANISM: Artificial Sequence
<220> FEATURE:
<223> OTHER INFORMATION: amino acid sequence of pGX9248: Pseudo-V2L2MD
      rbFc; DMAb-?PcrV operably linked to an IgE leader sequence

<400> SEQUENCE: 35

Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Thr Met Ser Gly Ile Thr Ala Tyr Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125

Gly Met Asp Val Trp Gly Gln Gly Thr Thr Val Thr Val Ser Ser Gly
    130                 135                 140

Gln Pro Lys Ala Pro Ser Val Phe Pro Leu Ala Pro Cys Cys Gly Asp
145                 150                 155                 160

Thr Pro Ser Ser Thr Val Thr Leu Gly Cys Leu Val Lys Gly Tyr Leu
                165                 170                 175

Pro Glu Pro Val Thr Val Thr Trp Asn Ser Gly Thr Leu Thr Asn Gly
            180                 185                 190

Val Arg Thr Phe Pro Ser Val Arg Gln Ser Ser Gly Leu Tyr Ser Leu
        195                 200                 205

Ser Ser Val Val Ser Val Thr Ser Ser Ser Gln Pro Val Thr Cys Asn
    210                 215                 220

Val Ala His Pro Ala Thr Asn Thr Lys Val Asp Lys Thr Val Ala Pro
225                 230                 235                 240

Ser Thr Cys Ser Lys Pro Thr Cys Pro Pro Pro Glu Leu Leu Gly Gly
                245                 250                 255

Pro Ser Val Phe Ile Phe Pro Pro Lys Pro Lys Asp Thr Leu Met Ile
            260                 265                 270

Ser Arg Thr Pro Glu Val Thr Cys Val Val Val Asp Val Ser Gln Asp
        275                 280                 285

Asp Pro Glu Val Gln Phe Thr Trp Tyr Ile Asn Asn Glu Gln Val Arg
    290                 295                 300

Thr Ala Arg Pro Pro Leu Arg Glu Gln Gln Phe Asn Ser Thr Ile Arg
305                 310                 315                 320

Val Val Ser Thr Leu Pro Ile Thr His Gln Asp Trp Leu Arg Gly Lys
                325                 330                 335

Glu Phe Lys Cys Lys Val His Asn Lys Ala Leu Pro Ala Pro Ile Glu
            340                 345                 350

Lys Thr Ile Ser Lys Ala Arg Gly Gln Pro Leu Glu Pro Lys Val Tyr
        355                 360                 365

Thr Met Gly Pro Pro Arg Glu Glu Leu Ser Ser Arg Ser Val Ser Leu
```

```
    370                 375                 380

Thr Cys Met Ile Asn Gly Phe Tyr Pro Ser Asp Ile Ser Val Glu Trp
385                 390                 395                 400

Glu Lys Asn Gly Lys Ala Glu Asp Asn Tyr Lys Thr Thr Pro Ala Val
                405                 410                 415

Leu Asp Ser Asp Gly Ser Tyr Phe Leu Tyr Asn Lys Leu Ser Val Pro
            420                 425                 430

Thr Ser Glu Trp Gln Arg Gly Asp Val Phe Thr Cys Ser Val Met His
        435                 440                 445

Glu Ala Leu His Asn His Tyr Thr Gln Lys Ser Ile Ser Arg Ser Pro
    450                 455                 460

Gly Lys Arg Gly Arg Lys Arg Arg Ser Gly Ser Gly Ala Thr Asn Phe
465                 470                 475                 480

Ser Leu Leu Lys Gln Ala Gly Asp Val Glu Glu Asn Pro Gly Pro Met
                485                 490                 495

Val Leu Gln Thr Gln Val Phe Ile Ser Leu Leu Leu Trp Ile Ser Gly
            500                 505                 510

Ala Tyr Gly Ala Ile Gln Met Thr Gln Ser Pro Ser Ser Leu Ser Ala
        515                 520                 525

Ser Val Gly Asp Arg Val Thr Ile Thr Cys Arg Ala Ser Gln Gly Ile
    530                 535                 540

Arg Asn Asp Leu Gly Trp Tyr Gln Gln Lys Pro Gly Lys Ala Pro Lys
545                 550                 555                 560

Leu Leu Ile Tyr Ser Ala Ser Thr Leu Gln Ser Gly Val Pro Ser Arg
                565                 570                 575

Phe Ser Gly Ser Gly Ser Gly Thr Asp Phe Thr Leu Thr Ile Ser Ser
            580                 585                 590

Leu Gln Pro Glu Asp Phe Ala Thr Tyr Tyr Cys Leu Gln Asp Tyr Asn
        595                 600                 605

Tyr Pro Trp Thr Phe Gly Gln Gly Thr Lys Val Glu Ile Lys Arg Gln
    610                 615                 620

Pro Ala Val Thr Pro Ser Val Ile Leu Phe Pro Pro Ser Ser Glu Glu
625                 630                 635                 640

Leu Lys Asp Asn Lys Ala Thr Leu Val Cys Leu Ile Ser Asp Phe Tyr
                645                 650                 655

Pro Arg Thr Val Lys Val Asn Trp Lys Ala Asp Gly Asn Ser Val Thr
            660                 665                 670

Gln Gly Val Asp Thr Thr Gln Pro Ser Lys Gln Ser Asn Asn Lys Tyr
        675                 680                 685

Ala Ala Ser Ser Phe Leu His Leu Thr Ala Asn Gln Trp Lys Ser Tyr
    690                 695                 700

Gln Ser Val Thr Cys Gln Val Thr His Glu Gly His Thr Val Glu Lys
705                 710                 715                 720

Ser Leu Ala Pro Ala Glu Cys Ser
                725


<210> SEQ ID NO 36
<211> LENGTH: 1419
<212> TYPE: DNA
<213> ORGANISM: Artificial Sequence
<220> FEATURE:
<223> OTHER INFORMATION: nucleotide sequence of pGX9257 heavy chain:
      Pseudo-V2L2MD in pGX0003 (sCMV-light chain, hCMV-heavy chain);
      DMAb-?PcrV operably linked to a sequence encoding an IgE leader
      sequence
```

<400> SEQUENCE: 36
atggattgga catggaggat tctgtttctg gtcgccgccg ctactggaac ccacgccgag 60
gtgcagctgc tggagtcagg aggaggactg gtgcagcccg gcggatcact gcgactgagc 120
tgcgcagctt ccggcttcac cttcagcagc tatgccatga actgggtccg acaggctcct 180
ggcaagggac tggaatgggt gagtgcaatc accatgtcag ggattactgc ctactatacc 240
gacgatgtga aaggccgatt cactatctct agggacaaca gtaagaatac cctgtacctg 300
cagatgaatt ccctgcgcgc tgaggataca gcagtgtact attgcgccaa ggaggaattc 360
ctgccaggga ctcactacta ttacggaatg gacgtgtggg gacagggaac cacagtcacc 420
gtgtctagtg caagcacaaa aggcccctcc gtgtttcccc tggccccttc aagcaagtct 480
acaagtgggg gcactgcagc cctgggatgt ctggtgaagg attacttccc tgagccagtc 540
accgtgagct ggaactccgg cgccctgact tccggagtcc atacctttcc tgctgtgctg 600
cagtcctctg gcctgtatag cctgagttca gtggtcaccg tcccaagctc ctctctggga 660
acacagactt acatctgcaa cgtgaatcac aaaccaagca atacaaaggt cgacaagaaa 720
gtggaaccca aatcctgtga taagacccat acatgccctc cctgtccagc acctgagctg 780
ctgggagggc caagcgtgtt cctgtttcca cccaagccta aagacacact gatgatttct 840
cggacccccg aagtcacatg cgtggtcgtg gacgtgagcc acgaggaccc cgaagtcaag 900
tttaactggt acgtggatgg cgtcgaggtg cataatgcca agaccaaacc acgagaggaa 960
cagtataact ctacatacag ggtcgtgagt gtcctgactg tgctgcacca ggactggctg 1020
aacgggaagg agtacaagtg caaagtgtcc aacaaggccc tgccagctcc catcgagaag 1080
accatttcta aggccaaagg ccagccaaga gaaccccagg tgtatacact gcctccaagt 1140
cgggacgagc tgactaaaaa ccaggtctct ctgacctgtc tggtgaaggg attctaccct 1200
tccgatatcg ctgtggagtg ggaatctaat gggcagccag aaaacaatta taagactacc 1260
cctcccgtgc tggactctga tggaagtttc tttctgtact ccaaactgac cgtggacaag 1320
tctagatggc agcaggggaa cgtcttttca tgcagcgtga tgcatgaggc cctgcacaat 1380
cattacactc agaaatccct gtctctgagt cctgggaaa 1419

<210> SEQ ID NO 37
<211> LENGTH: 473
<212> TYPE: PRT
<213> ORGANISM: Artificial Sequence
<220> FEATURE:
<223> OTHER INFORMATION: amino acid sequence of pGX9257 heavy chain: Pseudo-V2L2MD in pGX0003 (sCMV-light chain, hCMV-heavy chain); DMAb-?PcrV operably linked to an IgE leader sequence

<400> SEQUENCE: 37

Met Asp Trp Thr Trp Arg Ile Leu Phe Leu Val Ala Ala Ala Thr Gly
1 5 10 15

Thr His Ala Glu Val Gln Leu Leu Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Ala Met Asn Trp Val Arg Gln Ala Pro Gly Lys Gly Leu
50 55 60

Glu Trp Val Ser Ala Ile Thr Met Ser Gly Ile Thr Ala Tyr Tyr Thr
65 70 75 80

Asp Asp Val Lys Gly Arg Phe Thr Ile Ser Arg Asp Asn Ser Lys Asn
85 90 95

```
Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 38
<211> LENGTH: 2208
<212> TYPE: DNA
<213> ORGANISM: Artificial Sequence
<220> FEATURE:

<223> OTHER INFORMATION: nucleotide sequence of pGX9258: Psuedo-V2L2MD-
      YTE only in pGX0001; DMAb-?PcrV operably linked to a sequence
      encoding an IgE leader sequence

<400> SEQUENCE: 38

```
atggattgga catggaggat tctgtttctg gtcgccgccg ctactggaac ccacgccgag      60
gtgcagctgc tggagtcagg aggaggactg gtgcagcccg gcggatcact gcgactgagc     120
tgcgcagctt ccggcttcac cttcagcagc tatgccatga actgggtccg acaggctcct     180
ggcaagggac tggaatgggt gagtgcaatc accatgtcag ggattactgc ctactatacc     240
gacgatgtga aaggccgatt cactatctct agggacaaca gtaagaatac cctgtacctg     300
cagatgaatt ccctgcgcgc tgaggataca gcagtgtact attgcgccaa ggaggaattc     360
ctgccaggga ctcactacta ttacggaatg gacgtgtggg gacagggaac cacagtcacc     420
gtgtctagtg caagcacaaa aggcccctcc gtgtttcccc tggccccttc aagcaagtct     480
acaagtgggg gcactgcagc cctgggatgt ctggtgaagg attacttccc tgagccagtc     540
accgtgagct ggaactccgg cgccctgact tccggagtcc atacctttcc tgctgtgctg     600
cagtcctctg gcctgtatag cctgagttca gtggtcaccg tcccaagctc ctctctggga     660
acacagactt acatctgcaa cgtgaatcac aaaccaagca atacaaaggt cgacaagaaa     720
gtggaaccca aatcctgtga taagacccat acatgccctc cctgtccagc acctgagctg     780
ctgggagggc caagcgtgtt cctgtttcca cccaagccta aagacacact gtacattact     840
cgggagcccg aagtcacatg cgtggtcgtg gacgtgagcc acgaggaccc cgaagtcaag     900
tttaactggt acgtggatgg cgtcgaggtg cataatgcca agaccaaacc acgagaggaa     960
cagtataact ctacatacag ggtcgtgagt gtcctgactg tgctgcacca ggactggctg    1020
aacgggaagg agtacaagtg caaagtgtcc aacaaggccc tgccagctcc catcgagaag    1080
accatttcta aggccaaagg ccagccaaga gaaccccagg tgtatacact gcctccaagt    1140
cgggacgagc tgactaaaaa ccaggtctct ctgacctgtc tggtgaaggg attctaccct    1200
tccgatatcg ctgtggagtg ggaatctaat gggcagccag aaaacaatta taagactacc    1260
cctcccgtgc tggactctga tggaagtttc tttctgtact ccaaactgac cgtggacaag    1320
tctagatggc agcaggggaa cgtcttttca tgcagcgtga tgcatgaggc cctgcacaat    1380
cattacactc agaaatccct gtctctgagt cctgggaaac ggggccgcaa gaggagatca    1440
ggaagcgggg ccaccaactt ctccctgctg aagcaggctg gcgatgtgga ggaaaatcct    1500
ggaccaatgg tcctgcagac tcaggtgttt atctcactgc tgctgtggat tagcggagca    1560
tacggggcca ttcagatgac ccagtccccc agttcactgt ccgcttctgt cggcgacaga    1620
gtgactatca cctgtcgggc aagccaggga attcgcaacg atctggggtg gtatcagcag    1680
aagcctggga aagctccaaa gctgctgatc tacagtgcat caactctgca gtcaggagtg    1740
cctagccggt tcagcggctc cggatctgga accgacttta cactgactat tagctccctg    1800
cagccagagg acttcgccac atattactgc ctgcaggatt ataattaccc ctggacattt    1860
ggccagggaa ctaaagtgga aatcaagcgc acagtcgctg cacctagcgt gttcatcttt    1920
ccaccctcag acgagcagct gaagtccgga actgcttctg tggtgtgcct gctgaacaat    1980
ttctatccaa gggaagcaaa agtccagtgg aaggtggata acgccctgca gtcaggcaat    2040
agccaggagt ccgtgaccga acaggactct aaagatagta catacagtct gtcaaacacc    2100
ctgacactga gcaaggctga ttatgagaag cacaaagtgt acgcatgcga agtcacccac    2160
caggggctgt cctcaccagt cacaaaatct ttcaatcggg gagaatgc                 2208
```

<210> SEQ ID NO 39
<211> LENGTH: 736
<212> TYPE: PRT
<213> ORGANISM: Artificial Sequence
<220> FEATURE:
<223> OTHER INFORMATION: amino acid sequence of pGX9258: Psuedo-V2L2MD-
YTE only in pGX0001; DMAb-?PcrV operably linked to an IgE leader
sequence

<400> SEQUENCE: 39

```
Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Thr Met Ser Gly Ile Thr Ala Tyr Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Tyr Ile Thr Arg Glu Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350
```

```
Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Val Leu Gln Thr Gln Val Phe Ile Ser
            500                 505                 510

Leu Leu Leu Trp Ile Ser Gly Ala Tyr Gly Ala Ile Gln Met Thr Gln
        515                 520                 525

Ser Pro Ser Ser Leu Ser Ala Ser Val Gly Asp Arg Val Thr Ile Thr
    530                 535                 540

Cys Arg Ala Ser Gln Gly Ile Arg Asn Asp Leu Gly Trp Tyr Gln Gln
545                 550                 555                 560

Lys Pro Gly Lys Ala Pro Lys Leu Leu Ile Tyr Ser Ala Ser Thr Leu
                565                 570                 575

Gln Ser Gly Val Pro Ser Arg Phe Ser Gly Ser Gly Ser Gly Thr Asp
            580                 585                 590

Phe Thr Leu Thr Ile Ser Ser Leu Gln Pro Glu Asp Phe Ala Thr Tyr
        595                 600                 605

Tyr Cys Leu Gln Asp Tyr Asn Tyr Pro Trp Thr Phe Gly Gln Gly Thr
    610                 615                 620

Lys Val Glu Ile Lys Arg Thr Val Ala Ala Pro Ser Val Phe Ile Phe
625                 630                 635                 640

Pro Pro Ser Asp Glu Gln Leu Lys Ser Gly Thr Ala Ser Val Val Cys
                645                 650                 655

Leu Leu Asn Asn Phe Tyr Pro Arg Glu Ala Lys Val Gln Trp Lys Val
            660                 665                 670

Asp Asn Ala Leu Gln Ser Gly Asn Ser Gln Glu Ser Val Thr Glu Gln
        675                 680                 685

Asp Ser Lys Asp Ser Thr Tyr Ser Leu Ser Asn Thr Leu Thr Leu Ser
    690                 695                 700

Lys Ala Asp Tyr Glu Lys His Lys Val Tyr Ala Cys Glu Val Thr His
705                 710                 715                 720

Gln Gly Leu Ser Ser Pro Val Thr Lys Ser Phe Asn Arg Gly Glu Cys
                725                 730                 735
```

<210> SEQ ID NO 40
<211> LENGTH: 702
<212> TYPE: DNA
<213> ORGANISM: Artificial Sequence
<220> FEATURE:
<223> OTHER INFORMATION: nucleotide sequence of pGX9257 light chain:

Pseudo-V2L2MD in pGX0003 (sCMV-light chain, hCMV-heavy chain); DMAb-?PcrV operably linked to a sequence encoding an IgE leader sequence

<400> SEQUENCE: 40

```
atggtcctgc agactcaggt gtttatctca ctgctgctgt ggattagcgg agcatacggg     60

gccattcaga tgacccagtc ccccagttca ctgtccgctt ctgtcggcga cagagtgact    120

atcacctgtc gggcaagcca gggaattcgc aacgatctgg ggtggtatca gcagaagcct    180

gggaaagctc caaagctgct gatctacagt gcatcaactc tgcagtcagg agtgcctagc    240

cggttcagcg gctccggatc tggaaccgac tttacactga ctattagctc cctgcagcca    300

gaggacttcg ccacatatta ctgcctgcag gattataatt acccctggac atttggccag    360

ggaactaaag tggaaatcaa gcgcacagtc gctgcaccta gcgtgttcat ctttccaccc    420

tcagacgagc agctgaagtc cggaactgct tctgtggtgt gcctgctgaa caatttctat    480

ccaagggaag caaaagtcca gtggaaggtg gataacgccc tgcagtcagg caatagccag    540

gagtccgtga ccgaacagga ctctaaagat agtacataca gtctgtcaaa caccctgaca    600

ctgagcaagg ctgattatga gaagcacaaa gtgtacgcat gcgaagtcac ccaccagggg    660

ctgtcctcac cagtcacaaa atctttcaat cggggagaat gc                       702
```

<210> SEQ ID NO 41
<211> LENGTH: 234
<212> TYPE: PRT
<213> ORGANISM: Artificial Sequence
<220> FEATURE:
<223> OTHER INFORMATION: amino acid sequence of pGX9257 light chain: Pseudo-V2L2MD in pGX0003 (sCMV-light chain, hCMV-heavy chain); DMAb-?PcrV operably linked to an IgE leader sequence

<400> SEQUENCE: 41

```
Met Val Leu Gln Thr Gln Val Phe Ile Ser Leu Leu Leu Trp Ile Ser
1               5                   10                  15

Gly Ala Tyr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Arg Asn Asp Leu Gly Trp Tyr Gln Gln Lys Pro Gly Lys Ala Pro
    50                  55                  60

Lys Leu Leu Ile Tyr Ser Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Asn Tyr Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Asn Thr Leu Thr Leu Ser Lys Ala Asp Tyr Glu Lys
```

```
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 42
<211> LENGTH: 3006
<212> TYPE: DNA
<213> ORGANISM: Artificial Sequence
<220> FEATURE:
<223> OTHER INFORMATION: nucleotide sequence of pGX9213: Bispecific
      Pseudomonas (Bis4-V2L2MD/Psl0096); DMAb-BiSPA operably linked to a
      sequence encoding an IgE leader sequence

<400> SEQUENCE: 42

atggactgga catggagaat cctgtttctg gtcgccgccg caactggaac ccacgccgaa      60

gtgcagctgc tggagtcagg gggagggctg gtgcagcccg gcggcagcct gcgactgtct     120

tgcgccgcta gtggcttcac cttcagcagc tatgctatga actgggtccg acaggcacca     180

ggaaagggac tggaatgggt gtctgccatc accatgagtg gaattacagc ttactatact     240

gacgatgtga aggggagatt cacaatctca cgggacaaca gcaaaaatac tctgtacctg     300

cagatgaata gcctgagggc agaggatacc gccgtgtact attgcgccaa ggaggaattc     360

ctgcctggca cacactacta ttacggaatg gacgtgtggg gccagggaac cacagtcacc     420

gtgtctagtg cttcaacaaa ggggccaagc gtgtttccac tggcaccctc aagcaaatca     480

accagcgggg gcacagcagc cctgggatgt ctggtgaagg attacttccc cgagcctgtc     540

accgtgtcat ggaacagcgg agccctgacc tccggagtcc acacatttcc tgctgtgctg     600

cagtcctctg ggctgtattc tctgagttca gtggtcacag tcccaagctc ctctctgggc     660

acacagactt acatctgcaa cgtgaatcat aagccatcca atactaaggt cgacaaacgg     720

gtggagccca aatcttgtgg cggcggcggc agcggcggcg gcggcagcca ggtccagctg     780

caggagagcg gacctggact ggtgaagcca tccgaaacac tgtctctgac ctgcaccgtg     840

agcggcggca gcatctctcc atattactgg acttggatta ggcagccccc tggcaagtgt     900

ctggagctga tcgggtacat tcacagttca ggctataccg actacaaccc ctccctgaag     960

tctagagtga ctatcagtgg cgatacctca aagaaacagt tctccctgaa actgagctcc    1020

gtcactgctg cagacaccgc cgtgtattac tgcgcacgcg ccgactggga tcgactgcgc    1080

gctctggata tctggggaca ggggactatg gtcaccgtgt ctagtggggg cggagggagt    1140

ggcggagggg gctcaggagg gggcggaagc gggggcggag ggtccgacat tcagctgacc    1200

cagagcccct caagcctgag tgcctcagtc ggcgatcgcg tgactatcac ctgtcgagct    1260

agccagtcca ttaggtccca tctgaactgg tatcagcaga agcccggaaa agcacctaag    1320

ctgctgatct acggcgccag caatctgcag tccggagtgc cctctaggtt ctctggcagt    1380

ggatcaggga cagactttac actgactatt tcctctctgc agcctgagga tttcgcaact    1440

tattactgcc agcagagcac cggcgcctgg aactggtttg gctgtggaac caaggtggaa    1500

atcaaaggcg gagggggctc tggagggggc ggaagtgaca agacccacac atgcccaccc    1560

tgtccagcac cagagctgct gggcggccca tccgtgttcc tgtttcctcc aaagcctaaa    1620

gatacactga tgattagcag aacacccgaa gtcacttgcg tggtcgtgga cgtgtcccac    1680

gaggaccccg aagtcaagtt taactggtac gtggacggcg tcgaggtgca taatgccaag    1740

accaaacccc gagaggaaca gtataactca acctacaggg tcgtgagcgt cctgacagtg    1800
```

```
ctgcatcagg attggctgaa cggcaaggag tacaagtgca aagtgtctaa taaggctctg   1860

cctgcaccaa tcgagaaaac tattagcaag gccaaaggcc agcctagaga accacaggtg   1920

tataccctgc ccccttctcg ggaggaaatg acaaagaacc aggtcagcct gacttgtctg   1980

gtgaaaggct tctacccttc tgacatcgct gtggagtggg aaagtaatgg acagccagaa   2040

aacaattata agactacccc acccgtcctg gacagtgatg gctcattctt tctgtacagt   2100

aagctgaccg tggataaatc aaggtggcag cagggaaacg tctttagctg ctccgtgatg   2160

cacgaggccc tgcacaatca ttacacacag aagtctctga gtctgtcacc tggcaagcga   2220

ggaaggaaaa ggagaagcgg gtccggagca accaacttca gcctgctgaa acaggctggg   2280

gacgtggagg aaaatcccgg ccctatggtc ctgcagaccc aggtgtttat ctccctgctg   2340

ctgtggattt ctggggccta cggcgctatc cagatgacac agtctcctag ttcactgtct   2400

gcaagtgtcg gcgacagagt gactatcacc tgtcgggctt cccagggaat tcgcaacgat   2460

ctggggtggt atcagcagaa accaggaaag gctcccaaac tgctgatcta ctcagcaagc   2520

acactgcaga gtggggtgcc atcaagattc tccggatctg ggagtggcac tgacttcacc   2580

ctgactatta gctccctgca gccagaggac ttcgccacct attactgcct gcaggattat   2640

aattacccct ggacatttgg acaggggact aaggtggaga tcaaacggac tgtcgccgct   2700

cccagcgtgt tcatttttcc tccatccgac gaacagctga agagcggaac cgcatccgtg   2760

gtgtgcctgc tgaacaattt ctatcctcgc gaagcaaagg tccagtggaa agtggataac   2820

gccctgcaga gcggcaattc ccaggagtct gtgactgaac aggacagtaa ggattcaacc   2880

tacagcctgt ctagtaccct gacactgtcc aaagctgact atgagaagca taaagtgtac   2940

gcatgtgagg tcacccacca ggggctgtcc agtccagtca ccaagtcttt caataggggc   3000

gaatgc                                                              3006
```

```
<210> SEQ ID NO 43
<211> LENGTH: 1002
<212> TYPE: PRT
<213> ORGANISM: Artificial Sequence
<220> FEATURE:
<223> OTHER INFORMATION: amino acid sequence of pGX9213: Bispecific
      Pseudomonas (Bis4-V2L2MD/Psl0096); DMAb-BiSPA operably linked to
      an IgE leader sequence

<400> SEQUENCE: 43

Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Thr Met Ser Gly Ile Thr Ala Tyr Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125
```

```
Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Gly Gly Gly Gly Ser Gly Gly Gly Gly Ser
                245                 250                 255

Gln Val Gln Leu Gln Glu Ser Gly Pro Gly Leu Val Lys Pro Ser Glu
            260                 265                 270

Thr Leu Ser Leu Thr Cys Thr Val Ser Gly Gly Ser Ile Ser Pro Tyr
        275                 280                 285

Tyr Trp Thr Trp Ile Arg Gln Pro Pro Gly Lys Cys Leu Glu Leu Ile
    290                 295                 300

Gly Tyr Ile His Ser Ser Gly Tyr Thr Asp Tyr Asn Pro Ser Leu Lys
305                 310                 315                 320

Ser Arg Val Thr Ile Ser Gly Asp Thr Ser Lys Lys Gln Phe Ser Leu
                325                 330                 335

Lys Leu Ser Ser Val Thr Ala Ala Asp Thr Ala Val Tyr Tyr Cys Ala
            340                 345                 350

Arg Ala Asp Trp Asp Arg Leu Arg Ala Leu Asp Ile Trp Gly Gln Gly
        355                 360                 365

Thr Met Val Thr Val Ser Ser Gly Gly Gly Gly Ser Gly Gly Gly Gly
    370                 375                 380

Ser Gly Gly Gly Gly Ser Gly Gly Gly Gly Ser Asp Ile Gln Leu Thr
385                 390                 395                 400

Gln Ser Pro Ser Ser Leu Ser Ala Ser Val Gly Asp Arg Val Thr Ile
                405                 410                 415

Thr Cys Arg Ala Ser Gln Ser Ile Arg Ser His Leu Asn Trp Tyr Gln
            420                 425                 430

Gln Lys Pro Gly Lys Ala Pro Lys Leu Leu Ile Tyr Gly Ala Ser Asn
        435                 440                 445

Leu Gln Ser Gly Val Pro Ser Arg Phe Ser Gly Ser Gly Ser Gly Thr
    450                 455                 460

Asp Phe Thr Leu Thr Ile Ser Ser Leu Gln Pro Glu Asp Phe Ala Thr
465                 470                 475                 480

Tyr Tyr Cys Gln Gln Ser Thr Gly Ala Trp Asn Trp Phe Gly Cys Gly
                485                 490                 495

Thr Lys Val Glu Ile Lys Gly Gly Gly Gly Ser Gly Gly Gly Gly Ser
            500                 505                 510

Asp Lys Thr His Thr Cys Pro Pro Cys Pro Ala Pro Glu Leu Leu Gly
        515                 520                 525

Gly Pro Ser Val Phe Leu Phe Pro Pro Lys Pro Lys Asp Thr Leu Met
    530                 535                 540

Ile Ser Arg Thr Pro Glu Val Thr Cys Val Val Val Asp Val Ser His
```

```
545                 550                 555                 560

Glu Asp Pro Glu Val Lys Phe Asn Trp Tyr Val Asp Gly Val Glu Val
                565                 570                 575

His Asn Ala Lys Thr Lys Pro Arg Glu Glu Gln Tyr Asn Ser Thr Tyr
            580                 585                 590

Arg Val Val Ser Val Leu Thr Val Leu His Gln Asp Trp Leu Asn Gly
        595                 600                 605

Lys Glu Tyr Lys Cys Lys Val Ser Asn Lys Ala Leu Pro Ala Pro Ile
    610                 615                 620

Glu Lys Thr Ile Ser Lys Ala Lys Gly Gln Pro Arg Glu Pro Gln Val
625                 630                 635                 640

Tyr Thr Leu Pro Pro Ser Arg Glu Glu Met Thr Lys Asn Gln Val Ser
                645                 650                 655

Leu Thr Cys Leu Val Lys Gly Phe Tyr Pro Ser Asp Ile Ala Val Glu
            660                 665                 670

Trp Glu Ser Asn Gly Gln Pro Glu Asn Asn Tyr Lys Thr Thr Pro Pro
        675                 680                 685

Val Leu Asp Ser Asp Gly Ser Phe Phe Leu Tyr Ser Lys Leu Thr Val
    690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
                725                 730                 735

Pro Gly Lys Arg Gly Arg Lys Arg Arg Ser Gly Ser Gly Ala Thr Asn
            740                 745                 750

Phe Ser Leu Leu Lys Gln Ala Gly Asp Val Glu Glu Asn Pro Gly Pro
        755                 760                 765

Met Val Leu Gln Thr Gln Val Phe Ile Ser Leu Leu Leu Trp Ile Ser
    770                 775                 780

Gly Ala Tyr Gly Ala Ile Gln Met Thr Gln Ser Pro Ser Ser Leu Ser
785                 790                 795                 800

Ala Ser Val Gly Asp Arg Val Thr Ile Thr Cys Arg Ala Ser Gln Gly
                805                 810                 815

Ile Arg Asn Asp Leu Gly Trp Tyr Gln Gln Lys Pro Gly Lys Ala Pro
            820                 825                 830

Lys Leu Leu Ile Tyr Ser Ala Ser Thr Leu Gln Ser Gly Val Pro Ser
        835                 840                 845

Arg Phe Ser Gly Ser Gly Ser Gly Thr Asp Phe Thr Leu Thr Ile Ser
    850                 855                 860

Ser Leu Gln Pro Glu Asp Phe Ala Thr Tyr Tyr Cys Leu Gln Asp Tyr
865                 870                 875                 880

Asn Tyr Pro Trp Thr Phe Gly Gln Gly Thr Lys Val Glu Ile Lys Arg
                885                 890                 895

Thr Val Ala Ala Pro Ser Val Phe Ile Phe Pro Pro Ser Asp Glu Gln
            900                 905                 910

Leu Lys Ser Gly Thr Ala Ser Val Val Cys Leu Leu Asn Asn Phe Tyr
        915                 920                 925

Pro Arg Glu Ala Lys Val Gln Trp Lys Val Asp Asn Ala Leu Gln Ser
    930                 935                 940

Gly Asn Ser Gln Glu Ser Val Thr Glu Gln Asp Ser Lys Asp Ser Thr
945                 950                 955                 960

Tyr Ser Leu Ser Ser Thr Leu Thr Leu Ser Lys Ala Asp Tyr Glu Lys
                965                 970                 975
```

```
His Lys Val Tyr Ala Cys Glu Val Thr His Gln Gly Leu Ser Ser Pro
            980                 985                 990

Val Thr Lys Ser Phe Asn Arg Gly  Glu Cys
        995                 1000


<210> SEQ ID NO 44
<211> LENGTH: 2193
<212> TYPE: DNA
<213> ORGANISM: Artificial Sequence
<220> FEATURE:
<223> OTHER INFORMATION: nucleotide sequence of pGX9215: Pseudo-Ps10096;
      DMAb-?Psl operably linked to a sequence encoding an IgE leader
      sequence

<400> SEQUENCE: 44

atggattgga catggaggat tctgtttctg gtggccgccg ctactggaac ccacgctcag     60

gtgcagctgc aggagtctgg acccggactg gtcaagccta gcgaaactct gtccctgact    120

tgcaccgtgt ccggcggatc aatcagccca tactattgga cctggattcg ccagccccct    180

ggcaagggac tggagctgat cggctacatt cacagctccg gatacaccga ctataaccca    240

tcactgaaaa gccgagtgac aatctctggc gatactagta agaaacagtt cagcctgaag    300

ctgtctagtg tcacagccgc tgacactgca gtgtactatt gcgcccgcgc tgactgggat    360

cgactgcgcg ctctggatat ttgggggcag ggcactatgg tcaccgtgag cagcgcctca    420

accaaaggcc ctagcgtgtt tccactggca ccctcctcta agtccacctc tgggggcaca    480

gcagccctgg gatgtctggt gaaggactac ttccccgagc ctgtcacagt gtcctggaac    540

tctggagccc tgacctccgg ggtccataca tttcccgctg tgctgcagag ttcagggctg    600

tactctctga gctccgtggt caccgtgcct tctagttcac tgggcacaca gacttatatc    660

tgcaacgtga atcacaaacc ttccaataca aaggtcgaca agaaagtgga accaaaatct    720

tgtgataaga cccatacatg cccaccctgt ccagcaccag agctgctggg agggccatcc    780

gtgttcctgt ttcctccaaa gcccaaagac accctgatga ttagccggac tccagaagtc    840

acctgcgtgg tcgtggacgt gtcccacgag gaccccgaag tcaagttcaa ctggtacgtg    900

gatggcgtcg aggtgcataa tgccaagaca aaaccccgag aggaacagta caactccact    960

tatagggtcg tgtctgtcct gaccgtgctg caccaggatt ggctgaacgg gaaggagtat   1020

aagtgcaaag tgtctaacaa ggccctgcct gccccaatcg agaagaccat tagcaaggcc   1080

aaaggccagc ctagagaacc acaggtgtac acactgcccc ctagtcggga cgagctgact   1140

aaaaaccagg tcagcctgac ctgtctggtg aagggcttct atccctcaga tatcgctgtg   1200

gagtgggaat ctaatggaca gcctgaaaac aattacaaga ccacaccacc cgtgctggac   1260

agtgatggat cattctttct gtatagcaaa ctgaccgtgg acaagtccag atggcagcag   1320

gggaacgtct ttagttgctc agtgatgcac gaggccctgc acaatcatta cactcagaaa   1380

agcctgtccc tgtctcccgg caaacgagga aggaagagga gaagtggatc aggggccaca   1440

aacttcagcc tgctgaagca ggctggggat gtggaggaaa atcccggccc tatggtcctg   1500

cagacacagg tgtttatcag tctgctgctg tggatttcag gggcctatgg cgacatccag   1560

ctgactcagt cccctagctc cctgagcgcc tccgtcggag atagagtgac tatcacctgt   1620

cgggcttctc agagtattcg cagccatctg aactggtacc agcagaagcc cgggaaagct   1680

cctaagctgc tgatctatgg agcatcaaat ctgcagagcg gagtgccatc ccggttctca   1740

ggcagcggca gcggaaccga ctttacactg actatttcta gtctgcagcc cgaggatttc   1800
```

```
gcaacatact attgccagca gtccactggc gcctggaact ggtttggcgg agggaccaaa   1860

gtggaaatca agcgcacagt cgctgcacct agcgtgttca tctttcctcc aagtgacgag   1920

cagctgaagt ctggcaccgc cagtgtggtg tgcctgctga acaatttcta cccaagggaa   1980

gcaaaagtcc agtggaaggt ggataacgcc ctgcagagcg gaaattccca ggagtctgtg   2040

acagaacagg acagtaagga ttcaacttac tctctgagta acaccctgac actgagcaag   2100

gctgactacg agaagcacaa agtgtatgca tgcgaggtca cccaccaggg gctgtccagt   2160

ccagtcacta agtccttcaa taggggagaa tgc                                2193


<210> SEQ ID NO 45
<211> LENGTH: 731
<212> TYPE: PRT
<213> ORGANISM: Artificial Sequence
<220> FEATURE:
<223> OTHER INFORMATION: amino acid sequence of pGX9215: Pseudo-Ps10096;
      DMAb-?Psl operably linked to an IgE leader sequence

<400> SEQUENCE: 45

Met Asp Trp Thr Trp Arg Ile Leu Phe Leu Val Ala Ala Ala Thr Gly
1               5                   10                  15

Thr His Ala Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Pro Tyr Tyr Trp Thr Trp Ile Arg Gln Pro Pro Gly Lys Gly Leu
    50                  55                  60

Glu Leu Ile Gly Tyr Ile His Ser Ser Gly Tyr Thr Asp Tyr Asn Pro
65                  70                  75                  80

Ser Leu Lys Ser Arg Val Thr Ile Ser Gly Asp Thr Ser Lys Lys Gln
                85                  90                  95

Phe Ser Leu Lys Leu Ser Ser Val Thr Ala Ala Asp Thr Ala Val Tyr
            100                 105                 110

Tyr Cys Ala Arg Ala Asp Trp Asp Arg Leu Arg Ala Leu Asp Ile Trp
        115                 120                 125

Gly Gln Gly Thr Met Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

```
His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Arg Gly Arg Lys Arg Arg Ser Gly Ser Gly Ala Thr
465                 470                 475                 480

Asn Phe Ser Leu Leu Lys Gln Ala Gly Asp Val Glu Glu Asn Pro Gly
                485                 490                 495

Pro Met Val Leu Gln Thr Gln Val Phe Ile Ser Leu Leu Leu Trp Ile
            500                 505                 510

Ser Gly Ala Tyr Gly Asp Ile Gln Leu Thr Gln Ser Pro Ser Ser Leu
        515                 520                 525

Ser Ala Ser Val Gly Asp Arg Val Thr Ile Thr Cys Arg Ala Ser Gln
    530                 535                 540

Ser Ile Arg Ser His Leu Asn Trp Tyr Gln Gln Lys Pro Gly Lys Ala
545                 550                 555                 560

Pro Lys Leu Leu Ile Tyr Gly Ala Ser Asn Leu Gln Ser Gly Val Pro
                565                 570                 575

Ser Arg Phe Ser Gly Ser Gly Ser Gly Thr Asp Phe Thr Leu Thr Ile
            580                 585                 590

Ser Ser Leu Gln Pro Glu Asp Phe Ala Thr Tyr Tyr Cys Gln Gln Ser
        595                 600                 605

Thr Gly Ala Trp Asn Trp Phe Gly Gly Gly Thr Lys Val Glu Ile Lys
    610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
            660                 665                 670

Ser Gly Asn Ser Gln Glu Ser Val Thr Glu Gln Asp Ser Lys Asp Ser
        675                 680                 685

Thr Tyr Ser Leu Ser Asn Thr Leu Thr Leu Ser Lys Ala Asp Tyr Glu
    690                 695                 700

Lys His Lys Val Tyr Ala Cys Glu Val Thr His Gln Gly Leu Ser Ser
```

705 710 715 720

Pro Val Thr Lys Ser Phe Asn Arg Gly Glu Cys
725 730

<210> SEQ ID NO 46
<211> LENGTH: 3006
<212> TYPE: DNA
<213> ORGANISM: Artificial Sequence
<220> FEATURE:
<223> OTHER INFORMATION: nucleotide sequence of pGX9259: Bispecific Pseudomonas (Bis4-V2L2MD/Psl0096)-YTE only pGX0001; DMAb-BiSPA operably linked to a sequence encoding an IgE leader sequence

<400> SEQUENCE: 46
atggactgga catggagaat cctgtttctg gtcgccgccg caactggaac ccacgccgaa 60
gtgcagctgc tggagtcagg gggagggctg gtgcagcccg gcggcagcct gcgactgtct 120
tgcgccgcta gtggcttcac cttcagcagc tatgctatga actgggtccg acaggcacca 180
ggaaagggac tggaatgggt gtctgccatc accatgagtg gaattacagc ttactatact 240
gacgatgtga aggggagatt cacaatctca cgggacaaca gcaaaaatac tctgtacctg 300
cagatgaata gcctgagggc agaggatacc gccgtgtact attgcgccaa ggaggaattc 360
ctgcctggca cacactacta ttacggaatg gacgtgtggg gccagggaac cacagtcacc 420
gtgtctagtg cttcaacaaa ggggccaagc gtgtttccac tggcaccctc aagcaaatca 480
accagcgggg gcacagcagc cctgggatgt ctggtgaagg attacttccc cgagcctgtc 540
accgtgtcat ggaacagcgg agccctgacc tccggagtcc acacatttcc tgctgtgctg 600
cagtcctctg gctgtattc tctgagttca gtggtcacag tcccaagctc ctctctgggc 660
acacagactt acatctgcaa cgtgaatcat aagccatcca atactaaggt cgacaaacgg 720
gtggagccca aatcttgtgg cggcggcggc agcggcggcg gcggcagcca ggtccagctg 780
caggagagcg gacctggact ggtgaagcca tccgaaacac tgtctctgac ctgcaccgtg 840
agcggcggca gcatctctcc atattactgg acttggatta ggcagccccc tggcaagtgt 900
ctggagctga tcgggtacat tcacagttca ggctataccg actacaaccc ctccctgaag 960
tctagagtga ctatcagtgg cgatacctca aagaaacagt tctccctgaa actgagctcc 1020
gtcactgctg cagacaccgc cgtgtattac tgcgcacgcg ccgactggga tcgactgcgc 1080
gctctggata tctggggaca ggggactatg gtcaccgtgt ctagtggggg cggagggagt 1140
ggcggagggg gctcaggagg gggcggaagc gggggcggag ggtccgacat tcagctgacc 1200
cagagcccct caagcctgag tgcctcagtc ggcgatcgcg tgactatcac ctgtcgagct 1260
agccagtcca ttaggtccca tctgaactgg tatcagcaga agcccggaaa agcacctaag 1320
ctgctgatct acggcgccag caatctgcag tccggagtgc cctctaggtt ctctggcagt 1380
ggatcaggga cagactttac actgactatt tcctctctgc agcctgagga tttcgcaact 1440
tattactgcc agcagagcac cggcgcctgg aactggtttg gctgtggaac caaggtggaa 1500
atcaaaggcg gagggggctc tggagggggc ggaagtgaca agacccacac atgcccaccc 1560
tgtccagcac cagagctgct gggcggccca tccgtgttcc tgtttcctcc aaagcctaaa 1620
gatacactgt atattactag agagcccgaa gtcacttgcg tggtcgtgga cgtgtcccac 1680
gaggaccccg aagtcaagtt taactggtac gtggacggcg tcgaggtgca taatgccaag 1740
accaaacccc gagaggaaca gtataactca acctacaggg tcgtgagcgt cctgacagtg 1800
ctgcatcagg attggctgaa cggcaaggag tacaagtgca aagtgtctaa taaggctctg 1860

```
cctgcaccaa tcgagaaaac tattagcaag gccaaaggcc agcctagaga accacaggtg   1920

tataccctgc cccttctcg ggaggaaatg acaaagaacc aggtcagcct gacttgtctg    1980

gtgaaaggct tctacccttc tgacatcgct gtggagtggg aaagtaatgg acagccagaa   2040

aacaattata agactacccc acccgtcctg gacagtgatg gctcattctt tctgtacagt   2100

aagctgaccg tggataaatc aaggtggcag cagggaaacg tctttagctg ctccgtgatg   2160

cacgaggccc tgcacaatca ttacacacag aagtctctga gtctgtcacc tggcaagcga   2220

ggaaggaaaa ggagaagcgg gtccggagca accaacttca gcctgctgaa acaggctggg   2280

gacgtggagg aaaatcccgg ccctatggtc ctgcagaccc aggtgtttat ctccctgctg   2340

ctgtggattt ctggggccta cggcgctatc cagatgacac agtctcctag ttcactgtct   2400

gcaagtgtcg gcgacagagt gactatcacc tgtcgggctt cccagggaat tcgcaacgat   2460

ctggggtggt atcagcagaa accaggaaag gctcccaaac tgctgatcta ctcagcaagc   2520

acactgcaga gtggggtgcc atcaagattc tccggatctg ggagtggcac tgacttcacc   2580

ctgactatta gctccctgca gccagaggac ttcgccacct attactgcct gcaggattat   2640

aattacccct ggacatttgg acaggggact aaggtggaga tcaaacggac tgtcgccgct   2700

cccagcgtgt tcatttttcc tccatccgac gaacagctga agagcggaac cgcatccgtg   2760

gtgtgcctgc tgaacaattt ctatcctcgc gaagcaaagg tccagtggaa agtggataac   2820

gccctgcaga gcggcaattc ccaggagtct gtgactgaac aggacagtaa ggattcaacc   2880

tacagcctgt ctagtaccct gacactgtcc aaagctgact atgagaagca taaagtgtac   2940

gcatgtgagg tcacccacca ggggctgtcc agtccagtca ccaagtcttt caataggggc   3000

gaatgc                                                              3006
```

```
<210> SEQ ID NO 47
<211> LENGTH: 1002
<212> TYPE: PRT
<213> ORGANISM: Artificial Sequence
<220> FEATURE:
<223> OTHER INFORMATION: amino acid sequence of pGX9259: Bispecific
      Pseudomonas (Bis4-V2L2MD/Psl0096)-YTE only pGX0001; DMAb-BiSPA
      operably linked to an IgE leader sequence

<400> SEQUENCE: 47

Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Asn Trp Val Arg Gln Ala Pro Gly Lys Gly Leu
    50                  55                  60

Glu Trp Val Ser Ala Ile Thr Met Ser Gly Ile Thr Ala Tyr Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Glu Phe Leu Pro Gly Thr His Tyr Tyr Tyr
        115                 120                 125

Gly Met Asp Val Trp Gly Gln Gly Thr Thr Val Thr Val Ser Ser Ala
    130                 135                 140
```

Ser Thr Lys Gly Pro Ser Val Phe Pro Leu Ala Pro Ser Ser Lys Ser
145 150 155 160

Thr Ser Gly Gly Thr Ala Ala Leu Gly Cys Leu Val Lys Asp Tyr Phe
165 170 175

Pro Glu Pro Val Thr Val Ser Trp Asn Ser Gly Ala Leu Thr Ser Gly
180 185 190

Val His Thr Phe Pro Ala Val Leu Gln Ser Ser Gly Leu Tyr Ser Leu
195 200 205

Ser Ser Val Val Thr Val Pro Ser Ser Ser Leu Gly Thr Gln Thr Tyr
210 215 220

Ile Cys Asn Val Asn His Lys Pro Ser Asn Thr Lys Val Asp Lys Arg
225 230 235 240

Val Glu Pro Lys Ser Cys Gly Gly Gly Gly Ser Gly Gly Gly Gly Ser
245 250 255

Gln Val Gln Leu Gln Glu Ser Gly Pro Gly Leu Val Lys Pro Ser Glu
260 265 270

Thr Leu Ser Leu Thr Cys Thr Val Ser Gly Gly Ser Ile Ser Pro Tyr
275 280 285

Tyr Trp Thr Trp Ile Arg Gln Pro Pro Gly Lys Cys Leu Glu Leu Ile
290 295 300

Gly Tyr Ile His Ser Ser Gly Tyr Thr Asp Tyr Asn Pro Ser Leu Lys
305 310 315 320

Ser Arg Val Thr Ile Ser Gly Asp Thr Ser Lys Lys Gln Phe Ser Leu
325 330 335

Lys Leu Ser Ser Val Thr Ala Ala Asp Thr Ala Val Tyr Tyr Cys Ala
340 345 350

Arg Ala Asp Trp Asp Arg Leu Arg Ala Leu Asp Ile Trp Gly Gln Gly
355 360 365

Thr Met Val Thr Val Ser Ser Gly Gly Gly Gly Ser Gly Gly Gly Gly
370 375 380

Ser Gly Gly Gly Gly Ser Gly Gly Gly Gly Ser Asp Ile Gln Leu Thr
385 390 395 400

Gln Ser Pro Ser Ser Leu Ser Ala Ser Val Gly Asp Arg Val Thr Ile
405 410 415

Thr Cys Arg Ala Ser Gln Ser Ile Arg Ser His Leu Asn Trp Tyr Gln
420 425 430

Gln Lys Pro Gly Lys Ala Pro Lys Leu Leu Ile Tyr Gly Ala Ser Asn
435 440 445

Leu Gln Ser Gly Val Pro Ser Arg Phe Ser Gly Ser Gly Ser Gly Thr
450 455 460

Asp Phe Thr Leu Thr Ile Ser Ser Leu Gln Pro Glu Asp Phe Ala Thr
465 470 475 480

Tyr Tyr Cys Gln Gln Ser Thr Gly Ala Trp Asn Trp Phe Gly Cys Gly
485 490 495

Thr Lys Val Glu Ile Lys Gly Gly Gly Gly Ser Gly Gly Gly Gly Ser
500 505 510

Asp Lys Thr His Thr Cys Pro Pro Cys Pro Ala Pro Glu Leu Leu Gly
515 520 525

Gly Pro Ser Val Phe Leu Phe Pro Pro Lys Pro Lys Asp Thr Leu Tyr
530 535 540

Ile Thr Arg Glu Pro Glu Val Thr Cys Val Val Val Asp Val Ser His
545 550 555 560

Glu Asp Pro Glu Val Lys Phe Asn Trp Tyr Val Asp Gly Val Glu Val

```
                565                 570                 575

His Asn Ala Lys Thr Lys Pro Arg Glu Glu Gln Tyr Asn Ser Thr Tyr
            580                 585                 590

Arg Val Val Ser Val Leu Thr Val Leu His Gln Asp Trp Leu Asn Gly
        595                 600                 605

Lys Glu Tyr Lys Cys Lys Val Ser Asn Lys Ala Leu Pro Ala Pro Ile
    610                 615                 620

Glu Lys Thr Ile Ser Lys Ala Lys Gly Gln Pro Arg Glu Pro Gln Val
625                 630                 635                 640

Tyr Thr Leu Pro Pro Ser Arg Glu Glu Met Thr Lys Asn Gln Val Ser
                645                 650                 655

Leu Thr Cys Leu Val Lys Gly Phe Tyr Pro Ser Asp Ile Ala Val Glu
            660                 665                 670

Trp Glu Ser Asn Gly Gln Pro Glu Asn Asn Tyr Lys Thr Thr Pro Pro
        675                 680                 685

Val Leu Asp Ser Asp Gly Ser Phe Phe Leu Tyr Ser Lys Leu Thr Val
    690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
                725                 730                 735

Pro Gly Lys Arg Gly Arg Lys Arg Arg Ser Gly Ser Gly Ala Thr Asn
            740                 745                 750

Phe Ser Leu Leu Lys Gln Ala Gly Asp Val Glu Glu Asn Pro Gly Pro
        755                 760                 765

Met Val Leu Gln Thr Gln Val Phe Ile Ser Leu Leu Leu Trp Ile Ser
    770                 775                 780

Gly Ala Tyr Gly Ala Ile Gln Met Thr Gln Ser Pro Ser Ser Leu Ser
785                 790                 795                 800

Ala Ser Val Gly Asp Arg Val Thr Ile Thr Cys Arg Ala Ser Gln Gly
                805                 810                 815

Ile Arg Asn Asp Leu Gly Trp Tyr Gln Gln Lys Pro Gly Lys Ala Pro
            820                 825                 830

Lys Leu Leu Ile Tyr Ser Ala Ser Thr Leu Gln Ser Gly Val Pro Ser
        835                 840                 845

Arg Phe Ser Gly Ser Gly Ser Gly Thr Asp Phe Thr Leu Thr Ile Ser
    850                 855                 860

Ser Leu Gln Pro Glu Asp Phe Ala Thr Tyr Tyr Cys Leu Gln Asp Tyr
865                 870                 875                 880

Asn Tyr Pro Trp Thr Phe Gly Gln Gly Thr Lys Val Glu Ile Lys Arg
                885                 890                 895

Thr Val Ala Ala Pro Ser Val Phe Ile Phe Pro Pro Ser Asp Glu Gln
            900                 905                 910

Leu Lys Ser Gly Thr Ala Ser Val Val Cys Leu Leu Asn Asn Phe Tyr
        915                 920                 925

Pro Arg Glu Ala Lys Val Gln Trp Lys Val Asp Asn Ala Leu Gln Ser
    930                 935                 940

Gly Asn Ser Gln Glu Ser Val Thr Glu Gln Asp Ser Lys Asp Ser Thr
945                 950                 955                 960
```

-continued

```
Tyr Ser Leu Ser Ser Thr Leu Thr Leu Ser Lys Ala Asp Tyr Glu Lys
                965                 970                 975

His Lys Val Tyr Ala Cys Glu Val Thr His Gln Gly Leu Ser Ser Pro
            980                 985                 990

Val Thr Lys Ser Phe Asn Arg Gly  Glu Cys
        995                  1000
```